(12) United States Patent
Collins et al.

(10) Patent No.: US 12,083,277 B2
(45) Date of Patent: Sep. 10, 2024

(54) NASAL RESPIRATORY INTERFACE AND ADJUSTABLE HEADGEAR

(71) Applicant: FISHER & PAYKEL HEALTHCARE LIMITED, Auckland (NZ)

(72) Inventors: Janine Elizabeth Collins, Auckland (NZ); Adam Luke Gilbert, Auckland (NZ); Thomas Mark Richardson, Auckland (NZ); Chris Onin Limpin Hipolito, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 465 days.

(21) Appl. No.: 17/538,500

(22) Filed: Nov. 30, 2021

(65) Prior Publication Data

US 2022/0152332 A1   May 19, 2022

Related U.S. Application Data

(63) Continuation of application No. 16/081,394, filed as application No. PCT/NZ2017/050021 on Mar. 1, 2017, now Pat. No. 11,219,731.

(Continued)

(51) Int. Cl.
  *A61M 16/06*   (2006.01)
(52) U.S. Cl.
  CPC .... *A61M 16/0611* (2014.02); *A61M 16/0666* (2013.01); *A61M 16/0694* (2014.02); *A61M 16/0688* (2014.02); *A61M 2210/0618* (2013.01)

(58) Field of Classification Search
  CPC .............. A61M 16/06; A61M 16/0605; A61M 16/0633; A61M 16/0638; A61M 16/0644;
  (Continued)

(56) References Cited

U.S. PATENT DOCUMENTS

| 4,097,934 A | 7/1978 | Weinstein |
|---|---|---|
| 6,044,844 A | 4/2000 | Kwok |

(Continued)

FOREIGN PATENT DOCUMENTS

| EP | 2 130 563 | 2/2012 |
|---|---|---|
| WO | WO 15/079396 | 6/2015 |
| WO | WO 17/030447 | 2/2017 |

*Primary Examiner* — Kendra D Carter
*Assistant Examiner* — Brian T Khong
(74) *Attorney, Agent, or Firm* — Knobbe, Martens, Olson & Bear, LLP

(57) ABSTRACT

A headgear, for use in combination with a breathing apparatus, has a plastic or elastomer core and a fabric or textile casing. The headgear, or portions thereof, may also include a length adjustment arrangement that permits adjustment of a length of a section of the headgear. The length adjustment arrangement can comprise overlapping strap portions of the headgear. In some configurations, the overlapping strap portions can be covered by a sleeve. The sleeve can be secured to the headgear by overmolded end caps. A nasal respiratory interface can include a frame having a front surface, a rear surface, and an aperture extending from the front surface to the rear surface. The frame can have an oval form with a truncated height portion. The interface can also include a seal for a nasal pillow. The seal can be attached to the frame.

15 Claims, 49 Drawing Sheets

Related U.S. Application Data

(60) Provisional application No. 62/303,211, filed on Mar. 3, 2016, provisional application No. 62/302,453, filed on Mar. 2, 2016.

(58) Field of Classification Search
CPC ............ A61M 16/065; A61M 16/0655; A61M 16/0683; A61M 16/0694; A62B 18/084
See application file for complete search history.

(56) References Cited

U.S. PATENT DOCUMENTS

| | | |
|---|---|---|
| 7,210,481 B1 | 5/2007 | Lovell |
| 11,219,731 B2 | 1/2022 | Collins et al. |
| 2003/0196655 A1 | 10/2003 | Ging |
| 2003/0196656 A1 | 10/2003 | Moore |
| 2003/0196658 A1 | 10/2003 | Ging |
| 2004/0221850 A1 | 11/2004 | Ging |
| 2004/0226566 A1 | 11/2004 | Gunaratnam |
| 2004/0261797 A1 | 12/2004 | White |
| 2005/0155604 A1 | 7/2005 | Ging |
| 2005/0241644 A1 | 11/2005 | Gunaratnam |
| 2006/0112962 A1 | 6/2006 | Tebbutt |
| 2006/0196511 A1 | 9/2006 | Lau |
| 2009/0044808 A1 | 2/2009 | Guney |
| 2009/0199856 A1* | 8/2009 | Berlin ............... A61M 16/0683 128/206.13 |
| 2010/0000534 A1 | 1/2010 | Kooij |
| 2010/0000537 A1 | 1/2010 | McAuley et al. |
| 2010/0229868 A1* | 9/2010 | Rummery ......... A61M 16/0875 264/156 |
| 2010/0258136 A1 | 10/2010 | Doherty |
| 2010/0313891 A1 | 12/2010 | Veliss |
| 2011/0146685 A1 | 6/2011 | Allan |
| 2011/0155140 A1 | 6/2011 | Ho |
| 2011/0220115 A1 | 9/2011 | Castiglione |
| 2011/0265796 A1 | 11/2011 | Amarasinghe |
| 2011/0308520 A1 | 12/2011 | McAuley |
| 2012/0067349 A1 | 3/2012 | Barlow |
| 2012/0132209 A1* | 5/2012 | Rummery ......... A61M 16/0622 128/205.25 |
| 2012/0138060 A1 | 6/2012 | Barlow |
| 2012/0304999 A1* | 12/2012 | Swift .................... A61M 16/06 128/205.25 |
| 2013/0152938 A1 | 6/2013 | Jablonski |
| 2013/0186404 A1 | 7/2013 | Chien |
| 2013/0220327 A1* | 8/2013 | Barlow ............. A61M 16/0816 128/205.25 |
| 2013/0276790 A1 | 10/2013 | Moulton et al. |
| 2014/0311494 A1 | 10/2014 | Gibson et al. |
| 2015/0224274 A1 | 8/2015 | Siew |
| 2015/0328423 A1 | 11/2015 | Siew et al. |
| 2016/0067441 A1 | 3/2016 | Bearne |
| 2016/0074614 A1 | 3/2016 | Huddart |
| 2016/0151596 A1 | 6/2016 | Slight |
| 2017/0274167 A1 | 9/2017 | Huddart |

* cited by examiner

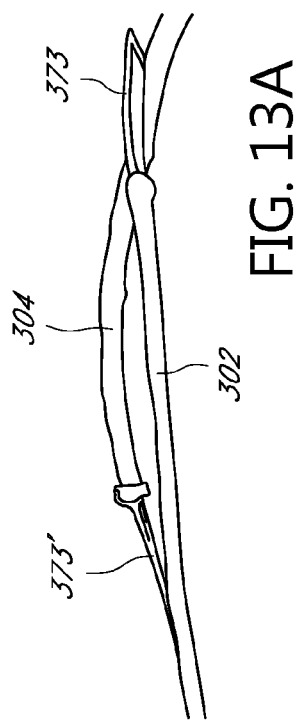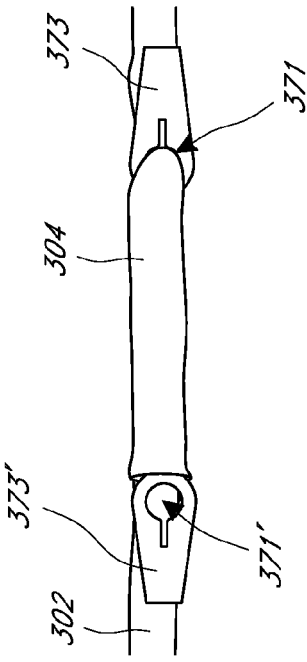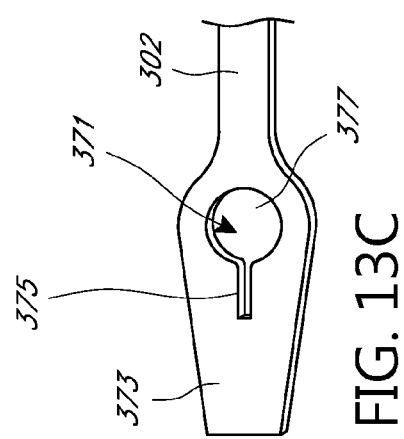

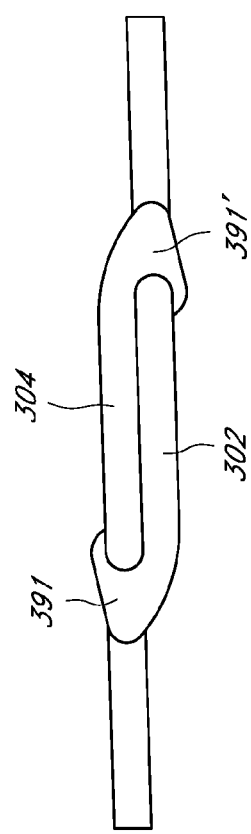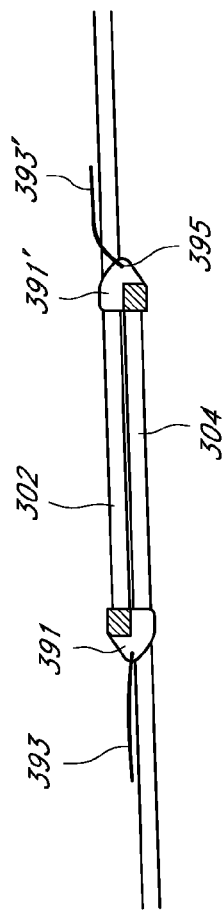

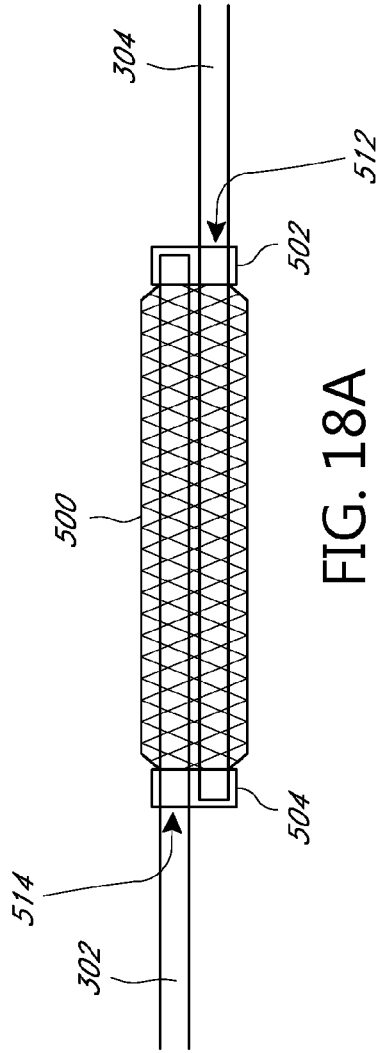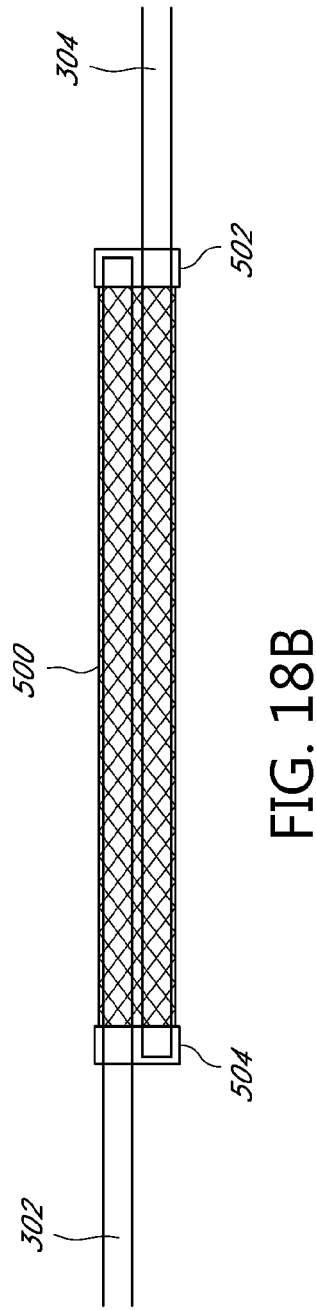

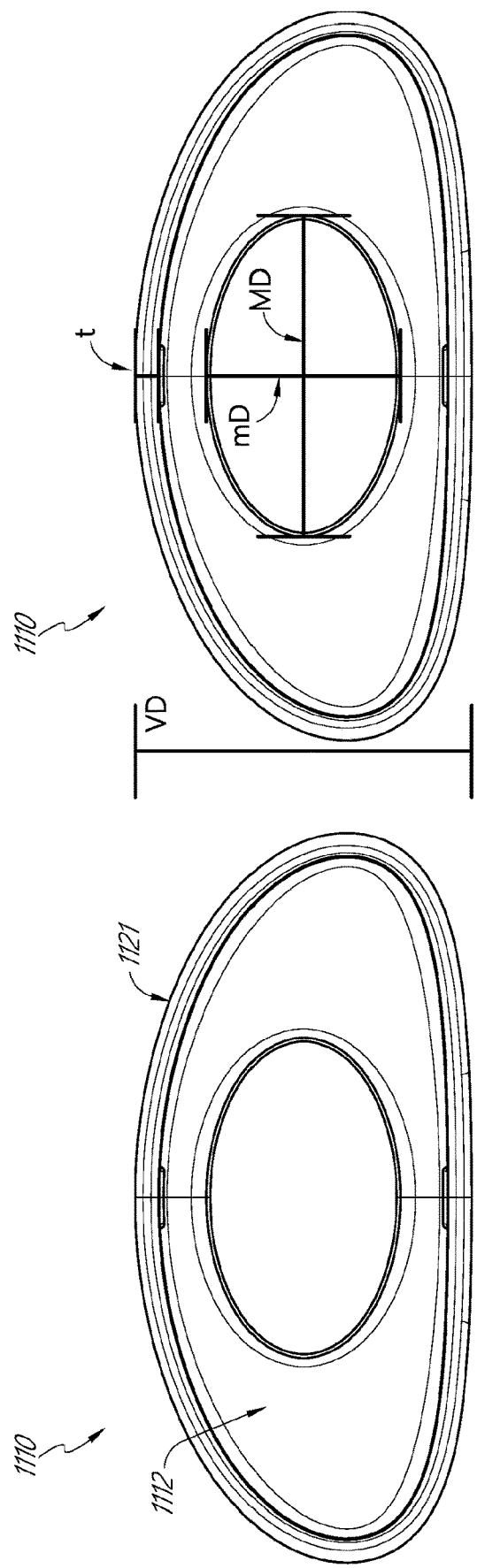
FIG. 36A
FIG. 36B
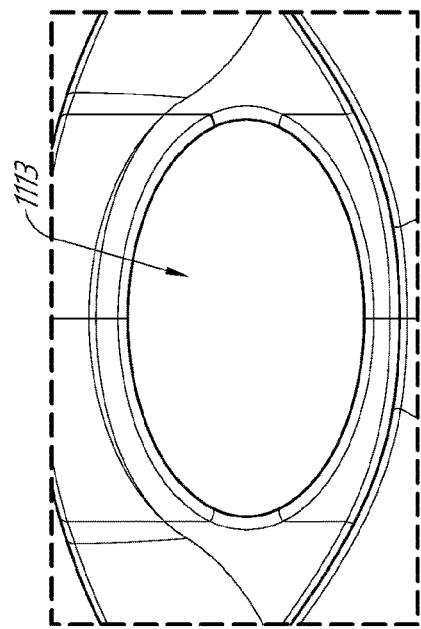
FIG. 37

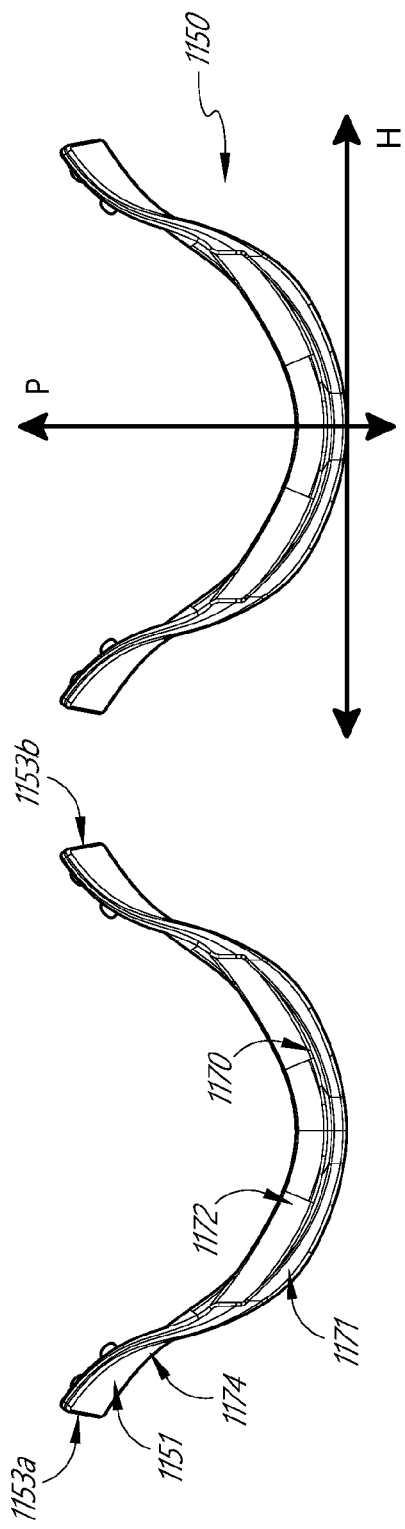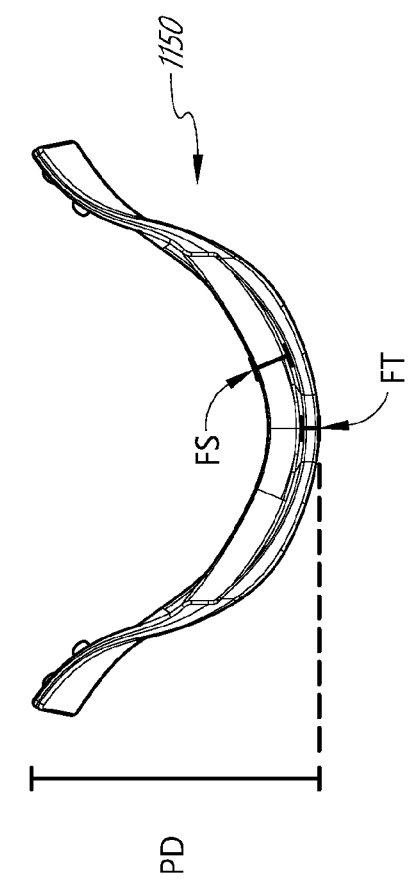
FIG. 42A  FIG. 42B  FIG. 42C

NASAL RESPIRATORY INTERFACE AND ADJUSTABLE HEADGEAR

BACKGROUND

Technical Field

The present disclosure generally relates to apparatus for treating at least some respiratory conditions or illnesses, in particular, to nasal respiratory interfaces. The present disclosure relates to headgear for use in combination with a breathing apparatus. More particularly, the present disclosure relates to a headgear having adjustment features for sizing the headgear to the user. Methods for forming the straps of the headgear are also disclosed.

Description of the Related Art

Obstructive Sleep Apnea (OSA) is a sleep disorder in which muscles that normally hold the airway open relax and ultimately collapse, sealing the airway. The sleep pattern of an OSA sufferer is characterized by repeated sequences of snoring, breathing difficulty, lack of breathing, waking with a start and then returning to sleep. Sufferers of OSA usually experience daytime drowsiness and irritability due to a lack of good continuous sleep.

In an effort to treat OSA sufferers, a nasal mask can be used to supply pressurized gases to a patient. The pressurized air supplied to the patient can effectively assist the muscles to keep the patient's airway open, eliminating the typical OSA sleep pattern. The air can be supplied to the airway by a motor driven blower whose outlet passes via an air delivery hose to a nose, full face, nose and mouth, or oral mask that is sealingly engaged to a patient's face, preferably by a harness or other headgear. An exhaust port can also be provided in the delivery tube proximate to the mask or on the mask itself.

An important feature of respiratory masks has been that they provide an effective seal against the user's face to prevent leakage of the gas being supplied. Commonly, a good mask-to-face seal results in considerable discomfort for the user. In addition, nasal masks can be noisy due to air leaks. These disadvantages in many cases are a formidable obstacle to patient acceptance of such treatment. Therefore, a substantial number of patients either cannot, tolerate treatment or choose to forego treatment. It is believed a number of such patients might benefit from a nasal airway pressure apparatus that is more convenient to use and comfortable to wear, thereby resulting in increased treatment compliance.

In addition, the treatment of other respiratory ailments or conditions with therapies, such as NIV (noninvasive ventilation), Bi-level or CPAP (continuous positive airway pressure), can also involve the delivery of pressurized air to the airways of a human via a conduit and a breathing apparatus (e.g., a mask or cannula). Typically, a mask creates at least a substantial "seal" on or around the nose and/or the mouth of a user while a cannula does not provide a seal but provides a delivery pathway for supplemental respiratory gas delivery.

This "seal" can result in the combination of the enclosure area of the breathing apparatus and its internal pressure creating a force that attempts to push the breathing apparatus off of the face of the user. To counteract this force, it is normal to use a headgear comprising one or more straps that pass around the back and/or top of a user's head. Headgear such as this are typically made from a compliant material, such as Breath-o-prene™. The use of such a material results in the headgear having relatively little structure when not being worn. This lack of structure can give rise to the straps of the headgear becoming tangled, which in turn can make it difficult for a user to don the headgear and breathing apparatus.

These traditional headgear are usually configured to have some elasticity. This can result in the headgear stretching over, and applying pinching forces to, the user's head, which can be uncomfortable. It is desirable to make headgear and breathing apparatus that are easy to use and comfortable to wear because this may improve a user's compliance with the therapy being provided. Also, it can be desirable that the headgear include adjustment features that allow a user to size the headgear to the user's head, thereby improving comfort and efficacy of the headgear.

BRIEF SUMMARY

The present disclosure relates to headgear for use in combination with a breathing apparatus, wherein the headgear may at least go some way towards improving on the above or that may at least provide the public with a useful choice.

In accordance with at least one of the embodiments disclosed herein, a headgear is provided comprising a top strap, a rear strap, a front strap, a junction and a connector. The headgear is configured to use a semi-rigid, lightweight, and unobtrusive soft touch headgear design to support a breathing apparatus (e.g., a nasal under-nose interface from Fisher & Paykel Healthcare) and seal the breathing apparatus to the user with one or more adjustable straps that are configured to accommodate about 95% of the relevant user population.

According to a further aspect, the top strap is designed to allow intuitive and easy adjustment of the semi-rigid headgear.

According to a further aspect, the headgear is designed to reduce pressure experienced by the user while improving the seal of the interface with the breathing apparatus.

According to a further aspect, the headgear is constructed from a composite material, wherein a textile casing is integrally formed about a plastic core.

According to a further aspect, the headgear comprises integrally molded labels, connections, and/or adjustment features.

According to a further aspect, a headgear component comprises a grip that is molded to a textile strap.

In some configurations, an adjustable headgear includes a first strap having a first endcap attached to the first strap. The first endcap has a first through hole. A second strap has a second endcap attached to the second strap. The second endcap has a second through hole. The first strap passes through the second through hole and the second strap passes through the first through hole. A sleeve extends between the first and second endcaps and surrounds the first and second straps.

In some configurations, the sleeve is braided.

In some configurations, the sleeve is elastic.

In some configurations, the first and second endcaps are overmolded onto the sleeve.

In some configurations, a detent arrangement comprises a plurality of relative adjustment positions between the first strap and the second strap.

In some configurations, a first tab is coupled to the first endcap and a second tab is coupled to the second endcap.

In some configurations, the first tab and the second tab are coupled to a center of the respective first endcap and second endcap.

In some configurations, the first strap and the second strap are positioned one on top of the other when overlapped.

In some configurations, the first strap and the second strap are positioned one beside the other when overlapped.

In some configurations, the first strap and the second strap are located in one or both of a top strap and a rear strap of the headgear.

In some configurations, the first strap and the second strap are in frictional contact with one another to provide a resistance to relative movement of the first strap and the second strap.

In some configurations, the first strap and the second strap each comprise a plastic core and a textile covering.

In some configurations, the textile covering covers an inner and an outer surface of each of the first strap and the second strap.

In some configurations, the textile covering comprises a first layer and a second layer.

In some configurations, the textile covering comprises a tube.

In some configurations, a method of making an adjustable headgear includes assembling a first separator onto a first strap such that the first separator surrounds the first strap. A second strap is positioned adjacent the first separator. A sleeve is positioned over the first strap, the second strap and the first separator. The first separator and the sleeve are clamped in a first clamp. The assembly of the first clamp, the first separator, the first strap, the second strap and the sleeve are placed into a mold. The mold is used to form a plastic first endcap over the first separator, wherein the first endcap secures the second strap to the sleeve, and wherein the first separator prevents the first endcap from being secured to the first strap such that the first strap is movable relative to the first endcap.

In some configurations, the first separator is removed from the first endcap.

In some configurations, the method further comprises: assembling a second separator onto the second strap such that the second separator surrounds the second strap; positioning the first strap adjacent the second separator; positioning the sleeve over the first strap, the second strap and the second separator; clamping the second separator and the sleeve in a second clamp; placing the assembly of the second clamp, the second separator, the first strap, the second strap and the sleeve into the mold; using the mold to form a plastic second endcap over the second separator, wherein the second endcap secures the first strap to the sleeve, and wherein the second separator prevents the second endcap from being secured to the second strap such that the second strap is movable relative to the second endcap.

In some configurations, the method further comprises using the mold to form at least a portion of a detent arrangement comprising a plurality of relative adjustment positions between the first strap and the second strap.

In some configurations, an adjustable headgear includes a first strap comprising a plastic core and a textile covering. A second strap comprises a plastic core and a textile covering. The headgear defines an overlapping portion wherein the first strap and the second strap overlap one another. The overlapping portion is adjustable in length to permit adjustment of a combined length of the first strap and the second strap. The first strap and the second strap are in frictional contact with one another within the overlapping portion to provide a resistance to relative movement of the first strap and the second strap.

In some configurations, the first strap and the second strap are positioned one on top of the other within the overlapping portion.

In some configurations, the first strap comprises a first loop that surrounds the second strap.

In some configurations, an upper portion of the first loop is offset from a lower portion of the first loop along a length of the second strap.

In some configurations, a tab is coupled to the first loop.

In some configurations, the tab is coupled to a center of the first loop.

In some configurations, the second strap comprises a second loop that surrounds the first strap.

In some configurations, the second loop is defined by an end portion having a keyhole.

In some configurations, the first loop is defined by an end portion having a keyhole.

In some configurations, a first tab is carried by the first strap and a second tab is carried by the second strap, wherein the first tab can be releasably secured to the second strap and the second tab can be releasably secured to the first strap to assist in maintaining a relative adjusted position of the first strap and the second strap.

In some configurations, each of the first tab and the second tab is constructed from a foldable material, wherein each of the first tab and the second tab is folded when in a released position and is unfolded in a secured position when the tab is secured to the opposite strap.

In some configurations, each of the first tab and the second tab comprises a protrusion configured to contact the opposite strap when the tab is in the secured position to provide a concentrated frictional engagement with the opposite strap.

In some configurations, the textile covering covers an inner and an outer surface of each of the first strap and the second strap.

In some configurations, the textile covering comprises a first layer and a second layer.

Certain embodiments described herein include a nasal respiratory interface. The nasal respiratory interface can comprise a frame having a front surface, a rear surface, and an aperture extending from the front surface to the rear surface. The frame can have an oval form with a truncated height portion. The interface can also include a seal for a nasal pillow. The seal can be attached to the frame. In various embodiments, the seal can be removably attached to the frame.

In some embodiments, the interface can further include a yoke having a front surface and a rear surface. The yoke can be configured to couple the frame to a headgear system. The interface can also include a conduit connector. The conduit connector can be configured to allow gas from a gas delivery conduit through the aperture of the frame towards the nasal pillow.

In various embodiments, the aperture of the frame and/or the conduit connector can comprise an oval shape. In some embodiments, the frame can comprise a recessed surface extending partially around the aperture. For example, the frame can comprise an oval shape having a major axis and a minor axis. The recessed surface can extend adjacent the major axis of the aperture at a first end, under the aperture, and adjacent the major axis of the aperture at a second end. In some such embodiments, the yoke can comprise a recessed wall and a shelf. The recessed wall of the yoke can be configured to mate with the recessed surface of the frame. In some embodiments, the frame can sit on the shelf of the yoke. The front surface of the frame can comprise the recessed surface of the frame. The rear surface of the yoke can comprise the recessed wall of the yoke. When coupled, the front surface of the frame and the front surface of the yoke can form a substantially flush surface.

The recessed wall of the yoke can be configured to mate with the recessed surface of the frame via a connection comprising at least one locating projection and at least one recessed locator. For example, at least one locating projection can comprise at least two locating projections and the at least one recessed locator can comprise at least two recessed locators. At least one locating projection or at least one recessed locator can comprise bias flow holes or a diffuser.

In some embodiments, the yoke can comprise a recessed surface, and the frame can comprise a recessed wall and a shelf. The recessed wall of the frame can be configured to mate with the recessed surface of the yoke. In some instances, the yoke can sit on the shelf of the frame. The front surface of the yoke can comprise the recessed surface of the yoke, and the rear surface of the frame can comprise the recessed wall of the frame. When coupled, the front surface of the frame and the front surface of the yoke can form a substantially flush surface. The recessed wall of the frame can be configured to mate with the recessed surface of the yoke via a connection comprising at least one locating projection and at least one recessed locator. For example, at least one locating projection can comprise at least two locating projections and at least one recessed locator can comprise at least two recessed locators. At least one locating projection or at least one recessed locator can comprise bias flow holes or a diffuser.

In some embodiments, the yoke can comprise a first apex at a first end and a second apex at a second end. The yoke can comprise a top lateral surface and a bottom lateral surface. The top lateral surface can be longer in length than the bottom lateral surface. In various embodiments, the frame can comprise a retaining lip extending around the frame configured to couple the frame to a seal clip. The rear surface of the yoke can be configured to support a bean shaped seal. The yoke can be configured to couple with a head strap to form a closed loop. In some embodiments, the yoke and headgear system can be separated from the frame and conduit connector.

BRIEF DESCRIPTION OF THE DRAWINGS

FIG. 13A is a side view of another embodiment of a size adjustment system for a headgear of the present disclosure.

FIG. 13B is a top view of the size adjustment system of FIG. 13A.

FIG. 13C illustrates a strap connector end of the size adjustment system of FIG. 13A.

FIG. 17A is a top view of a size adjustment system for use with the presently disclosed headgear.

FIG. 17B is a top view of a modification of the size adjustment system of FIG. 17A.

FIG. 18A is a side view of a size adjustment system having a braided sleeve for use with the presently disclosed headgear, wherein the size adjustment system is shown in a first position.

FIG. 18B is a side view of the size adjustment system of FIG. 18A in a second position in which the braided sleeve is elongated relative to the first position.

FIGS. 36A-36B show rear views of the example frame 1110 of the nasal respiratory interface 1100 shown in FIG. 31.

FIG. 37 shows a front view of the aperture 1113 of the example frame 1110 of the nasal respiratory interface 1100 shown in FIG. 31.

FIGS. 42A, 42B, and 42C show top views of the example yoke 1150 showing example features.

DETAILED DESCRIPTION

As used herein the term 'substantially inelastic' shall refer to the ability of a headgear or material to resist stretching relative to the loads to which it may be subjected. When the expected loading forces are relatively low, the headgear or material may have greater elasticity because the load will not be sufficient to cause stretching. Conversely, if it is expected that the headgear and/or material will be subjected to high loading forces, then greater inelasticity will be required to resist stretching. Thus, the term "substantially inelastic" is taken within the context of the anticipated load on the headgear.

Certain embodiments described herein provide a nasal respiratory interface for an assembly for Obstructive Sleep Apnea (OSA) therapy. The interface can include a nasal pillow frame, yoke, and conduit connector that comprises a relatively small and low profile while improving patient comfort and functional effectiveness. For example, certain embodiments can enable the seal of the nasal pillow to be effectively secured in place on a patient, while keeping the sizes of the frame, yoke, and seal to a minimum. Accordingly, various embodiments described herein can advantageously reduce the size of the interface on the user's face to make the interface less obtrusive, and therefore more useable and attractive to patients. Although various embodiments described herein are described as an interface for nasal OSA therapy, the interface can also be used for treatment of other respiratory ailments and/or for delivery of pressurized breathing gases.

Figure 1:
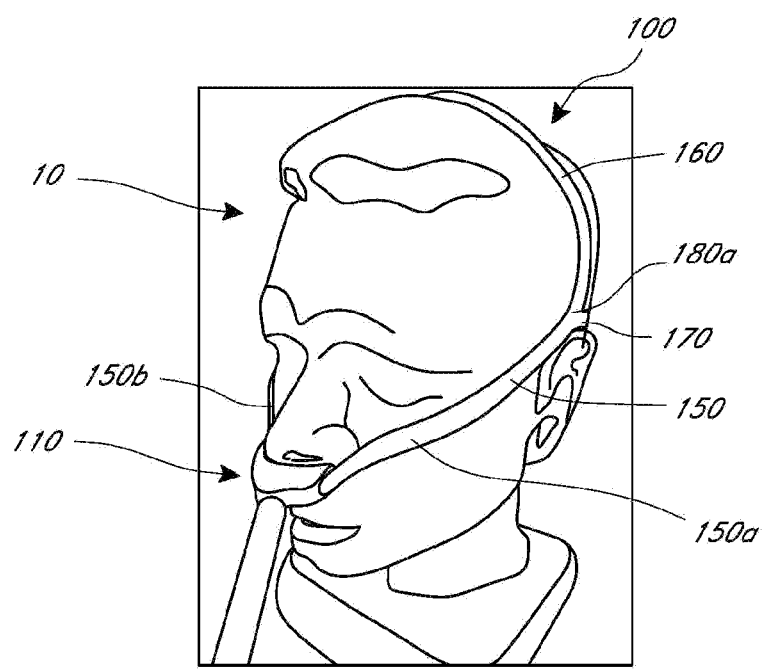
FIG. 1 is a perspective view of an embodiment of the headgear of the present disclosure being worn by a user.

Headgear:

FIG. 1 shows a non-limiting illustrative embodiment of a headgear 100 of the present disclosure in use in combination with a breathing apparatus 110. In some configurations, the headgear 100 is substantially inelastic at least along its length or in the direction of force applied to the headgear 100 by the breathing apparatus 110. The breathing apparatus 110 can deliver a gas (e.g., oxygen) to a user 10. The breathing apparatus 110 can be adapted to form a seal with at least a portion of the skin of the user 10, thereby increasing the efficacy of gas delivery to the user 10. For example, the illustrated breathing apparatus 110 is an under-nose interface or mask that includes one or more prongs, nozzles or pillows that can be inserted into the nostrils of the user 10, as illustrated in FIG. 1. In some variants, the breathing apparatus 110 can be a mask that fits over the nose or nose and mouth of the user 10.

As discussed above, the seal between the breathing apparatus 110 and the user 10 allows a positive pressure to build up within the breathing apparatus 110 as gas is delivered to the user 10. In the absence of a restraining force, this pressure can cause the breathing apparatus 110 to separate from the user 10. Separation of the breathing apparatus 110 from the user 10 would reduce or eliminate the efficacy of gas delivery from the breathing apparatus 110 to the user 10. In certain aspects, the headgear 100 of the present disclosure provides a semi-rigid, substantially inelastic, adjustable structure that is comfortable, easy to use, maintains contact between the breathing apparatus 110 and the user 10, and can be adjusted to the head size of the user 10.

The headgear 100 can include one or more straps configured to secure the breathing apparatus 110 to the user 10. In some configurations, the headgear 100 can have a front strap 150, an upper, top or crown strap 160, and a rear strap 170. In some variants, the headgear 100 can connect to the breathing apparatus 110 by a pair of front straps 150a,b that each extend across the cheeks of a user 10 up to a first junction 180a near the user's ear, at which point the headgear 100 can bifurcate into the crown strap 160 and the rear strap 170, as illustrated in FIG. 1. The first front strap 150a can extend posteriorly from the breathing apparatus 110 to the first junction 180a that joins the crown strap 160, the rear strap 170, and the front strap 150. The crown strap 160 and the rear strap 170 can run laterally across the top and back of the head of the user 10, respectively, joining a second front strap 150b at a second junction 180b (shown in FIG. 8). The first and second junctions 180a,b can be on substantially opposite sides of the head of the user 10. In some variants, the front strap 150 can be continuous. For example, the front strap 150 can be a unitary structure that joins first and second junctions 180a,b disposed on either end of the front strap 150, with the front strap 150 running anteriorly across the face of the user 10. The breathing apparatus 110 can connect to the unitary front strap 150 at an intermediate portion of the front strap 150 by a fastener (e.g., clip). The fastener can be intra-molded with, or over-molded onto, the front strap 150, as described below. In some configurations, the headgear 100 can be constructed from two or more portions that are connected to one another. For example, the headgear 100 can be constructed from two halves, which each half containing a front strap 150 (or portion thereof), a portion of the crown strap 160 and a portion of the rear strap 170. The halves (or other portions) can be joined by any suitable arrangement (e.g., sewing or welding) and, in some cases, can allow the headgear 100 to collapse or fold for easier storage or packaging.

Figure 2:
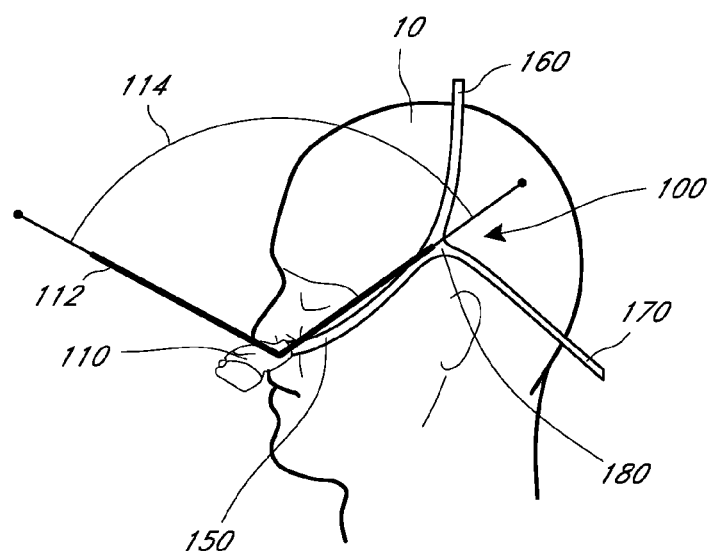
FIG. 2 is a side view of the headgear of FIG. 1 being worn by a user.

Referring to FIG. 2, the crown strap 160 and the rear strap 170 can form a halo-like structure that fits over the back of the user's head. The front strap 150 can link the halo-like structure to the breathing apparatus 110, thereby allowing the halo-like structure to resist the forces that tend to separate the breathing apparatus 110 from the user 10. The curvature of the front strap 150 can be adapted to avoid the eyes of the user 10, as illustrated in FIG. 2. The headgear 100 can pass along the cheeks or zygomatic bones of the user 10. The front strap 150 can bear on the cheeks to assist in resolving the forces of the seal between the breathing apparatus 110 and the user 10. The crown strap 160 can secure over the top of the user's head. The rear strap 170 can provide support around the ears and the back region of the head of the user 10.

As shown in FIG. 2, the headgear 100 can be adapted to align a contact or prong plane 112 of the breathing apparatus 110 with the lower surfaces of a user's nose. The headgear 100 can be adapted so that the prong plane 112 forms a prong-junction angle 114 with the junction 180 of the headgear 100. In the illustrated embodiment, the prong-junction angle 114 is about 116°. The prong-junction angle 114 can be between about 100° and about 135°. In some variants, the prong-junction angle 114 can be adjustable. The headgear 100 can be adapted so that the prong-junction angle 114 can be adjusted between about 100° and about 135°, thereby enabling the headgear 100 to maximize the seal or provide a sufficient seal of the breathing apparatus 110 on a wide variety of users 10.

Figure 3:
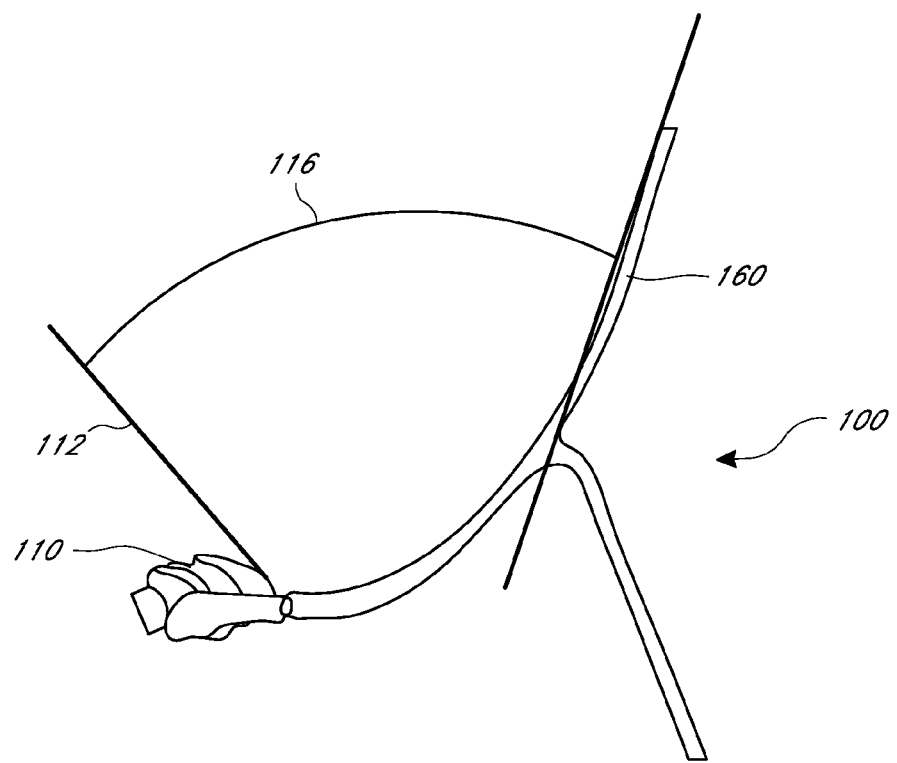
FIG. 3 is a side view of a strap arrangement that forms part of the presently disclosed headgear in combination with a user interface.

Referring to FIG. 3, the orientation of the prong plane 112 relative to the headgear 100 can be selected to allow effective use of the breathing apparatus 110. The prong plane 112 can form a prong-crown angle 116 with the crown strap 160. In the illustrated embodiment, the prong-crown angle 116 is between about 55-65° or is about 58°. In some configurations, the prong-crown angle 116 can be between about 30° and about 90° or between about 45° and about 75°. In some variants, the prong-crown angle 116 can be adjustable. The headgear 100 can be adapted so that the prong-crown angle 116 can be adjusted between about 30° and about 90°, thereby enabling the headgear 100 to maximize the seal or provide a sufficient seal of the breathing apparatus 110 on a wide variety of users 10.

Figure 4:
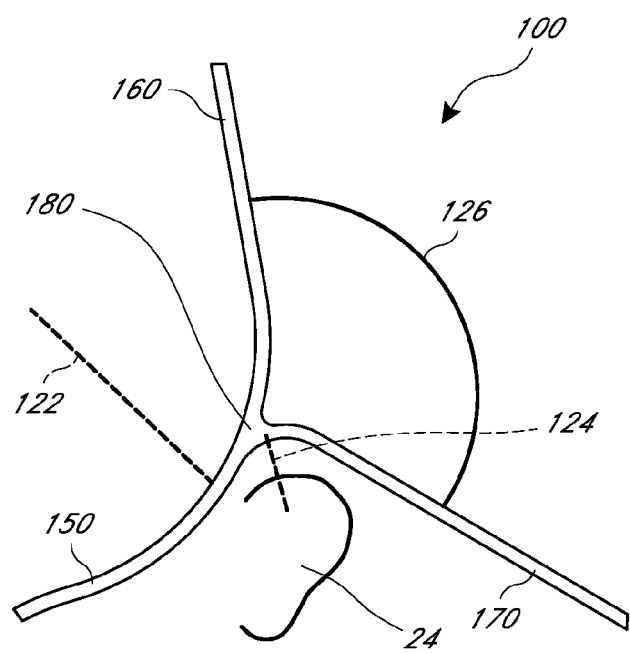
FIG. 4 is a side view of a strap arrangement that forms part of the presently disclosed headgear shown relative to a user.

As illustrated in FIG. 4, the headgear 100 can be designed to be a closed loop, with the curvatures of the straps from the junction 180 allowing continuation of the headgear 100 around the back of the user's head. For example, as illustrated in FIG. 4, the front strap 150 and the rear strap 170 can join the junction 180 along two tangential curves. The crown strap 160 and front strap 150 can form a continuous curve having a first radius of curvature 122. In the illustrated embodiment, the first radius of curvature 122 is about 113 mm. In some embodiments, the first radius of curvature 122 can be between about 55 mm and about 340 mm or can be between about 75 mm and about 250 mm. The front strap 150 can approach the junction 180 along the curve having the first radius of curvature 122. The crown strap 160 can extend away from the junction 180 along a tangent to the curve having the first radius of curvature 122.

The rear strap 170 can approach the junction 180 along a second radius of curvature 124. The headgear 100 can be designed to curve around the user's ear 24. For example, the rear strap 170 can curve over the top of the user's ear 24, as shown in FIG. 4. The curve of the straps can be selected to allow the headgear 100 to accommodate multiple head and ear sizes. The curve of the straps can provide ample room around the user's ear 24. In the illustrated embodiment, the junction 180 is positioned approximately over top of where the ear 24 joins the head of the user. However, the headgear 100 can be designed so that the junction 180 is anterior or proximal to the vertical plane passing through the point where the ear 24 joins the head.

The curve of the rear strap 170 around the ear 24 can be adapted to permit the ear 24 to be cleared by the headgear 100 and to maintain an angle sufficient to provide effective support around the back of the user's head. In the illustrated embodiment, the curve of the rear strap 170 around the ear 24 has a radius of curvature 124 of about 25 mm. In some variants, the radius of curvature 124 can be between about 10 mm and about 75 mm or can be between about 15 mm and about 50 mm. The curve of the rear strap 170 can be sized and shaped to allow the headgear 100 to accommodate about 95% of the relevant population of users 10. In some configurations, a headgear 100 having a radius of curvature 124 of about 25 mm alone or in combination with the particular positioning and angles between the straps 150, 160 and 170 disclosed herein can allow the headgear 100 to accommodate about 95% of the adult population.

As shown in FIG. 4, the headgear 100 can have a halo angle 126 between the crown strap 160 and the rear strap 170. The halo angle 126 can be selected to accommodate the head size range of about 95% of the population of users 10, providing adequate clearance for a range of user ear sizes while allowing the rigidity of the headgear 100 to be maintained. In the illustrated embodiment, the halo angle 126 is about 130°. In some variants, the halo angle 126 can be between about 90° and about 170° or can be between about 110° and about 150°. In some embodiments, the halo angle 126 can be adjustable.

Figure 5:
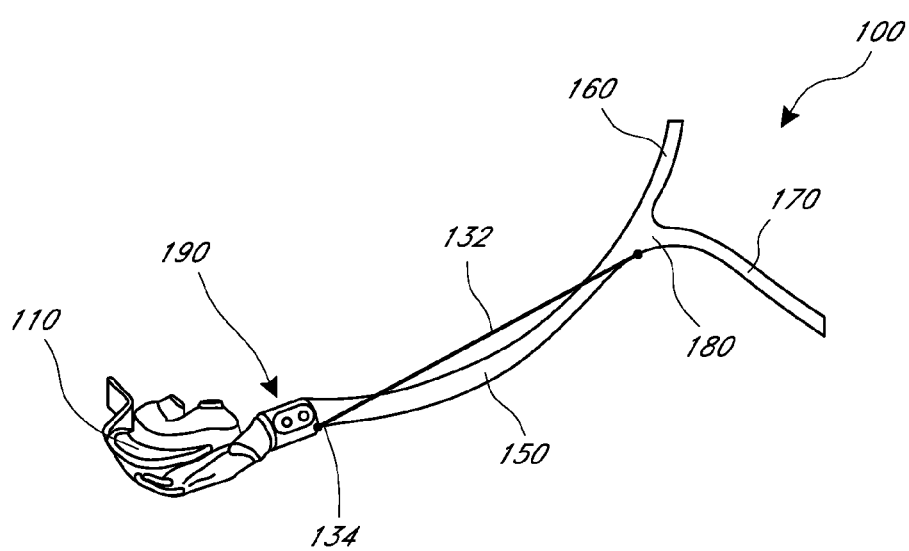
FIG. 5 is perspective view of a strap arrangement that forms part of the presently disclosed headgear.

Referring to FIG. 5, the headgear 100 can have a distance 132 between the junction 180 and the connection point 134 where the headgear 100 attaches to the breathing apparatus 110. In the illustrated embodiment, the distance 132 is about 115 mm. The distance 132 can be selected to accommodate the head size range of about 95% of the relevant or desired population of users 10. In some variants, the distance 132 can be between about 100 mm and about 130 mm. In some embodiments, the distance 132 can be adjustable. The front strap 150 can include, or attach to, a connector 190. The connector 190 can be a push or snap fit connector, or other suitable type of connector, that is configured to provide a detachable connection between the headgear 100 and the breathing apparatus 110. In some embodiments, the connector 190 may include an adjustment mechanism, wherein the adjustment mechanism provides a means of automatically or manually adjusting the distance 132.

Figure 6A:
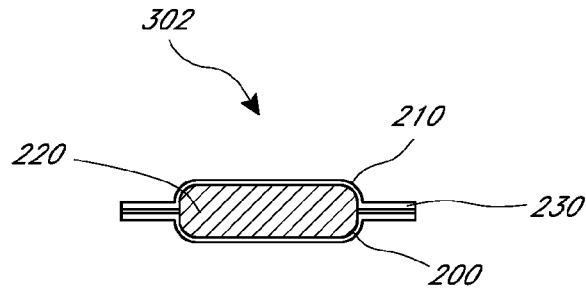
FIG. 6A is a cross-sectional view of a strap that can form a part of an embodiment of the presently disclosed headgear.
Figure 6B:
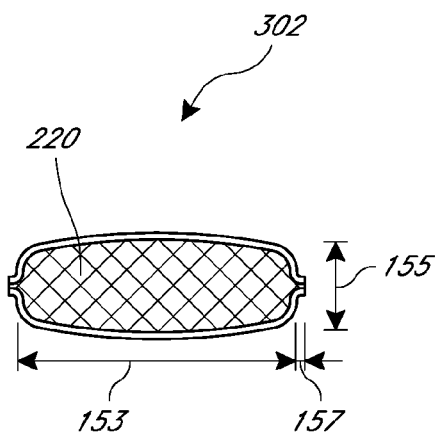
FIG. 6B is a cross-sectional view of a strap that can form a part of an embodiment of the presently disclosed headgear.
Figure 6C:
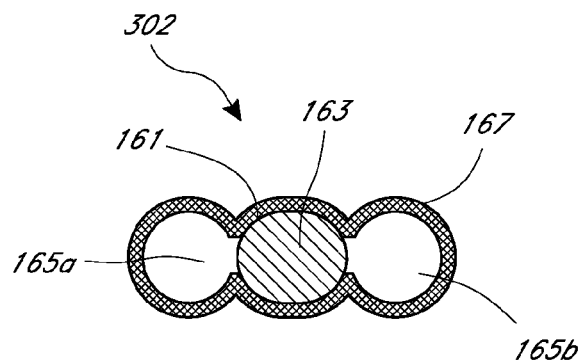
FIG. 6C is a cross-sectional view of a strap that can form part of an embodiment of the presently disclosed headgear.

Strap Intra-Molding:

The headgear 100 can be made to have sufficient rigidity to support the breathing apparatus 110 and maintain the seal between the breathing apparatus 110 and the user 10, while providing some flexibility to the headgear 100. For example, the headgear 100 can be made by molding a solid plastic, or any elastomer, to one or more layers of fabric or textile (e.g., unbroken loop fabric, also known as UBL fabric, if using hook and loop material adjustments, such as VELCRO adjustments). In some configurations, the molten plastic or elastomeric material is introduced into a space defined between two layers of fabric or textile material or within a fabric or textile tube and allowed to cool and harden. FIGS. 6A-6C depict cross-sectional views of different embodiments of a first headgear strap 302. A non-limiting exemplary embodiment of the composition of the headgear 100 is shown in FIG. 6A, which shows a cross-sectional view through any one or more of the front strap 150, the crown strap 160 and/or the rear strap 170. In some configurations, the front, crown, and rear straps 150, 160, 170 have a layered composition comprising an inner casing 200, an outer casing 210, and a core 220. In the illustrated arrangement, portions of the casings 200, 210 that are not in contact with the core 220 define casing edges 230. The inner casing 200 and the outer casing 210 comprise textile layers, wherein the inner casing 200 is configured to face or contact the user's head and the outer casing 210 is not and may be configured to face away from the user's head. The inner and outer casings 200, 210 may be made from the same or different textiles and can be configured to provide a soft and, in some embodiments, cushioned covering for the core 220.

In some configurations, the molding can be performed with the intention to press cut the outer shape of the first strap 302 after molding. For example, the strap 302 could be formed with substantial casing edges 230 to facilitate clamping and sealing of the layers by the mold tool (similar to the arrangement of FIG. 6A) and then the casing edges 230 could be trimmed to any desired degree, such as substantially completely trimmed as illustrated in FIG. 6B. The external dimensions for the headgear 100 and the possible size variations for one embodiment of the headgear 100 are shown in cross-section in FIG. 6B. The cross-section shows the rounded rectangular or ovular shape of the internal elastomer, and the fabric layer firmly connected around the outside. The first strap 302 can have a width 153, a depth 155, and an edge depth 157. In the illustrated embodiment, the width 153 is about 5 mm, the depth 155 is about 0.7 mm, and the edge depth 157 is about 1 mm. In some variants, the width 153 can be between about 5 mm and about 10 mm. In certain embodiments, the depth 155 can be between about 0.4 mm and about 2.7 mm or 3 mm. In some embodiments, the edge depth 157 can be between about 0.5 mm and about 3 mm. As shown in FIG. 6B, the cross-section of the first strap 302 can have a rounded, rectangular or ovular shape of the internal elastomer, and the fabric layer can be firmly connected around the outside of the first strap 302.

FIG. 6C depicts an embodiment of a first strap 302 having hollow portions. The first strap 302 can comprise three internal regions. A central region 161 can contain a plastic or elastomer core 163. The central region 161 can be surrounded by one or more peripheral regions 165a,b. In some configurations, the peripheral regions 165a,b can be hollow and can act as a soft edge. The external structure of the first strap 302 can be a knitted tube 167 that, in combination with the hollow peripheral regions 165a,b, creates soft edges. In some configurations, the peripheral regions 165a,b can be filled with a soft material, such as a gas, foam or gel, for example. The knitted tube 167 can be bonded to the internal elastomer 163, such as through a molding process as described above.

The width of the straps (e.g., the front strap 150, the crown strap 160, the rear strap 170) can be defined within a specific range to reduce or minimize the possibility of torsional forces twisting the straps and reducing structural integrity of the headgear 100, or causing discomfort to the user 10 as a result of the strap edges cutting into the face of the user 10. Furthermore, the core material thickness and fabric thickness can be selected to inhibit or prevent buckling and loss of tension in the headgear 100 due to weakness.

In some variants, the core 220 can comprise a relatively rectangular cross-section of a thermoform or thermoset plastic material that is configured to provide the headgear 100 with a 3D structure. The core 220 provides the foundation for the overall structure of the headgear 100. The plastic composition of the core 220 offers the benefits of a resilient structure that, in some configurations, is capable of maintaining a preformed shape while conforming somewhat to the individual cranial geometry of the user. Referring to FIG. 6B, the core 220 has a width 153 and a depth 155, wherein the width 153 is substantially greater than the depth 155. The cross-sectional geometry in combination with the material selection allows the headgear 100 to be flexible in a direction that is normal to the width 153 and relatively inflexible in a direction that is normal to the depth 155. This flexibility in one direction allows the headgear 100 to conform to a user's head while providing rigidity in a direction that stabilizes and minimizes dislodging of the breathing apparatus 110 on a user's face. The headgear 100 can be configured to permit or inhibit or substantially prevent twisting or torsion of the headgear 100 about a length direction of the strap 302 (into and out of the page in FIG. 6B).

As described above, the inner casing 200 and the outer casing 210 can be configured to be permanently bonded to the core 220 such that the core 220 is completely encased and the headgear 100 is formed from composite material. A casing edge 230 can be formed where the inner and outer casings 200, 210 meet. The inner and outer casings 200, 210 can be held together in close proximity by their bonds with the core 220. In some variants, the inner and outer casings 200, 210 may not be directly connected to each other at the casing edge 230. In the embodiment of FIG. 6A, the casing edge 230 is shown to be approximately at a midpoint of the depth D. In some embodiments, the casing edge 230 can be closer to one or other of the inner and outer casing 200, 210 side of the core 220.

The headgear 100 can be configured to be substantially inelastic as a result of material selection, for example. One or more elements of the composite material may provide the headgear 100 with substantially inelastic qualities. In one non-limiting illustrative embodiment of this disclosure, the core 220 can be made from a substantially inelastic material, such as polypropylene or nylon, for example but without limitation. In other embodiments, such as those in which the headgear 100 is expected to be subjected to low loading forces, the core 220 can be made of other materials, such as, but not limited to, thermoplastic elastomers (TPE) or silicone. In some embodiments, the core 220 may have a degree of elasticity and one or both of the inner casing 200 and/or the outer casing 210 can be substantially inelastic. The inclusion of a substantially inelastic material in the headgear 100 can be advantageous because the material can reduce or eliminate the likelihood of the headgear being stretched or pulled too far over the user's head. If the headgear 100 is pulled too far over the user's head, the breathing apparatus may not be effectively positioned to provide therapy and uncomfortable forces may be applied to the user's head, which can result in reduced compliance with the therapy.

The straps (e.g., the front strap 150, the crown strap 160, the rear strap 170) can be formed by injection molding the core 220 into a sleeve formed by the inner casing 200 and the outer casing 210 or formed by a single tubular casing. The casing edges 230 can be held together under compression within an injection molding tool. Such a structure forms a sealed sleeve that allows the plastic material of the core 220 to be injected into, and to thereby fill, all or a portion of the inside of the sleeve without creating significant flash at the casing edges 230. Example embodiments and methods of construction such a headgear are disclosed in Applicant's U.S. patent application Ser. No. 14/856,502, the entirety of which is incorporated by reference herein.

In some embodiments, there may be a textile casing on only one side of the headgear or the inner and outer casings 200, 210 may be made from differing materials. This may provide the headgear 100 with varied physical properties in different regions.

Adjustment Feature:

The headgear 100 can include one or more adjustment features that allow a length of the straps of the headgear 100 to be adjusted to accommodate the head of the user 10. The adjustment features of the headgear 100 are discussed in detail below. The headgear 100 can include adjustment features that are attached to the strap by an over-molding process. In some variants, at least a portion of the adjustment features are formed by and during intra-molding of the strap. In some variants, at least a portion of the adjustment features are attached to the strap after intra-molding the strap. Attachment of the adjustment features to the strap after intra-molding the strap can be done by suitable attachment methods known in the art (e.g., welding, stitching, gluing, etc.).

As mentioned above, the headgear 100 can be a semi-rigid structure and can include straps that are made from plastic molded onto a textile layer or within a space defined by one or more textile layers. In some variants, such a molded strap may be too rigid to fold back on itself, making the molded strap unsuitable for traditional loop-back adjustment features. The headgear 100 of the present disclosure can include adjustment features that allow the headgear 100 to be adapted to the user 10 when traditional loop-back adjustment features cannot be used due to the semi-rigid nature of the headgear 100. In some variants, the headgear 100 can include semi-rigid straps that overlap one another. The overlapping portions of the semi-rigid, molded straps can be designed to contact or push against one another, thereby creating a frictional force between the straps that resists the overlapping regions moving relative to one another.

Figure 7:
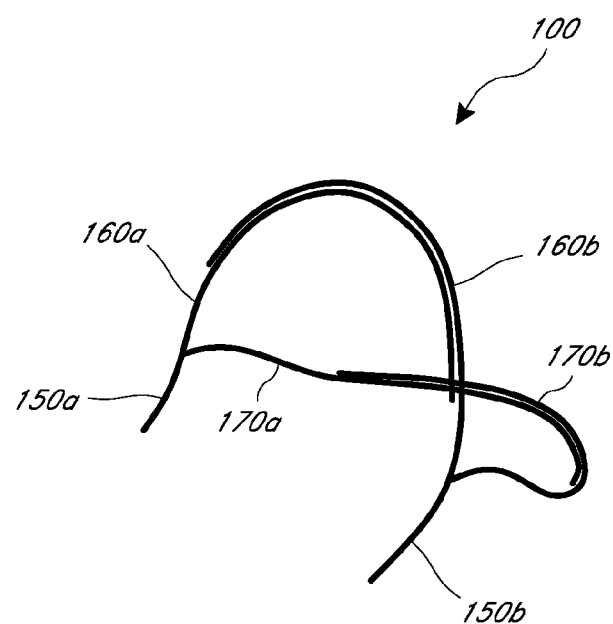
FIG. 7 is a perspective view of another embodiment of the headgear of the present disclosure.

FIG. 7 depicts a non-limiting, illustrative embodiment of the headgear 100. As shown in the illustrative embodiment, the headgear 100 can include straps that overlap with one another. The headgear 100 can include a right crown strap 160a that at least partially overlaps with a left crown strap 160b (with the terms "right" and "left" being in reference to a user 10 wearing the headgear 100). The headgear 100 can be adjusted by sliding the right crown strap 160a relative to the left crown strap 160b. For example, to accommodate a user 10 with a large head, the right and left crown straps 160a,b can be moved in the lateral direction so that the region of overlap between the right and left crown straps 160a,b is reduced. To accommodate a user 10 with a small head, the right and left crown straps 160a,b can be moved in the medial direction so that the region of overlap between the right and left crown straps 160a,b is increased.

The headgear 100 can include a right rear strap 170a that at least partially overlaps with a left rear strap 170b. The headgear 100 can be adjusted by sliding the right rear strap 170a relative to the left rear strap 170b. For example, to accommodate a user 10 with a large head, the right and left rear straps 170a,b can be moved in the lateral direction so that the region of overlap between the right and left rear straps 170*a,b* is reduced. To accommodate a user 10 with a small head, the right and left rear straps 170*a,b* can be moved in the medial direction so that the region of overlap between the right and left rear straps 170*a,b* is increased.

Figure 8A:
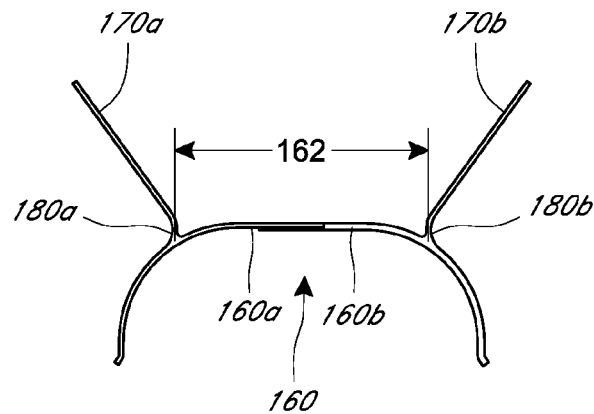
FIG. 8A is a top view of the headgear of FIG. 7 in a first adjustment position of a crown strap portion.
Figure 8B:
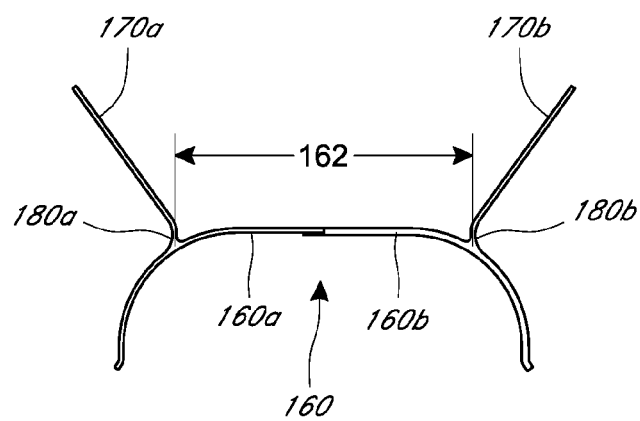
FIG. 8B is a top view of the headgear of FIG. 7 in a second adjustment position of the crown strap portion.

Referring to FIGS. 8A-8B, the headgear 100 can have a crown strap 160 that has an adjustable length 162. The length 162 of the crown strap 160 can be defined as the distance between the right and left junctions 180*a,b* of the head gear 100. In FIG. 8A, the right and left crown straps 160*a,b* have been moved in the medial direction so that the length 162 of the crown strap 160 is at its minimum length. In other words, the right and left crown straps 160*a,b* have been moved to their position of greatest overlap with one another. In the illustrated embodiment, the length 162 of the crown strap 160 has a minimum length of about 260 mm. In some variants, the length 162 of the crown strap 160 has a minimum length of between about 250 mm and about 270 mm.

In FIG. 8B, the right and left crown straps 160*a,b* have been moved in the lateral direction so that the length 162 of the crown strap 160 is at its maximum length. In other words, the right and left crown straps 160*a,b* have been moved to their position of least overlap with one another. In the illustrated embodiment, the length 162 of the crown strap 160 has a maximum length of at least about 380 mm. In some variants, the length 162 of the crown strap 160 has a maximum length of at least between about 370 mm and about 390 mm. The embodiment of the headgear 100 depicted in FIGS. 8A-8B can provide a crown strap adjustment of at least about 120 mm. In some variants, the headgear 100 can have a crown strap adjustment range of at least about 140 mm.

Figure 9A:
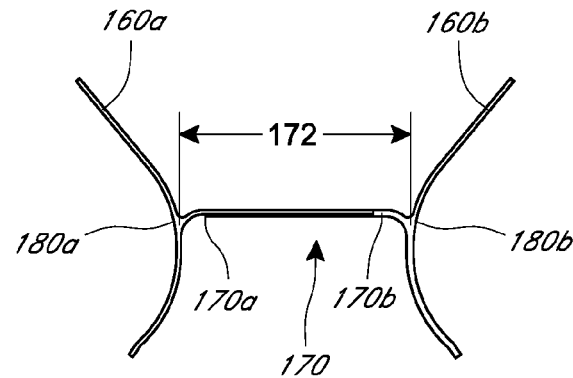
FIG. 9A is a rear view of the headgear of FIG. 7 in a first adjustment position of a back strap portion.
Figure 9B:
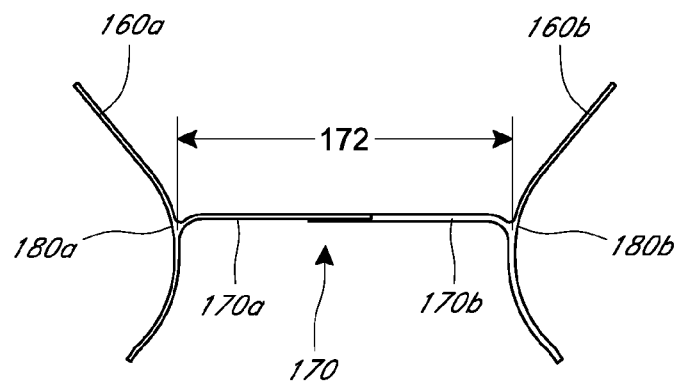
FIG. 9B is a rear view of the headgear of FIG. 7 in a second adjustment position of the back strap portion.

Referring to FIGS. 9A-9B, the headgear 100 can have a rear strap 170 that has an adjustable length 172. The length 172 of the crown strap 170 can be defined as the distance between the right and left junctions 170*a,b* of the head gear 100. In FIG. 9A, the right and left rear straps 170*a,b* have been moved in the medial direction so that the length 172 of the rear strap 170 is at its minimum length. In other words, the right and left rear straps 170*a,b* have been moved to their position of greatest overlap with one another. In the illustrated embodiment, the length 172 of the rear strap 170 has a minimum length of about 240 mm. In some variants, the length 172 of the crown strap 170 has a minimum length of between about 230 mm and about 260 mm.

In FIG. 9B, the right and left rear straps 170*a,b* have been moved in the lateral direction so that the length 172 of the crown strap 170 is at its maximum length. In other words, the right and left crown straps 170*a,b* have been moved to their position of least overlap with one another. In the illustrated embodiment, the length 172 of the rear strap 170 has a maximum length of at least about 360 mm. In some variants, the length 172 of the rear strap 170 has a maximum length of at least between about 350 mm and about 370 mm. The embodiment of the headgear 100 depicted in FIGS. 9A-9B can provide a rear strap adjustment of at least about 120 mm. In some variants, the headgear 100 can have a rear strap adjustment range of at least about 140 mm.

In some embodiments, the smallest crown length the headgear 100 is intended to fit is 260 mm, and the smallest back arch intended to be fit is 240 mm. The headgear 100 can be designed so that the greatest strap overlap position will therefore fit these smallest desired head sizes, thereby reducing or minimizing the chance the user 10 will over tighten the headgear 100. In some variants, the largest crown length intended to be fit is 380 mm and the largest back arch intended to be fit is 360 mm. The largest position of the headgear 100 will therefore be at least large enough to accommodate this range.

In some cases, the straps may be too rigid to overlap one another on the curved sections near the junctions 180*a,b*. The straps can be designed to overlap one another only on the straight portion of the straps. For example, the right crown strap 160*a* may have a curve distance of 65 mm, with the curve distance being defined as the distance from the right junction 180*a* to the straight section of the right crown strap 160*a*. The left crown strap 160*b* may also have a curve distance of 65 mm. In such a case, the distance of the straight section of the crown strap 160 would be about 130 mm (260 mm−2*65 mm). The right and left rear straps 170*a,b* can each have a curve distance of 27 mm, giving the rear strap 170 a straight section having a length of 186 mm (240 mm−2*27 mm). The aforementioned embodiments are intended to be illustrative and non-limiting. The curve distances of the crown strap 160 and of the rear strap 170 can be changed as desired. Moreover, the right curve distances need not be equal in length to the left curve distances.

Figure 10A:
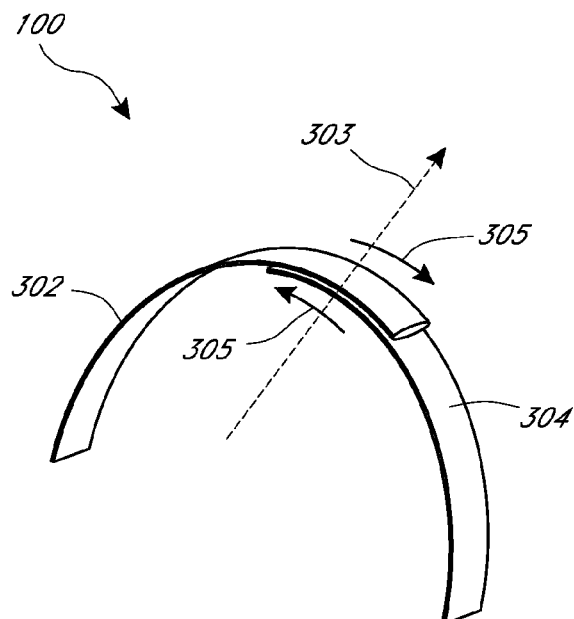
FIG. 10A is a perspective view of an embodiment of a size adjustment system for a headgear of the present disclosure.

FIG. 10A depicts an embodiment of an adjustment feature that uses frictional forces between the straps to resist the straps from moving relative to one another. A first strap 302 can overlap a second strap 304. As described above, the first and second straps 302, 304 can be intra-molded to form a strap having a semi-rigid core and a textile or fabric outer layer. The semi-rigid, overlapping first and second straps 302, 304 can push against one another to generate a compressive force between the first and second straps 302, 304. For example, referring to FIG. 10A, the first strap 302 can be pulled radially outward (in the direction of the dashed line 303) from its at-rest position and slid over the second strap 304, which is displaced radially inward from its at-rest position. Accordingly, a compressive force is created between the first and second straps 302, 304 because the first strap 302 is forced radially outward from its at-rest position by the second strap 304, while the second strap 304 is forced radially inward from its at-rest position by the first strap 302. The first and second straps 302, 304 can include an outer layer of material (e.g, fabric) that enhances the frictional forces between the first and second straps 302, 304. In the illustrated embodiment, the user's head would be radially inward of the second strap 304. In other words, the second strap 304 can be interposed between the first strap 302 and the user's head.

The headgear 100 can be adjusted by repositioning the first and second straps 302, 304 relative to one another. The first and second straps 302, 304 can be repositioned by relieving the compressive forces between the straps, moving the straps relative to each other in a tangential direction (as indicated by the solid arrows 305) and re-establishing the compressive force between the first and second straps 302, 304. For example, the first strap 302 can be pulled radially outward and/or the second strap 304 can be pushed radially inward to remove the compressive force between the first and second straps 302, 304. The first and second straps 302, 304 can then be moved tangentially relative to one another to change the amount of overlap between the first and second straps 302, 304. The compressive force between the first and second straps 302, 304 can then be restored by releasing the first and second straps 302, 304 so that the first strap 302 returns to pressing radially inward on the second strap 304, and the second strap 304 returns to pressing radially outward on the first strap 302. Alternatively, a force sufficient to overcome the frictional force developed between the straps 302, 304 can be applied to slide the straps 302, 304 relative to one another and adjust a combined length of the straps 302, 304.

Figure 10B:
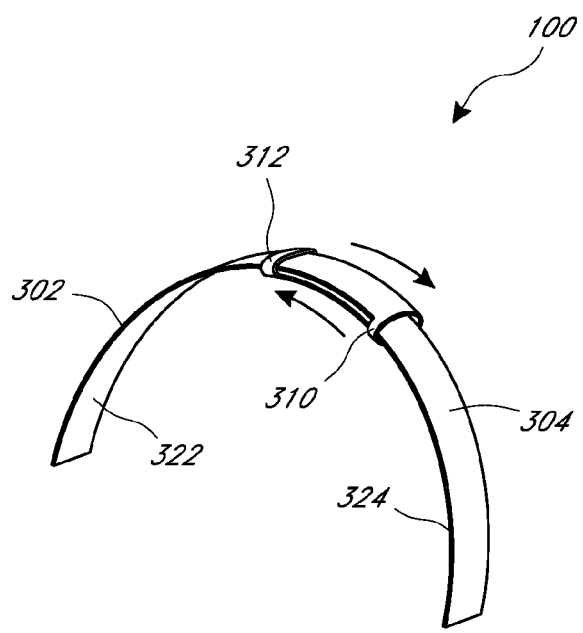
FIG. 10B is a perspective view of another embodiment of a size adjustment system for a headgear of the present disclosure.

FIG. 10B depicts an embodiment of an adjustment feature in which the first and second straps 302, 304 pass through a loop on the other strap. In the illustrative embodiment, the first strap 302 includes a first loop 310 on one end of the first strap 302. The second strap 304 includes a second loop 312 on one end of the second strap 304. The first and second loops 310, 312 can be oriented so that the openings of the first and second loops 310, 312 are parallel to the longitudinal axis of the strap of the headgear 100, as shown in FIG. 10B. The first strap 302 passes through the opening of the second loop 312, and the second strap 304 passes through the opening of the first loop 310. In some variants, the straps can be interlocked as illustrated by passing a free end of each strap through the loop of the other strap. For example, a first free end portion 322 of the first strap 302 can be passed through the second loop 312, while a second free end portion 324 can be passed through the first loop 310. After interlocking the straps through the first and second loops 310, 312, the first and second free end portions 322, 324 can then be connected to other components (e.g., straps, connectors) of the headgear 100. The loops 310, 312 can be of any suitable construction, such as relatively rigid (e.g., plastic) structures (FIG. 11A) or relatively soft or flexible (e.g., fabric) structures (FIG. 11B).

In the embodiment shown in FIG. 10B, the first strap 302 is bound to the top of the first loop 310 and sits above the second strap 304, with the second strap 304 passing through the first loop 310 of the first strap 302. The second strap 304 of the headgear 100 is bound to the bottom of the second loop 312 and sits below the first strap 302. In some variants, the adjustment feature can have only one strap that has a loop. For example, the first strap 302 can have a first loop 310 through which the second strap 304 passes, while the end of the second strap 304 that passes through the opening of the first loop 310 does not itself have a loop that surrounds the first strap 302. In some embodiments, the loop may be disposed on the strap at a location other than at the end of the strap. For example, the loop can be positioned in an intermediate portion of the strap, with the strap extending away from the loop in two opposite directions. In some variants, one or both straps can include more than one loop. The loops can be attached to the straps by over-molding the strap onto the loop or by other attachment methods known in the art (e.g., welding, stitching, gluing).

Figure 11A:
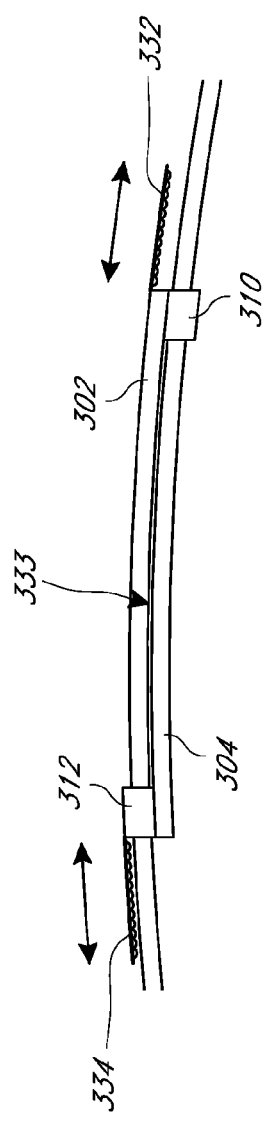
FIG. 11A is a side view of yet another embodiment of a size adjustment system for a headgear of the present disclosure.
Figure 11B:
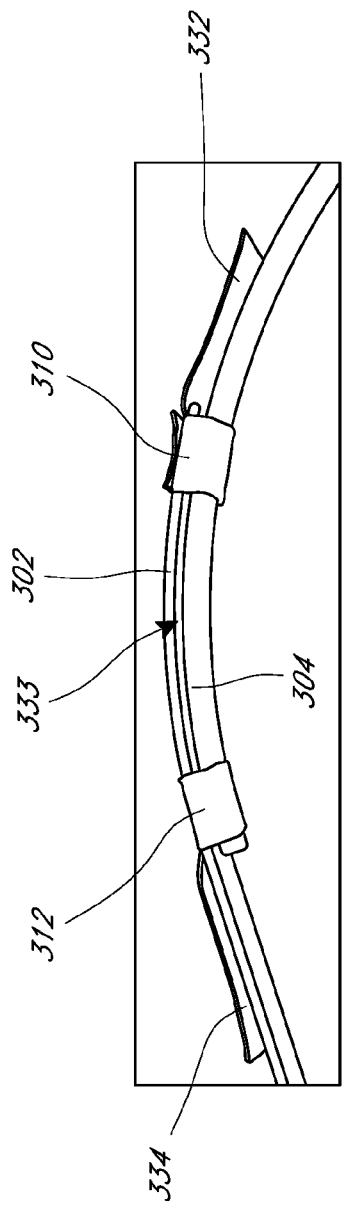
FIG. 11B is a side view of still another embodiment of a size adjustment system for a headgear of the present disclosure.

Referring to FIGS. 11A-B, the adjustment feature can include one or more tabs for applying force to adjust the position of the first and second loops 310, 312 and, thus, the straps 302, 304 with respect to each other. For example, the first strap 302 can be coupled to a first tab 332 and the second strap 304 can be coupled to a second tab 334. The first and second tabs 332, 334 can provide a grip point that facilitates pulling and moving the first and second straps 302, 304 relative to one another in a lateral direction, thereby increasing the overlap between the first and second straps 302, 304 and reducing the overall length of the strap. The user 10 can grip the first and second tabs 332, 334 and pull, tightening the strap to fit the head of the user 10. The frictional force between the straps 302, 304 can assist in maintaining the adjusted position of the first and second straps 302, 304. The first and second tabs 332, 334 can be pulled outwardly in opposite directions to tighten the headgear 100, and the non-overlapping portions of the first and second straps 302, 304 can be pulled outward to loosen the headgear 100.

In the embodiment shown in FIGS. 11A-B, the user's head would be radially inward of the first and second straps 302, 304. In other words, the first and second straps 302, 304 can be oriented so that the second strap 304 is between the user's head and the first strap 302 in the region where the first and second strap 302, 304 overlap. In the illustrated embodiment, the first and second tabs 332, 334 are positioned radially outward of an interface 333 between the overlapping portions of the first and second straps 302, 304. Accordingly, the first tab 332 can be positioned away from the first loop 310 such that the first strap 302 is between the first tab 332 and the first loop 310 in a thickness direction of the strap 302, while the second tab 334 can be connected to the second loop 312 such that the second loop 312 is between the second tab 334 and the second strap 304. In some variants, the first and second tabs 332, 334 can be rotated circumferentially about the interface 333 relative to the illustrated embodiment. For example, the first tab 332 in the illustrated embodiment can be positioned such that the connection point between the first tab 332 and the first strap 302 is approximately equidistant from the user's head as is the interface 333. In other words, rather than being on the top of the strap assembly as shown in FIG. 11B, the first and second tabs 332, 334 can be at the front or back of the respective strap, at the bottom of the strap, or at any other position around the circumference of the interface 333.

Figure 12:
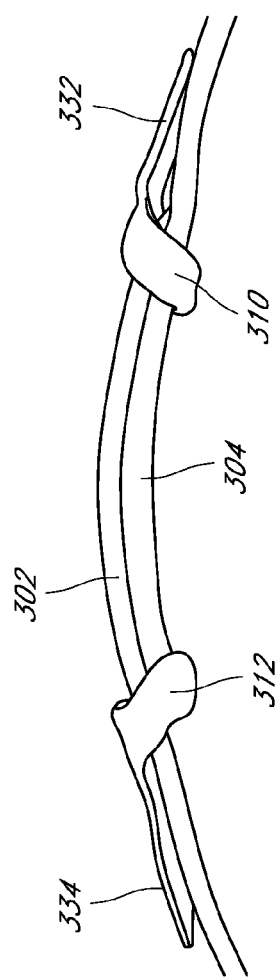
FIG. 12 is a side view of another embodiment of a size adjustment system for a headgear of the present disclosure.

Referring to FIG. 12, the first and second loops 310, 312 can be angled with respect to the perpendicular plane of the headgear and tabs 332, 334. Such an arrangement can reduce or avoid having the loops 310, 312 rock and dig into the straps 302, 304 when a user pulls on the tabs 332, 334 as a result of the tabs 332, 334 being off-center of the loops 310, 312. The loops 310, 312 and the tabs 332, 334 can be attached to the straps 302, 304 using RF welding, thereby reducing the thickness of the strap system and increasing the comfort of the headgear 100. Other suitable arrangements for attaching the loops 310, 312, tabs 332, 334 and straps 302, 304 to one another can also be used.

Referring to FIGS. 13A-C, in another configuration of an adjustment feature, the first strap 302 can include a flared end 373 having a keyhole 371. The keyhole 371 can have a slot 375 that extends from a center line of a circular opening 377, as shown in FIG. 13C. The keyhole 371 can be sized to receive and retain the second strap 304. For example, the second strap 304 can include a flared end 373' that can pass through the keyhole 371 in a width direction. After the flared end 373' passes through the keyhole 371, the second strap 304 can be rotated 90° so that the second strap 304 can rest in the central opening 377 of the keyhole 371, as shown in FIGS. 13A and 13B. The end of the second strap 304 can be fed through the keyhole 371 of the first strap 302 and secured in place at the correct size of the headgear 100. This strap design can be easily intra-molded and integrally formed, allowing for easy manufacture and assembly with only one molding tool needed for both sides of the headgear 100. In some variants, both straps 302, 304 can have a flared end 373, 373' having a keyhole 371, 371', as shown in FIGS. 13B and 13C. In some variants, only one end requires the keyhole 371. That is, only one strap 302, 304 can be passed through the keyhole 371, 371' of the flared end 373, 373' of the other strap 302, 304 or both straps 302, 304 can be passed through the keyholes 371, 371' of the flared ends 373, 373' of the opposite straps 302, 304. In the latter arrangement, the end opposite the flared end 373, 373' of at least one of the straps 302, 304 may initially be free (e.g., separate from the junction 170) so that it can be passed through the opening 377 and then attached to another portion of the headgear 100 (e.g., the junction 170). The combination of the slot 375 and the opening 377 can be slightly longer than the flared end 373 is wide. In order to assemble, the first strap 302 can be rotated in the perpendicular plane and fed through the keyhole 371. The central opening 377 of the keyhole 371 can be sized according to the strap width and, in some configurations, can be sized to have a snug fit with the strap width such that an adjustment position of the straps 302, 304 can be maintained via frictional or interference forces developed between the flared end 373, 373' and the respective strap 302, 304. In some variants, the first strap 302 with the keyhole 371 adjustment feature is not intended for a user to completely disassemble the first strap 302.

Figure 14:
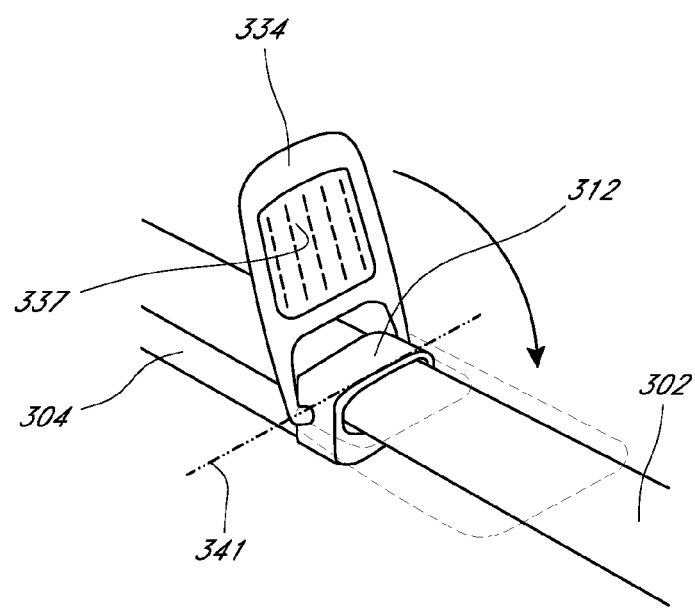
FIG. 14 is a perspective view of a securement tab that can be used with the presently disclosed size adjustment systems.
Figure 15A:
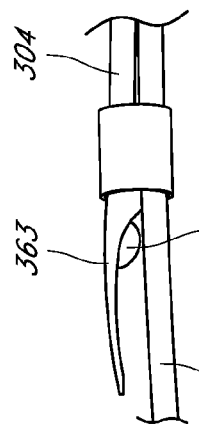
FIG. 15A is a perspective view of a securement tab that can be used with the presently disclosed size adjustment systems in a first, unfolded or secured position.
Figure 15C:
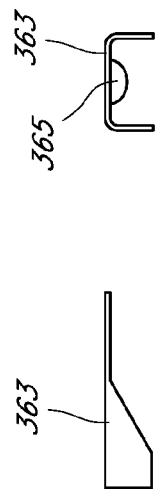
FIG. 15C is a side view of the securement tab of FIG. 15A in the unfolded position.
Figure 15E:
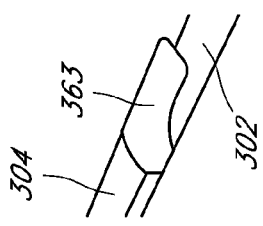
FIG. 15E is a front view of the securement tab of FIG. 15A in the unfolded position.
Figure 15G:
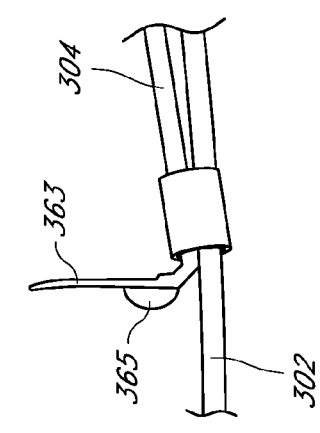
FIG. 15G is a side view of a modification of the securement tab of FIG. 15A in an unfolded position, wherein the securement tab includes an engagement portion.
Figure 15B:
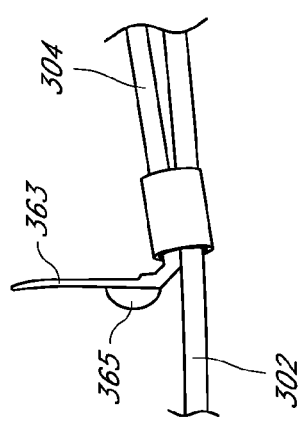
FIG. 15B is a perspective view of the securement tab of FIG. 15A in a second, folded or released position.
Figure 15D:
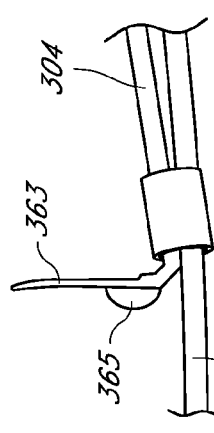
FIG. 15D is a side view of the securement tab of FIG. 15A in the folded position.
Figure 15F:
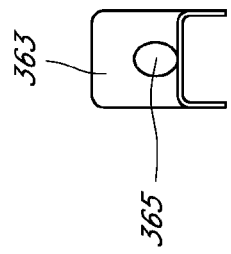
FIG. 15F is a front view of the securement tab of FIG. 15A in the folded position.
Figure 15H:
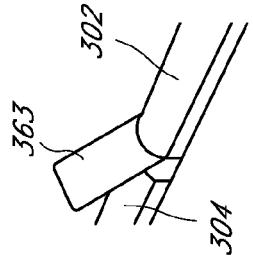
FIG. 15H is a side view of the securement tab of FIG. 15G in a folded position.

Referring to FIG. 14, the first and second tabs 332, 334 (which can be similar to those shown in FIG. 11A) can be adapted to help secure the position of the first and second straps 302, 304 relative to one another. Although the illustrative embodiment now described will be discussed in the context of the second tab 334, the first tab 332 could be similarly constructed. Referring to FIG. 14, the second tab 334 can include an adhesive member 337 (e.g., a hook portion of a hook-and-loop fastener) on a front surface of the second tab 334. The second tab 334 can rotate around an axis 341 that is parallel to the width of the second strap 304. The adhesive material 337 can adhere to the outer surface of the first strap 302 when brought into contact with the outer surface of the first strap 302 (as shown by the dashed lines). After the first and second straps 302, 304 are adjusted to their desired positions, the second tab 334 can be rotated about the axis 341 to bring the adhesive material 337 of the second tab 334 into contact with the outer surface of the first strap 302. The adhesive material 337 of the second tab 334 engages the outer surface of the first strap 302, thereby assisting in locking the specified measurement of the strap in place. The outer surface of the first strap 302 can be constructed from a loop portion of a hook-and-loop fastener or can include a loop portion attached to the strap 302. Other suitable arrangements to permit releasable coupling of the tab 334 to the strap 302 can also be used. To adjust the first and second straps 302, 304 to a different relative position, the second tab 334 can be moved up to disengage the adhesive material 337 from the outer surface of the first strap 302, thereby allowing the first and second straps 302, 304 to be moved relative to one another. The second tab 334 can be configured so that when the second tab 334 is moved up to the disengaged position, the second tab 334 remains in the upward position until the second tab 334 is deliberately moved down. In some variants, the first tab 332 can be similarly constructed as the second tab 334 so that the headgear 100 has first and second tabs 332, 334 with adhesive surfaces 337 that engage the outer surface of the opposing strap 302, 304.

FIGS. 15A-H depict a securing tab 363 that is configured to fold when moving between a first position and a second position. The illustrated securing tab 363 is also configured to concentrate frictional forces at a localized point, which can be used alone or in combination with frictional forced developed by the overlapping length of the first strap 302 and the second strap 304. However, the foldable tab 363 can be used without the frictional concentrator and the frictional concentrator can be used with other tab designs, such as those disclosed herein. The foldable tab 363 can be fabricated using a flexible material, and shaped so that at its fixed end, the tab is wider than the first strap 302, and wrapped around the edge of the first strap 302 so that the tab 363 is curved over the top and extends along the sides of the first strap 302. In some configurations, the tab 363 can comprise a loop that encircles the first strap 302 and the second strap 304 in a manner similar to the loops 310, 312 disclosed herein. In some configurations, the foldable tab 363 can be constructed from a relatively stiff fabric or textile material, which allows the tab 363 to be folded to a released position (FIGS. 15B, 15D, 15F, 15H) but also allows the tab 363 to transfer force to the strap 302 when in the unfolded or secured position (15A, 15C, 15E, 15G).

The tab 363 can include a protrusion 365 bonded or otherwise affixed to the underside of the tab 363 so that when the tab 363 is flipped down to be parallel with the first strap 302, the protrusion 365 is in contact with the headgear first strap 302, creating a concentration point for frictional forces. This solves the behavior encountered with the above designs where, for larger head sizes (and corresponding lower strap overlap surface area) the headgear could come loose due to lower frictional forces being developed between the straps 302, 304. In addition or in the alternative, the tab 363 could also utilize a hook-and-loop or other releasable fastener to allow the tab 363 to be secured to the strap 302. In addition, the protrusion 365 could be provided on other types of tabs, as well, such as those disclosed herein.

Figure 16A:
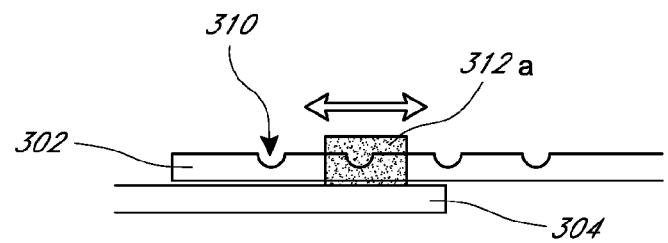
FIG. 16A is a side view of a size adjustment system for a headgear of the present disclosure.
Figure 16B:
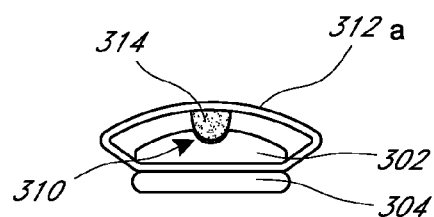
FIG. 16B is an end view of the size adjustment system of FIG. 16A in a secured position.
Figure 16C:
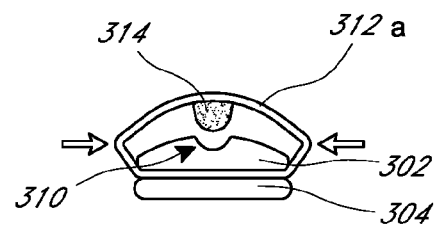
FIG. 16C is an end view of the size adjustment system of FIG. 16A in a released position.

Referring to FIGS. 16A-C, the adjustment feature can be adapted to allow the straps to be adjusted to discrete positions. For example, first strap 302 can have one or more notches 310 that are longitudinally spaced apart from one another along the first strap 302. A second strap 304 can include a resilient member, such as a resilient tube 312a. The resilient tube 312a can be attached to the second strap 304 by any suitable arrangement, such as by over-molding the second strap 304 and the resilient tube 312a one onto the other. In some variants, the resilient tube 312a can be attached to the second strap 304 by welding, gluing, stitching, or other methods known in the art.

The first strap 302 can pass through the resilient tube 312a of the second strap 304. The resilient tube 312a can include an internal bulb 314 or other type of protrusion. As shown in FIG. 16B, the resilient tube 312a can have a locked position in which the internal bulb 314 engages the notch 310, thereby inhibiting or preventing the first and second straps 302, 304 from moving relative to one another in response to normal or expected forces. As shown in FIG. 16C, the resilient tube 312a can have an unlocked position in which the internal bulb 314 is removed from the notch 310, thereby allowing the first and second straps 302, 304 to be moved relative to one another. In some variants, the resilient tube 312a can be moved from the locked position to the unlocked position by applying pressure to the sides of the resilient tube 312a, as depicted by the arrows in FIG. 16C, thereby causing the resilient tube 312a to bend away from the first strap 302 and withdraw the internal bulb 314 from the notch 310. A user can adjust the size of the headgear 100 by unlocking the internal bulb 314 from the notch 310 (see FIG. 16C), sliding the first strap 302 relative to the second strap 304 (see FIG. 16A) to adjust the straps to the desired position, and locking the internal bulb 314 to the notch 310 to maintain the position of the first and second straps 302, 304. The resilient tube 312a can position the bulb 314 into the notch in a relaxed position of the tube 312a such that moving the resilient tube 312a to the locked position can involve the user releasing the sides of the resilient tube 312a. This adjustment feature can allow a stepwise alteration to the length of the relevant headgear strap.

Referring to FIG. 17A, the first and second straps 302, 304 can be aligned next to each other as shown in the illustrated embodiment. By aligning the straps 302, 304 next to one another rather than on top of another, the overall thickness of the first and second straps 302, 304 along the overlapping portion can be reduced, which can increase the comfort of the headgear 100 for the user. The first strap 302 can include a sliding loop 391 that slides on the same plane as the first strap 302 and surrounds the second strap 304, as shown in FIG. 17A. The second strap 304 can include a sliding loop 391' that slides on the same plane as the second strap 304 and surrounds the first strap 302. The loops 391, 391' can be open loops that define an access slot or opening configured to allow the strap 302, 304 to pass therethrough into the opening of the loop 391, 391'. In some configurations, the loops are then closed, such as by securing the ends of each of the open loops 391, 391' to its respective strap 302, 304 after the other strap 302, 304 has been positioned within the loop 391, 391'. In some configurations, the loops 391, 391' can be constructed as closed loops and the free ends (opposite the loops 391, 391') of the straps 302, 304 can be passed through the closed loop of the other strap 302, 304.

Referring to FIG. 17B, the sliding loop 391 of one or both of the first strap 302 and the second strap 304 can have a tab 393 for adjusting the overall length of the straps 302, 304. The tabs 393, 393' can be centrally located with regard to the width and/or thickness of the first and second straps 302, 304. The centrally located tabs 393, 393' can be combined with the reduced thickness of the first and second straps 302, 304 to reduce the force on each of the straps 302, 304 when the tabs 393, 393' are pulled, resulting in a potential smoothening of the adjustment (e.g., tightening) motion for the headgear 100. In FIG. 17B, the loops 391, 391' are molded plastic members, which can be molded separately and then attached to the straps 302, 304 or can be overmolded directly onto the straps 302, 304, such as by a process as described herein with respect to FIGS. 21-27 or elsewhere. For example, the tab 393' can be attached to the loop 391' at location 395.

Referring to FIG. 18A, the headgear 100 can include a sleeve 500 that covers the overlapping sections of the first and second straps 302, 304. The sleeve 500 can prevent a user's hair from getting tangled in the overlapping portions of the straps 302, 304. The sleeve 500 can be attached to the first and second straps 302, 304 by any suitable process, such as by overmolding the sleeve 500 onto the straps 302, 304, as discussed in more detail below. In some variants, the sleeve 500 can have a first endcap 502 that is attached to one end of the first strap 302. The first endcap 502 can have an opening 512 through which the second strap 304 passes, thereby allowing the first endcap 502 to move along the second strap 304, as shown in FIG. 18B. In some variants, a shim can be placed over the second strap 304 at the time overmolding the sleeve 500 onto the first strap 302, thereby creating a lining to the opening 512 of the first endcap 502 that allows the second strap 304 to slide through the opening 512 of the first endcap 502.

The sleeve 500 can have a second endcap 504 that is attached to the second strap 304. The second endcap 504 can have an opening 514 through which the first strap 302 passes, thereby allowing the second endcap 504 to move along the first strap 302, as shown in FIG. 18B. In some variants a shim can be placed over the first strap 302 at the time of overmolding the sleeve 500 onto the second strap 304, thereby creating a lining to the opening 514 of the second endcap 504 that allows the first strap 302 to slide through the opening 514 of the second endcap 504.

In some configurations, the sleeve 500 can be resilient or elastic; however, in other configurations, the sleeve 500 may not tend to return to any particular length. The sleeve 500 can have a relaxed state (shown in FIG. 18A) and a stretched state (shown in FIG. 18B). The sleeve 500 can be easily expandable and compressible to accommodate a wide range of adjustment to the headgear 100. In some variants, the length of the sleeve 500 at its most extended state is about 120 mm. In some embodiments, the length of the sleeve 500 at its most extended state is within a range of about 100 mm to about 140 mm. The sleeve 500 can allow restriction of the maximum and minimum extension and contraction of the first and second straps 302, 304 in accordance with the straight geometry of each strap 302, 304. Each endcap 502, 504 can be overmolded to the sleeve 500 and the straps 302, 304, providing a clean, effective finish to the headgear 100 and reducing the manufacturing steps. In some variants, the sleeve 500 can be a braided material. In some variants the sleeve 500 can be an unbraided soft tube. The concept of the sleeve 500 is not limited to a braid. The material of the sleeve 500 can be a braided tube with the orientation of the braids configured to allow extension of the tube in the longitudinal direction. The braid filaments will form an angle with the longitudinal axis of the sleeve 500. In the extended state, the angle of the filaments relative to the longitudinal axis of the sleeve will be smaller than when the sleeve is in its relaxed state. A desirable behavior of the braided sleeve in at least some configurations is that the extension of the sleeve 500 can be self-limiting. The braid has a maximum point that it may extend. This may inhibit or prevent a user from overtightening the headgear 100.

Figure 19A:
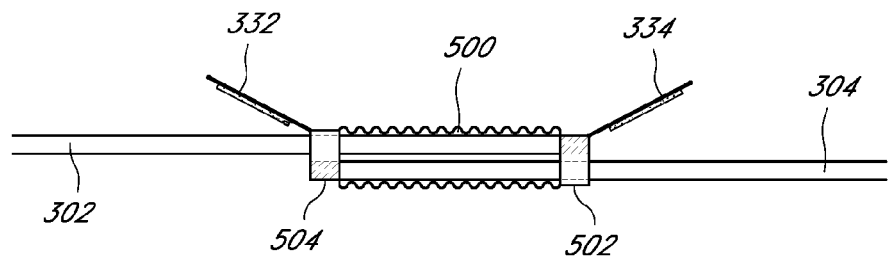
FIG. 19A is a side view of another size adjustment system having a braided sleeve for use with the presently disclosed headgear.
Figure 19B:
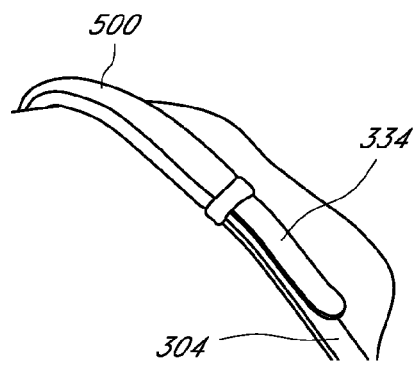
FIG. 19B is a perspective view of a headgear incorporating the size adjustment system of FIG. 19A being worn by a user.
Figure 20A:
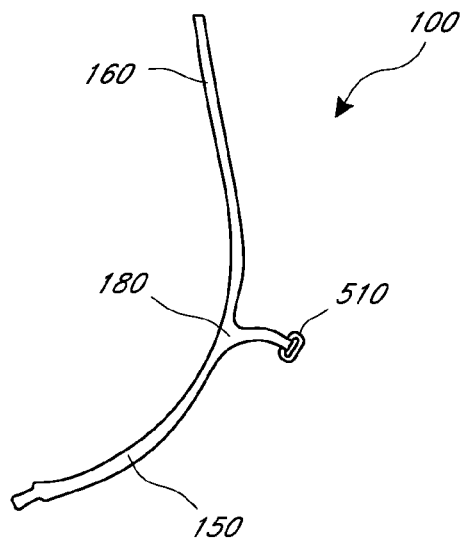
FIG. 20A is a side view of a strap arrangement that forms part of a headgear of the present disclosure.
Figure 20B:
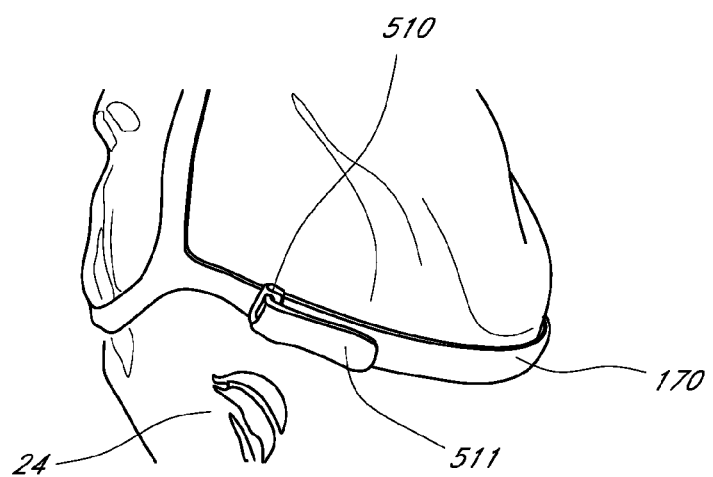
FIG. 20B is a perspective view of a headgear incorporating the strap arrangement of FIG. 20A being worn by a user.

Referring to FIG. 19A, the sleeve 500 can include tabs 332, 334 for providing grip points for adjusting the straps 302, 304, as discussed above. In some variants, the tabs 332, 334 can include VELCRO® that secures the tabs 332, 334 to the opposing first or second strap 302, 304 to help keep the sleeve 500 in an extended state after the straps 302, 304 have been adjusted to a desired length, as shown in FIG. 19B Referring to FIGS. 20A and 20B, the headgear 100 can include a buckle 510 and a rear strap 170. The rear strap 170 can be made of a material such as Breath-o-prene. In some cases, the rear strap 170 can be elastic. Once fitted, the elasticity of the rear strap 170 can allow the user to put on and remove the headgear 100 without the need to make any other adjustments other than to the crown strap 160, which preferably can be done only as an initial adjustment. The buckle 510 can be integrally formed (e.g., intra-molded) at the end of the portion of the strap that extends from the junction 180, as shown in FIG. 20A. The buckle 510 can be used with a hook-and-loop fastener adjustment system in which an extension 511 of the rear strap 170 passes through the buckle 510 and then folds back to attach to the surface of the rear strap 170. In some variants, the headgear 100 can include a buckle 510 and hook-and-loop fastener adjustment mechanism on both sides of the headgear 100. Alternatively, the buckle 510 and VELCRO® adjustment mechanism can be on only one side of the headgear 100. In some variants, the buckle 510 is positioned slightly behind the user's ear 24 to improve comfort of the headgear 100 when the user is sleeping on the user's side.

Overmolding:

As mentioned above, at least a portion of the adjustment features of the headgear 100 can be overmolded onto a strap of the headgear 100. An illustrative embodiment of an overmolding process for attaching the sleeve 500 to the first and second straps 302, 304 will now be discussed.

Figure 21:
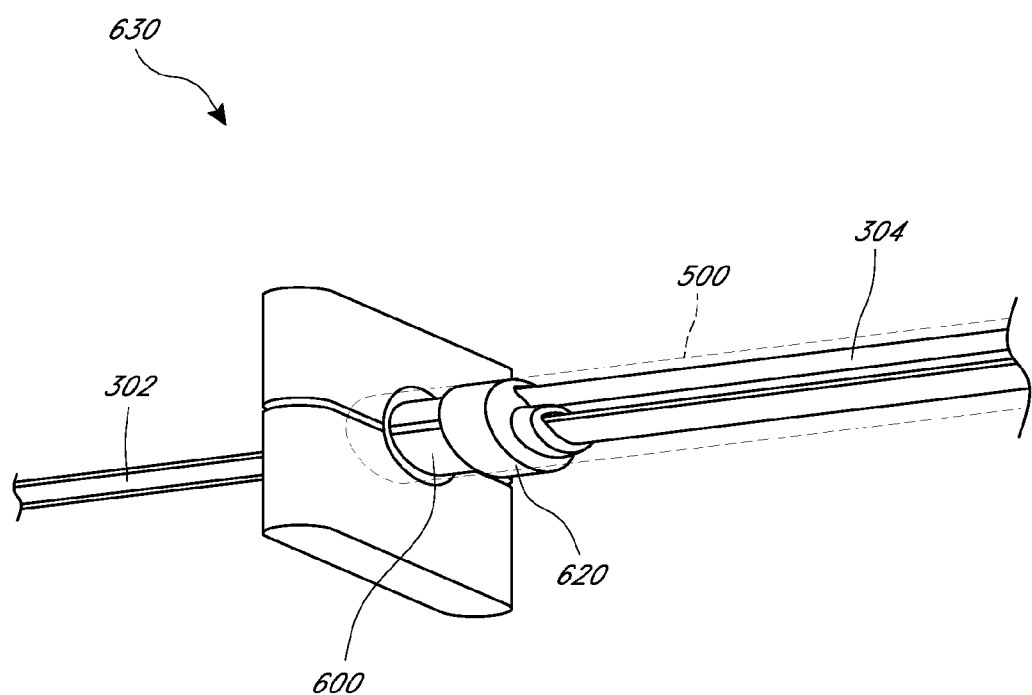
FIG. 21 is a perspective view of a size adjustment system, such as the size adjustment system of FIGS. 18A and 18B or FIGS. 19A and 19B, in combination with a separator tool and a clamp used to form the size adjustment system.

FIG. 21-27 depict an exemplary overmolding process for producing an adjustment arrangement comprising a sleeve 500 that can elongate or contract longitudinally as the straps 302, 304 are moved relative to one another, as discussed above, for example, with respect to FIGS. 18A-B. Referring to FIG. 21, the sleeve 500 is shown as a dashed line for the sake of clarity so that the molding tools and straps 302, 304 can be seen. The illustrated embodiment shows a method for making the second endcap 504 (shown in FIG. 18A), which can be attached to the second strap 304 and is configured to slide over the first strap 302. To mold the second endcap 504, the first strap 302 can be passed through a separator 600 that can prevent the molded plastic 620 from bonding to the first strap 302. The end of the second strap 304 can be positioned adjacent to the separator 600 and can be external of the separator, allowing the molded plastic 620 to bond to a portion of the second strap 304, as described below. In some embodiments, the first strap 302 can be passed through the separator 600, and then the sleeve 500 and the separator 600 can be assembled into a clamp 630 that holds the sleeve 500 and separator 600 in place during molding. After molding is complete, the clamp 630 can be removed and the separator 600 can be withdrawn from the molded plastic 620 and sleeve 500, thereby producing an endcap 504 comprising molded plastic 620 that is bonded to the sleeve 500 and the second strap 304 but not bonded to the first strap 302. This process is discussed in more detail below.

Figure 22A:
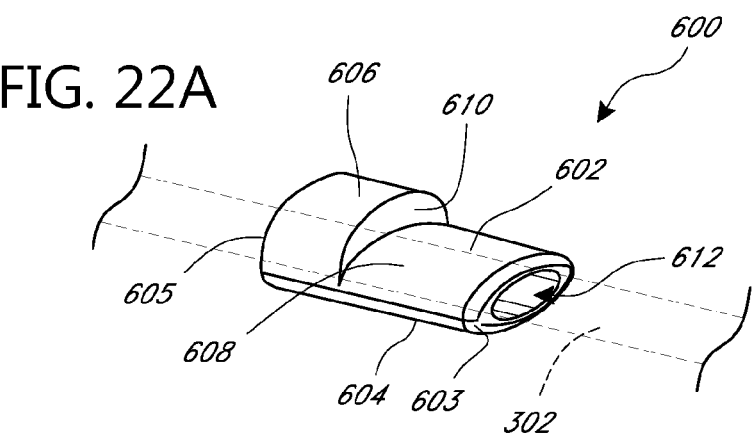
FIG. 22A is a perspective view of the separator tool of FIG. 21.

Referring to FIG. 22A, the separator 600 can have a top surface 602, a bottom surface 604, a rear portion 606, and a front portion 608. The rear portion 606 can be held by the clamp 630 during overmolding. The top surface 602 of the front portion 608 of the separator 600 can be recessed relative to the top surface 602 of the rear portion 606, thereby creating an abutment 610, as shown in FIG. 22A. The separator 600 can have a channel 612 that communicates with a front face 603 and a rear face 605 of the separator 600. During overmolding, the rear face 605 faces away from the sleeve 500. The channel 612 can be sized to receive a first strap 302. The first strap 302 can pass through the channel 612 and extend beyond the front and rear faces 603, 605 of the separator 600.

Figure 22B:
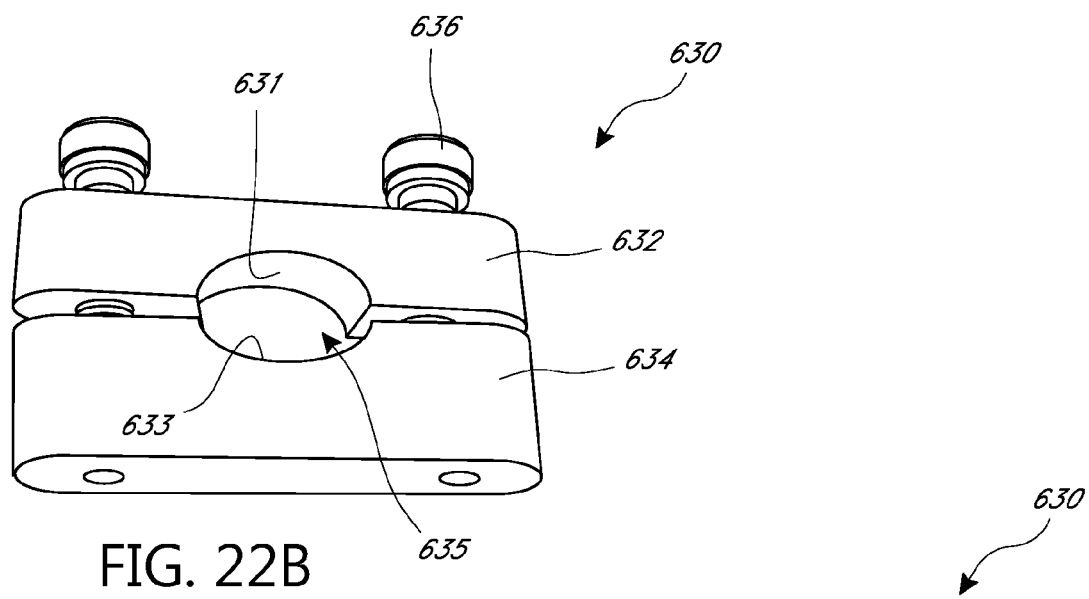
FIG. 22B is a perspective view of the clamp of FIG. 21.
Figure 22C:
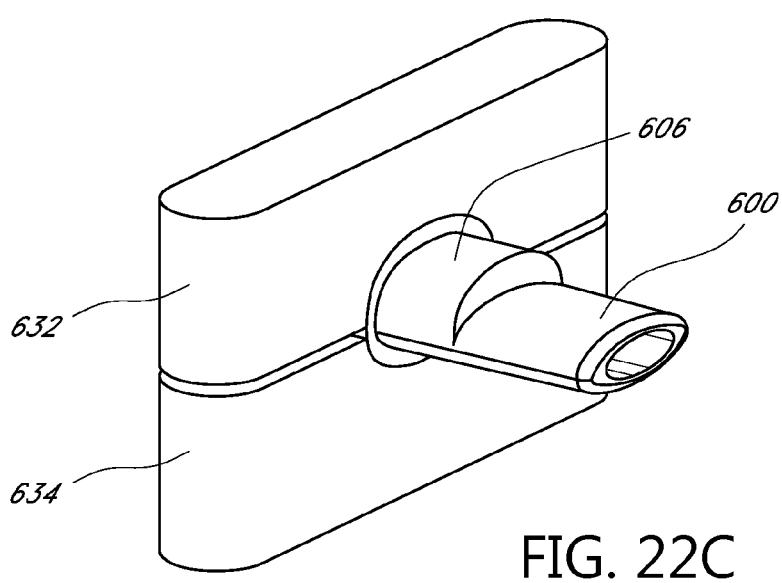
FIG. 22C is a perspective view of the separator tool of FIG. 21 received within the clamp of FIG. 21.

With reference to FIG. 22B, the clamp 630 can have a top portion 632 and a bottom portion 634. The top portion 632 can be secured to the bottom portion 634 by one or more fasteners 636. The top portion 632 can have a recess 631 that longitudinally overlaps with a recess 633 of the bottom portion 634, thereby forming a through hole 635 when the top and bottom portions 632, 634 are secured to one another by the fasteners 634. The through hole 635 can be sized to receive the rear portion 606 of the separator 600. The fasteners 634 can be tightened to clamp the clamp 630 onto the rear portion 606 of the separator 600, as shown in FIG. 22C.

Figure 23A:
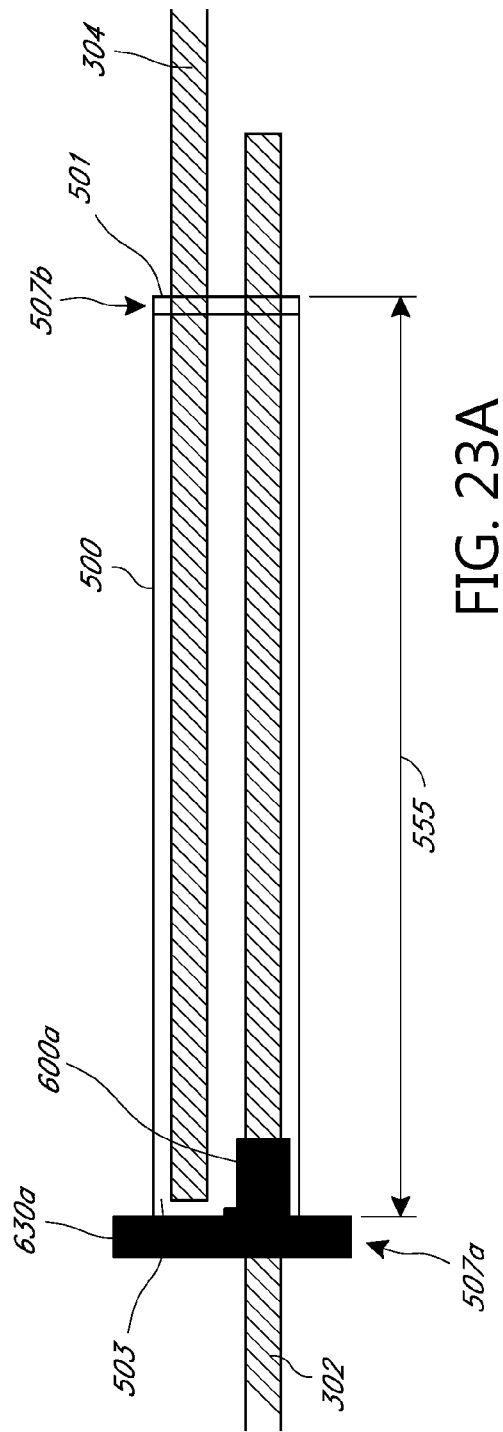
FIG. 23A is a side schematic view of the size adjustment system of FIG. 21 with a separator tool and clamp on one end of the sleeve and the sleeve in an unstretched state.

Referring to FIG. 23A, in some configurations, the sleeve 500 can be an elastic material and can be open at a first end 501 and at a second end 503. The elastic properties of the sleeve 500 can be selected so that extension of the sleeve 500 is self-limiting, with the limitation point of the extension being the maximum extension of the sleeve 500 in the longitudinal direction of the sleeve 500. As mentioned, the headgear 100 can be semi-rigid and may be covered with fabric. The separator 600 is designed to enclose a length of headgear 100 (e.g., a portion of the first or second strap 302, 304) and isolate the length of headgear 100 from the surrounding environment. For example, the separator 600 can enclose a portion of the first strap 302 and isolate the first strap 302 from plastic injected during the molding process.

Figure 23B:
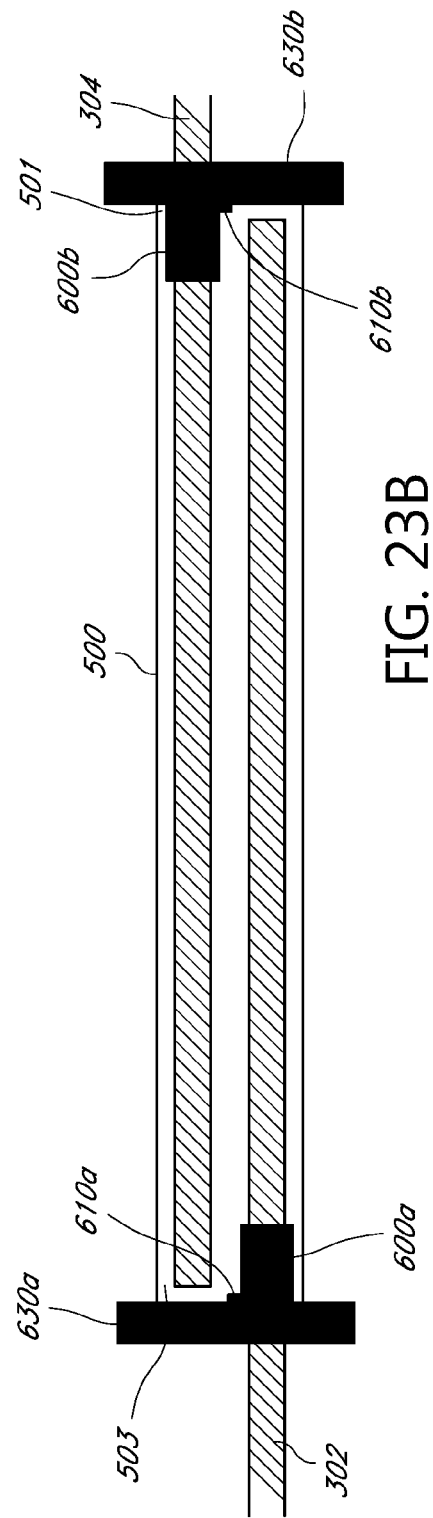
FIG. 23B is a side schematic view of the size adjustment system of FIG. 21 with a separator tool and clamp on each end of the sleeve and the sleeve in a stretched state.

As shown in FIG. 23A, the first strap 302 can be passed through a first separator 600a and advanced through the sleeve 500 from the opening at the second end 503 of the sleeve 500. The first strap 302 can be advanced until it passes out of the opening at the first end 501 of the sleeve 500. The first strap 302 can be advanced to a distance 555 that corresponds with the maximum longitudinal extension of the sleeve 500, as illustrated in FIG. 23A. In some embodiments, the sleeve 500 can include an excess portion 507a,b that extends beyond either end of the distance 555. The second strap 304 can be passed through a second separator 600b and advanced through the sleeve 500 from the opening at the first end 501 until the end of the second strap 304 is level with the abutment 610a of the first separator 600a, as shown in FIG. 23B. The recessed portion of the separator 600 can be configured to correctly position the first and second straps 302, 304 relative to one another for the molding process.

A first clamp 630a can be used to secure the first separator 600a over the first strap 302. In addition to securing the first separator 600a, the first clamp 630a can secure the small excess portion 507a of the sleeve 500 at the second end 503 of the sleeve 500, thereby providing a point of support to the sleeve 500 that can allow the sleeve 500 to be stretched longitudinally when inserted into a mold, as described later.

The sleeve 500 can be extended away from the first clamp 630a to its maximum desired usable length, thereby covering the portion of the first strap 302 that was fed through the first separator 600a. The second separator 600b can be inserted over the end of the second strap 304 that extends outside of the sleeve 500. In some variants, the second separator 600b can be inserted over the opposite end of the second strap 304 before that end of the second strap 304 is inserted into the sleeve 500. The second separator 600b can prevent the second strap 304 from being molded to the first end 501 of the sleeve 500.

With reference to FIG. 23B, the second clamp 630b can secure the second separator 600b over the second strap 304. The second clamp 630b can secure the small excess portion 507b of the sleeve 500 at the first end 501 of the sleeve 500, to provide a point of support of the sleeve 500, thereby allowing the sleeve 500 to be stretched longitudinally when inserted into a mold. In some variants, the first clamp 630a is secured in the mold and held in place by the mold as the sleeve 500 is stretched and secured to the second clamp 630b. The first strap 302 can be positioned with an end thereof level with an abutment 610b.

Figure 24:
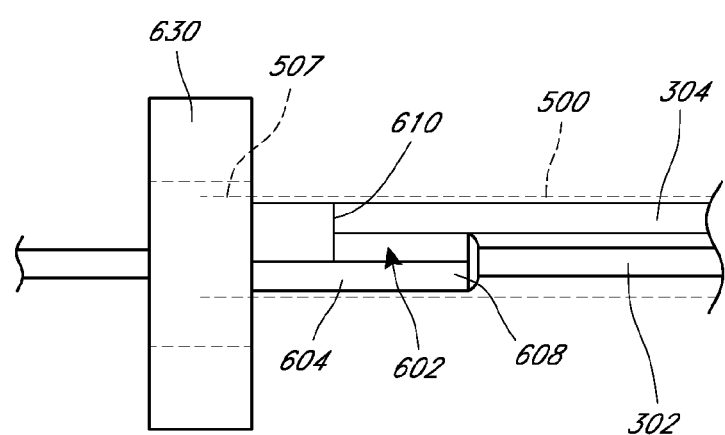
FIG. 24 is a side schematic view of one end of the size adjustment system, separator tool and clamp of FIG. 21.

FIG. 24 is a side view of the separator 600 and the clamp 630 for overmolding the sleeve 500 to the second strap 304 assembled to the first and second straps 302, 304. The sleeve 500 is shown as a dashed line for the sake of clarity. As mentioned above, the top surface 602 of the front portion 608 of the separator 600 is recessed to provide an abutment 610 that helps correctly position the second strap 304 relative to the sleeve 500 for overmolding. The second strap 304 can be positioned for overmolding by advancing the second strap 304 through the sleeve 500 until the end of the second strap 304 contacts the abutment 610. The first strap 302 can similarly be positioned for overmolding by advancing the first strap 302 through the sleeve 500 until the end of the first strap 302 contacts the abutment 610 on the separator 600 at the other end of the sleeve 500.

Figure 25:
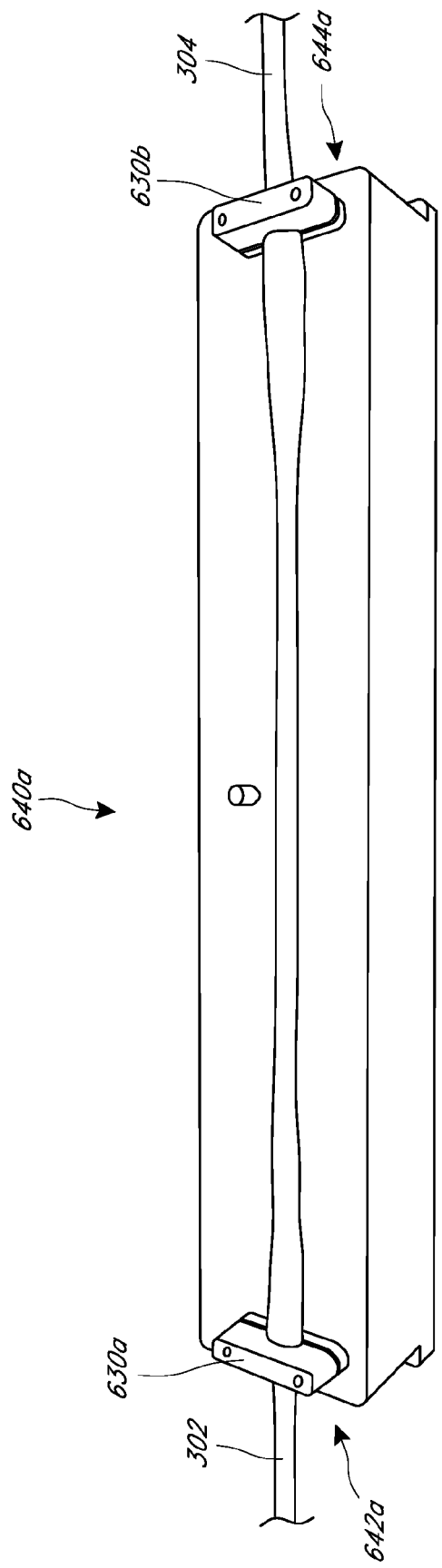
FIG. 25 illustrates the size adjustment system of FIG. 21 positioned within one half of a mold.

Referring to FIG. 25, the sleeve 500 can be overmolded onto the first and second straps 302, 304 of the headgear 100 using a mold tool 640 in the form of an open shut tool that has two halves 640a,b. The first clamp 630a can be inserted into a recess at a first end 642a of a first half 640a of the molding tool 640. The second clamp 630b can be inserted into a recess at a second end 644a of the first half 640a of the molding tool 640. The second half 640b (not shown) of the molding tool 640 can then be placed on top of the first half 640*a* of the molding tool 640, thereby enclosing the sleeve 500 and headgear straps 302, 304 within the molding tool 640.

Figure 26B:
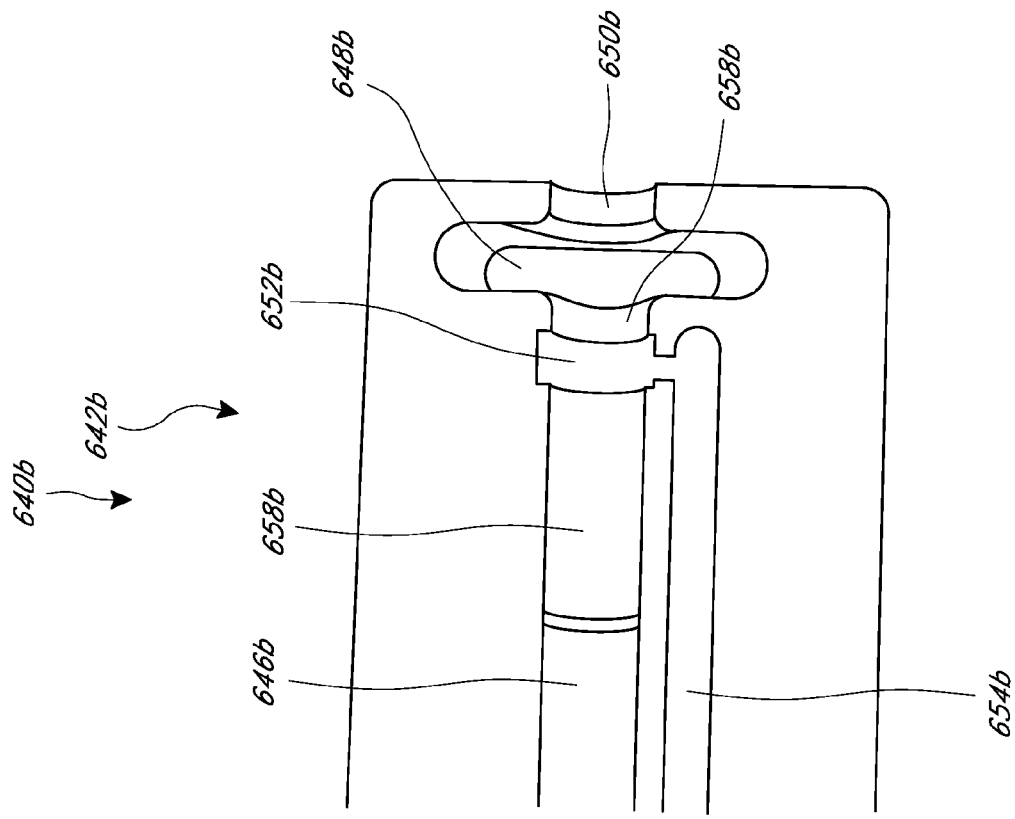
FIG. 26B is a view of one end of the other half of the mold for forming the endcap of the size adjustment system.
Figure 26A:
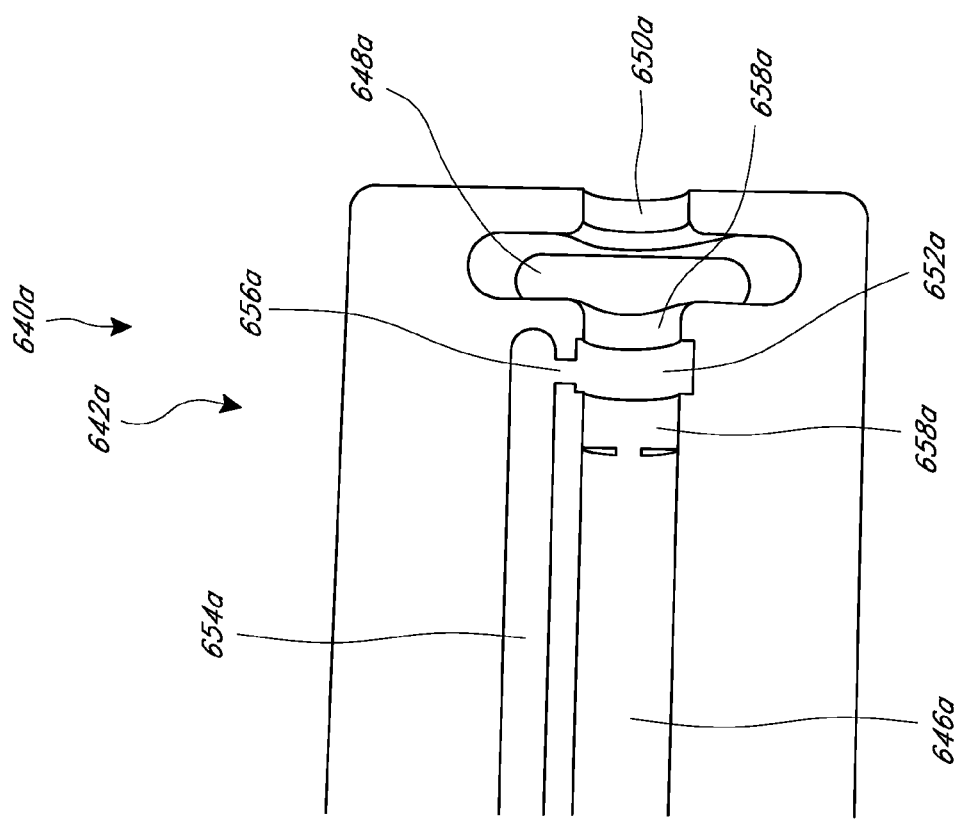
FIG. 26A is a view of one end of one half of a mold for forming an endcap of the size adjustment system.
Figure 27:
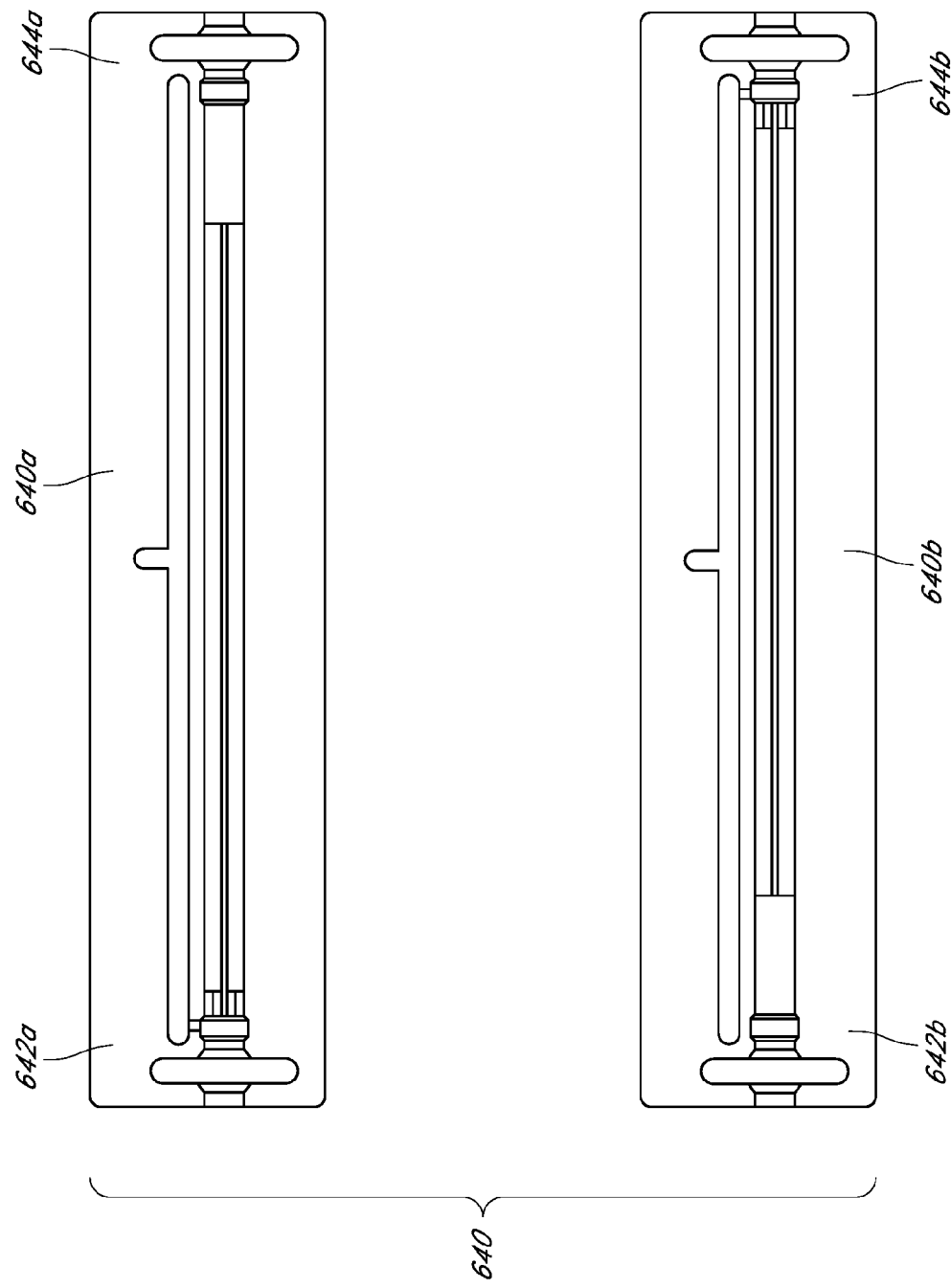
FIG. 27 is a view of mating surfaces of the mold halves for forming the endcaps of the size adjustment system.

FIG. 26A shows an embodiment of the recessed regions of the first end 642*a* of the first half 640*a* of the mold tool 640. The recessed regions can include a strap cavity 646*a* that provides a region within the mold tool 640 for the sleeve 500 and the two lengths of the first and second straps 302, 304 that are circumferentially surrounded by the sleeve 500 to reside during the molding process. The recessed regions can include a clamp cavity 648*a* designed to accommodate the clamp 630. The mold tool 640 can include a headgear exit 650*a* that allows the first or second strap 302, 304 to extend away from the strap cavity 646*a* and exit the mold tool 640. The recessed regions can include a cuff cavity 652*a* that receives a volume of the injected plastic. The recessed regions can include a runner 654*a* that is connected to the cuff cavity 652*a* by a gate 656*a*. The runner 654*a* can provide a channel for high pressure molten plastic to be injected through the gate 656*a* and into the cuff cavity 652*a*, forming the first or second endcap 502, 504 around the exterior of the sleeve 500. The gate 656*a* can be narrow and can create a frangible region that allows the plastic of the runner 654 to be detached from the plastic of the cuff cavity 652 after overmolding is completed. The recessed regions can include shutoffs 658*a* that at least substantially prevent the plastic from spreading out of the cuff cavity 652*a* and down the rest of the strap and at least substantially prevent the plastic from flowing out of the headgear exit 650*a*. In this way, the shutoffs 658*a* can ensure that the sleeve 500 is overmolded only onto the desired region of the strap.

FIG. 26B shows the recessed regions of the first end 642*b* of the second half 640*b* of the mold tool 640. When the mold tool 640 is assembled, the first end 642*b* of the second half 640*b* will overlap the first end 642*a* of the first half 640*a*, as shown in FIG. 26C. Referring to FIG. 26B, the first end 642*b* of the second half 640*b* of the mold tool 640 can include recessed regions that correspond to the recessed regions of the first end 642*a* of the first half 640*a*. The first end 642*b* of the second half 640*b* can have a headgear exit 650*b*, a cuff cavity 652*b*, a runner 654*b*, and shutoffs 658*b*, as described above for the first end 642*a* of the first half 640*a*. The shutoffs 658*b* of the second half 640*b* are dimensioned differently from the shutoffs 658*a* of the first half 640*a* in order to accommodate the different configurations of the separator 600. For example, referring to FIG. 24, the shutoff 658 will have to be longer or shorter depending on whether the recessed portion of the separator 600 is oriented at the top surface or at the bottom surface of the separator 600. The recessed regions can include a strap cavity 646*b*. The recessed regions can include a clamp cavity 648*b*.

As mentioned, the recessed regions are designed such that the molding tool 640 will shut to completely enclose the sleeve 500 and the length of the headgear straps 302, 304 contained within the sleeve 500. When plastic is injected later in the overmolding process, the corresponding protrusions and recesses in the molding tool 640 and the separators 600 cause plastic to be retained in the cuff cavity 652 of the assembled molding tool 640. As can be appreciated from FIG. 27, the two halves of the molding tool 640*a*, 640*b* can be mirror images of one another. In other words, the first end 642*a* of the first half 640*a* can be identical to the second end 644*b* of the second half 640*b*. Likewise, the first end 642*b* of the second half 640*b* can be identical to the second end 644*a* of the first half 640*a*. As discussed above, the separators 600 and the mold tool 640 can have an alternating or opposing design because during molding one end of the mold tool 640 will be molding the sleeve 500 to the upper length of the headgear 100, and the other end will be molding the sleeve 500 to the lower length of the headgear 100.

After the molding process is completed and the separators 600 are removed, the sleeve 500 will be bound to the unprotected regions of the headgear 100 that were within the molding cuff cavities 652. With reference to FIG. 23B, the first end 501 of the sleeve 500 will be molded to the end of the first strap 302, and the second end 503 of the sleeve 500 will be molded to the end of the second strap 304. The first separator 600*a* prevents the sleeve 500 from molding to the first strap 302. This permits the first strap 302 to translate longitudinally through the second endcap 504. The second separator 600*b* prevents the sleeve 500 from molding to the second strap 304. This permits the second strap 304 to translate longitudinally through the first endcap 502.

Figure 28A:
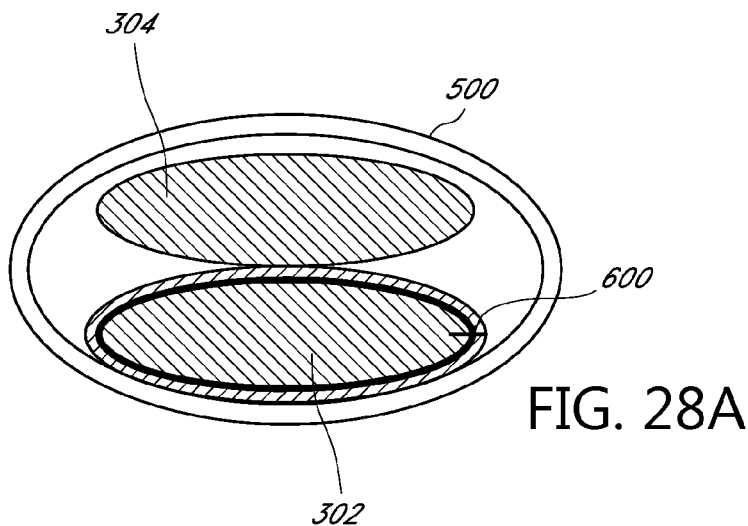
FIG. 28A is a cross-sectional view of an end of the size adjustment system prior to molding of the endcap.
Figure 28B:
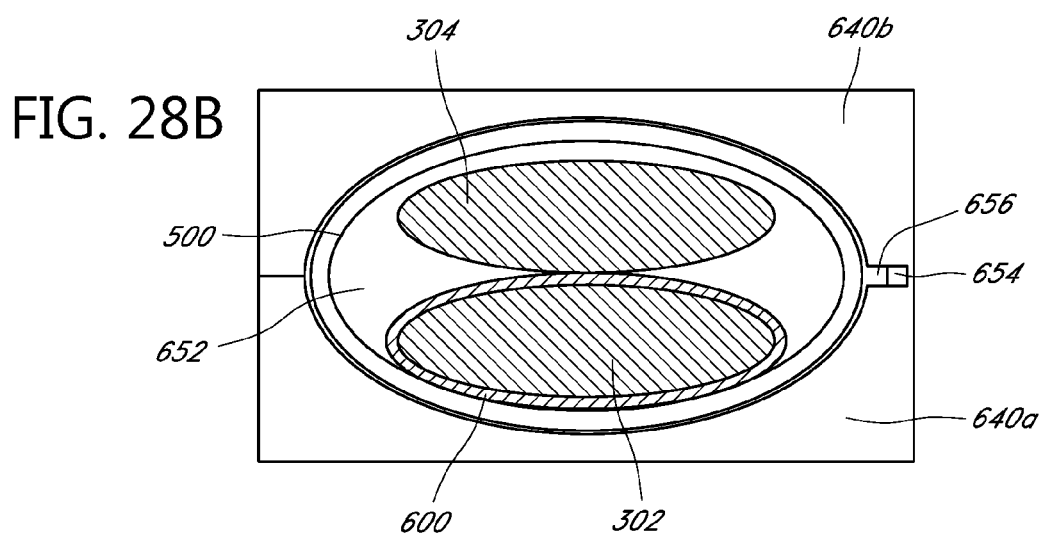
FIG. 28B is a cross-sectional view of the end of the size adjustment system of FIG. 28A within the mold tool.
Figure 28C:
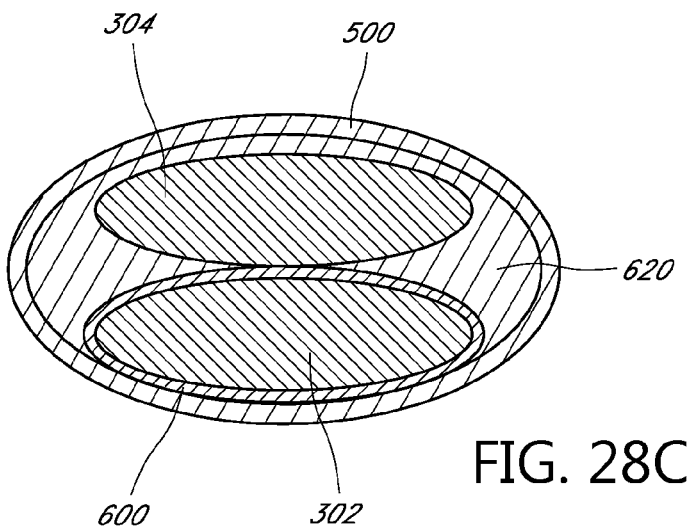
FIG. 28C is a cross-sectional view of the end of the size adjustment system after molding of the endcap.

FIGS. 28A-C show cross-sectional end views of the headgear 100 and molding tool 640 to further illustrate the overmolding process. Referring to FIG. 28A, the sleeve 500 surrounds a first and second strap 302, 304. The first strap 302 is inserted into a separator 600. The second strap 304 is positioned on the recessed portion of the separator 600. FIG. 28B shows the sleeve 500, the straps 302, 304, and the separator 600 in place between the first and second halves 640*a,b* of the molding tool 640. As discussed, the runner 654 and gate 656 provide a channel for plastic to be injected into the cuff cavity 652. FIG. 28C illustrates the sleeve 500, the straps 302, 304, and the separator 600 after the molded plastic 620 has been molded onto the headgear 100. The molded plastic 620 bonds to the sleeve 500 and to the exposed strap (which in the illustrated embodiment is the second strap 304). The molded plastic 620 surrounds the separator 600. The separator 600 can be removed from the molded plastic 620 and from the first strap 302, allowing the first strap 302 free to slide within the hole vacated by the separator 600. The excess portions 507*a,b* (FIG. 24) of the sleeve 500 can be trimmed to give the sleeve 500 a clean, finished look. The result is a complete double ended sliding loop adjustment feature for the semi-rigid headgear 100.

Figure 29:
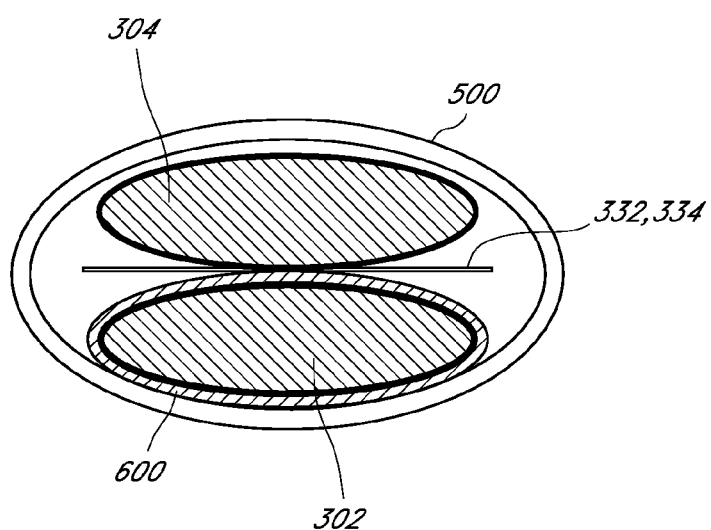
FIG. 29 is a cross-sectional view of an end of a modification of the size adjustment system of FIG. 21 including a tab inserted between first and second straps.

FIG. 29 illustrates a placement of a tab 332, 334 within an overmolded endcap 502, 504. As mentioned with regard to FIG. 19A, the sleeve 500 can include tabs 332, 334 that provide a grip point from pulling the straps 302, 304 over one another. Referring to FIG. 29, the tab 332, 334 can be placed between the straps 302, 304 to reduce the moment the tab 332, 334 imposes on the endcap 502, 504. As illustrated, because the tab 332, 334 is not enclosed by the separator 600, the tab 332, 334 will be molded to the exposed length of the strap 304 and the sleeve 500. Because the tab 332, 334 also extends out from the lateral edge of the headgear strap 304, the tab 332, 334 provides a surface for the user to grab and pull the headgear 100 to tighten the fit. The tab 332, 334 can be designed to include a hook and loop mechanism on the underside to engage the headgear and assist in maintaining a specified strap position, as discussed above with reference to FIG. 20B.

Figure 30:
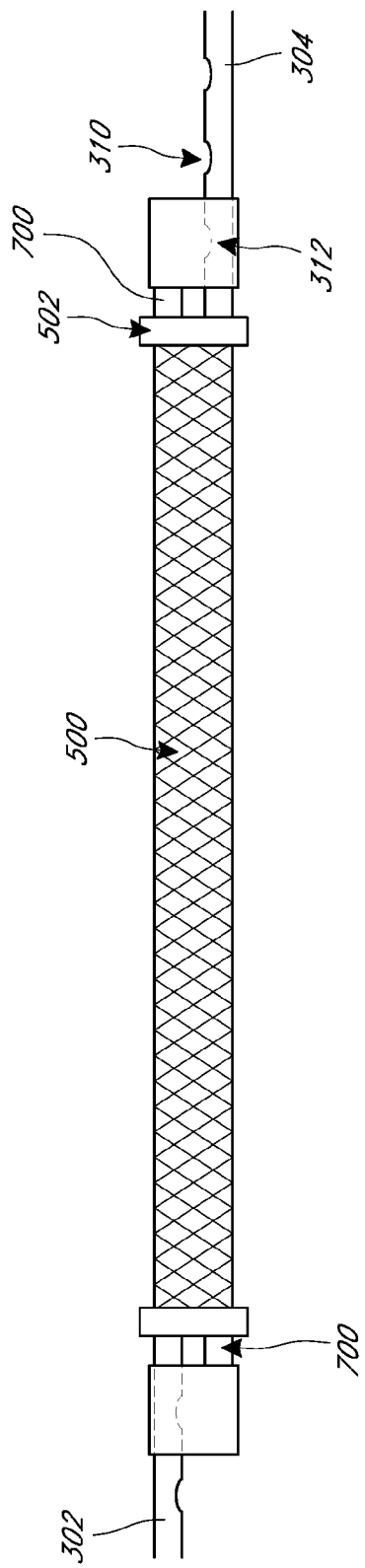
FIG. 30 is illustrates a size adjustment system incorporating an arrangement for providing discrete adjustment positions.

The overmolding process can be used to attach other adjustment features discussed above to the headgear straps 302, 304. For example, FIG. 30 shows the overmolding process can be used to attach the flexible tube adjustment feature discussed in FIGS. 16A-C. The flexible tube 312 can include or be attached to a bridge portion 700 which is molded at the same time as or overmolded onto the endcap 502 as described for the tab 332. Alternatively, the flexible tube 312 can be secured to the endcap 502 other suitable arrangements other than overmolding.

Figure 31:
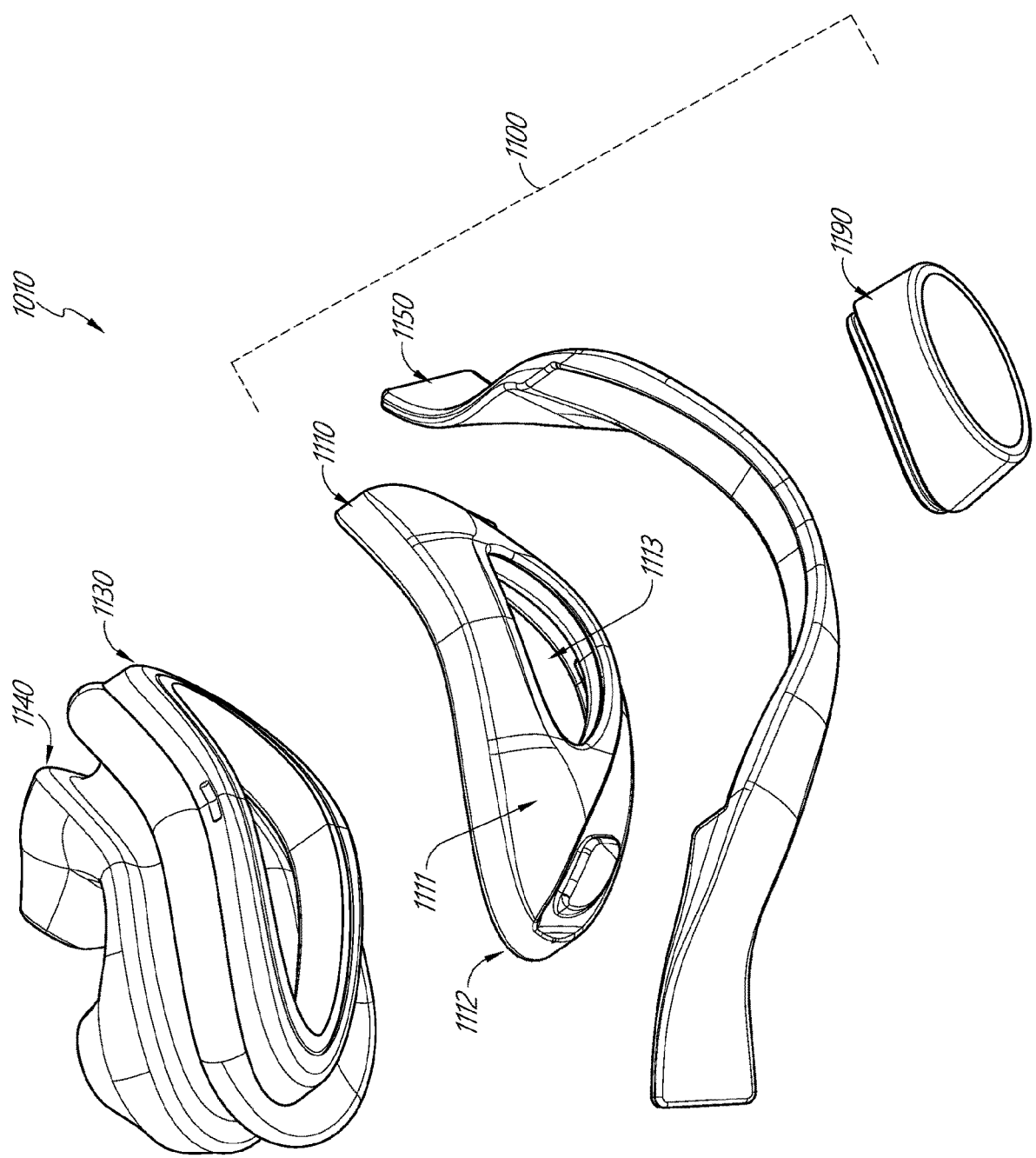
FIG. 31 shows an exploded isometric view of example components of a nasal Obstructive Sleep Apnea (OSA) therapy assembly 1010 in accordance with certain embodiments described herein.

FIG. 31 shows an exploded isometric view of example components of a nasal OSA therapy assembly in accordance with certain embodiments described herein. As shown in FIG. 31, the assembly 1010 can comprise a nasal respiratory interface 1100 including a frame 1110 comprising a front surface 1111, a rear surface 1112, and an aperture 1113 extending from the front surface 1111 to the rear surface 1112. The frame 1110 can have an oval form with a truncated height portion. The frame 1110 (e.g., the rear surface 1112) can be configured to couple to a seal (e.g., via a seal clip 1130) for a nasal pillow 1140. In various embodiments, the frame 1110 can be contoured with the seal. The seal can be removably attached to the frame 1110. The nasal respiratory interface 1100 can also include a yoke 1150. The frame 1110 (e.g., the front surface 1111) can be configured to couple with the yoke 1150. The yoke 1150 can be configured to couple the frame 1110 to a headgear system (not shown). The nasal respiratory interface 1100 can also include a conduit connector (e.g., a gas delivery inlet) 1190 configured to allow gas (e.g., from a gas delivery conduit) through the aperture 1113 of the frame 1110 towards the nasal pillow 1140.

In some embodiments, one or more of the example components of the nasal OSA therapy assembly 1010 can be removably coupled to other components of the assembly 1010. For example, components that may be cleaned and/or replaced often can advantageously be separable from other components that may require a different method of cleaning or that may not require much cleaning and/or replacement. In some embodiments, one or more of the example components of the assembly 1010 can be permanently coupled to other components of the assembly 1010. For example, certain components can be intended for disposable one-time use.

Figure 32B:
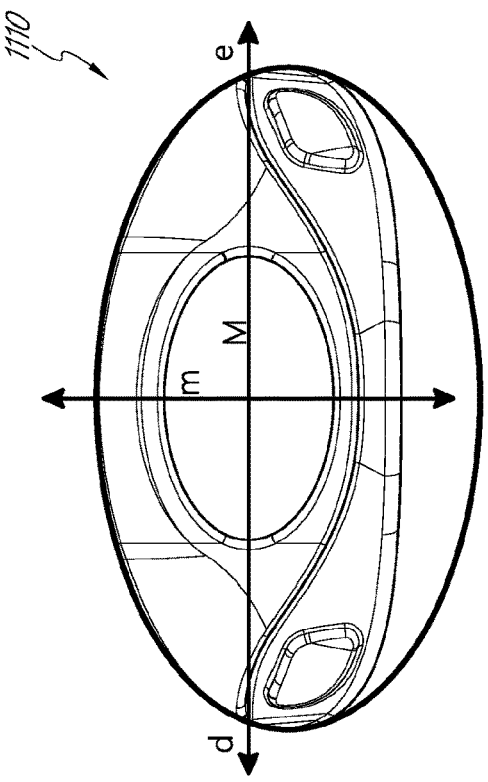
FIGS. 32A, 32B, and 32C show front views of the example frame 1110 of the nasal respiratory interface 1100 shown in FIG. 31.
Figure 32A:
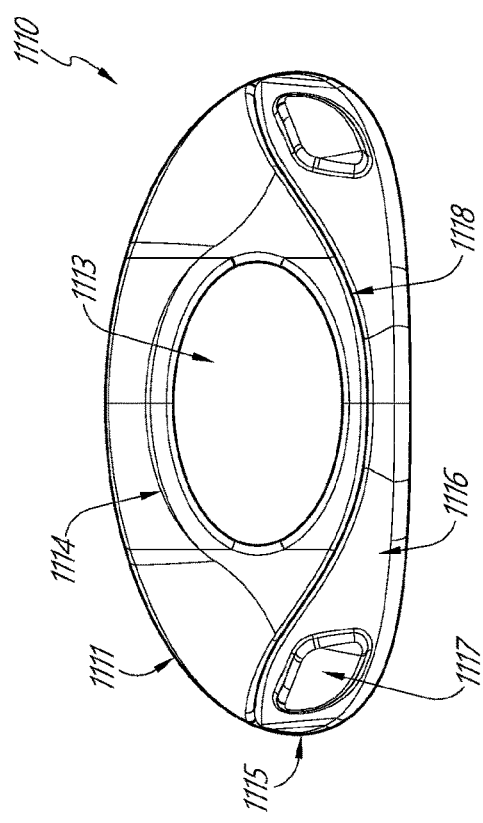
Figure 32C:
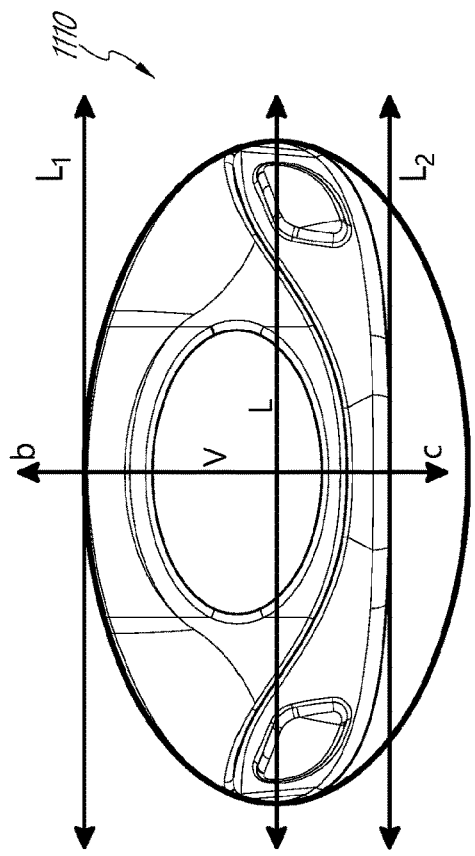

FIGS. 32A-32C show front views of the example frame 1110 of the nasal respiratory interface 1100 shown in FIG. 31. The frame 1110 can be made of a polymeric material. For example, the material can be a relatively hard polymer such as polycarbonate. The frame 1110 can act as a support for the seal. In addition, the frame 1110 can act as a manifold that connects multiple components together. In an alternative form, the frame 1110 can be made of a semi-rigid material such as foam or silicone. In a further alternative form, the frame 1110 can include a rigid skeleton of a metal or rigid plastic with an overmoulded silicone forming a soft envelope or sheath.

In certain embodiments, the frame 1110 can include an aperture 1113 that is centrally located on the frame 1110 along a lateral axis. In various embodiments, the aperture 1113 can comprise an oval shape. For example, as shown in FIG. 32B, the aperture 1113 can have a major axis M and a minor axis m. As described herein, in some embodiments, the shape and size of the aperture can be designed to provide an advantageous compromise for a relatively low profile without a relatively large drop in pressure.

In certain embodiments, the front surface 1111 can be symmetric about the aperture's minor axis m. In various embodiments, the front surface 1111 can be oval in form with a truncated height portion. For example, as shown in FIG. 32C, the front surface 1111 can be defined by a vertical axis V (e.g., a vertical axis substantially bisecting the front surface 1111 and extending through a first end portion b and a second end portion c), a central lateral axis L (e.g., a major lateral axis extending through the longest lateral dimension of the front surface 1111), a lateral axis $L_1$ (e.g., a lateral axis extending through the first end portion b), and a lateral axis L2 (e.g., a lateral axis extending through the second end portion c), where the vertical displacement from L to $L_1$ is greater than the vertical displacement from L to $L_2$. In some embodiments, the vertical displacement from L to $L_2$ can be about ½ to about ⅔ of the vertical displacement from L to $L_1$. Advantageously, certain embodiments of an interface 1100 having a frame 1110 with a truncated height portion can have a lower profile than a frame without a truncated height portion.

As shown in FIGS. 32A-32C, the front surface 1111 can include an upper front surface 1114 and a lower front surface 1115. The frame 1110 can include a recessed region such that the upper front surface 1114 and/or the lower front surface 1115 can include a recessed surface 1116. As described herein, in various embodiments, the recessed surface 1116 of the frame 1110 can mate with a recessed wall of the yoke 1150. In some such embodiments, the front surface 1111 of the frame 1110 can form a substantially flush surface with the front surface of the yoke 1150 when coupled. In FIGS. 32A-32C, the lower front surface 1115 includes the recessed surface 1116. As also shown in FIGS. 32A-32C, a locating projection 1117 can extend from the recessed surface 1116. In various embodiments, as described herein, the locating projection 1117 can couple with a recess of the yoke 1150 in order to couple the frame 1110 to the yoke 1150. As described herein, other types of connection mechanisms are possible.

In certain embodiments, the recessed surface 1116 can be recessed a distance below the maximum height (e.g., elevation) of the upper front surface 1114. The recessed distance is not particularly limited and can be designed according to the intended patient, the intended application, and/or the dimensions of the other components in the assembly 1010. In various advantageous embodiments, the recessed surface 1116 can be recessed from about 0 mm to about 3.5 mm below the maximum height of the upper front surface 1114, or in a range between any of the foregoing values, such as from about 0 mm to about 3 mm (e.g., about 0.5 mm, about 0.75 mm, about 1 mm, about 1.25 mm, about 1.5 mm, about 1.75 mm, or about 2 mm).

In some advantageous embodiments, the recessed surface 1116 can be recessed a maximum distance in a range between any of the foregoing values, such as from about 1 mm to about 3 mm (e.g., about 1.0 mm, about 1.25 mm, about 1.5 mm, about 1.75 mm, about 2.0 mm, about 2.25 mm, about 2.5 mm, about 2.75 mm, or about 3.0 mm). In addition, the elevation of the upper front surface 1114 above the recessed surface 1116 can vary across the area of the recessed surface 1116 to a minimum height in a range between any of the foregoing values, such as from about 0.1 mm to about 0.7 mm (e.g., about 0.1 mm, about 0.2 mm, about 0.3 mm, about 0.4 mm, about 0.5 mm, about 0.6 mm, or about 0.7 mm).

In some advantageous examples, the recessed surface 1116 can be recessed a maximum distance of about 1.36 mm, about 1.37 mm, about 1.38 mm, about 1.39 mm, or about 1.4 mm below the maximum height of the upper front surface 114. In some examples, the elevation of the upper front surface 1114 above the recessed surface 1116 can vary across the area of the recessed surface 1116 to a minimum height of about 0.4 mm, about 0.5 mm, or about 0.6 mm.

Certain embodiments of the frame 1110 can include a recessed surface 1116 extending partially around the aperture 1113. In various embodiments, the recessed surface 1116 can extend adjacent the major axis M of the aperture 1113 at a first end d, under the aperture 1113, and adjacent the major axis M at a second end e. For example, as shown in FIGS. 32A-32C, the origination point of the recessed surface 1116 (or recessed region) is approximately aligned with the major axis M of the aperture 1113 on the left side of the front surface 1111. The recessed surface extends below the aperture 1113, again aligning with the major axis M of the aperture 1113 on the right side of the front surface 1111. In various embodiments, a rounded step 1118 can act as an interface separating the recessed surface 1116 from the upper front surface 1114.

As shown in FIGS. 32A-32C, on each lateral side of the recessed surface 1116 is one or more locating projections 1117. The height of the one or more locating projections 1117 is not particularly limited and can be designed according to the intended patient, the intended application, and/or the dimensions of the other components in the assembly 1010. In some advantageous embodiments, one or more locating projections 1117 can extend a height from about 0.7 mm to about 1.3 mm, or in a range between any of the foregoing values, such as from about 0.85 mm to about 1.25 mm (e.g., about 0.85 mm, about 1.0 mm, about 1.08 mm, about 1.1 mm, about 1.2 mm, or about 1.25 mm). One or more locating projections 1117 can assist in fitting a yoke 1150 to the frame 1110. For example, one or more locating projections 1117 can assist in fitting a yoke 1150 (e.g., having one or more corresponding recesses) to the frame 1110 while maintaining a flush front surface of the frame 1110 and yoke 1150 union. Advantageously, compared to without a flush arrangement, certain embodiments of an interface 1100 having a flush arrangement with the frame 1100 and yoke 1150 can provide a lower profile above the face of the user.

As shown in FIGS. 32A-32C, the frame 1110 can include at least two locating projections 1117. In some embodiments, the presence of at least two locating projections 1117 can help the the yoke 1150 to be fixed in place with the frame 1110 and can reduce (and eliminate in various embodiments) the possibility for rotation (or other form of movement) between the yoke 1150 and the frame 1110 when the interface 1100 is in use.

As shown in FIGS. 32A-32C, the locating projections 1117 can have a trapezoid shape. However, in various embodiments, the shape of the locating projections 1117 may be varied from that shown. For example, the locating projections 1117 can include a circular shape, a cylindrical prism, or a rectangular prism. As described herein, one objective of the locating projections 1117 includes allowing a connection between the frame 1110 and the yoke 1150. In some embodiments including at least two locating projections 1117, one objective of the locating projections 1117 includes securing the orientation of the frame 1110 and yoke 1150 with respect to each other (e.g., to reduce and/or eliminate rotation or other movement). Accordingly, any shape of sufficient size to form a temporary bond between the two parts can be used. For example, the locating projections 1117 can be any shape to match the shape of the corresponding recesses in the yoke 1150. Further, although at least two locating projections 1117 can help reduce rotation (or other forms of movement), in some embodiments, the frame 1110 might include only one locating projection 1117 (e.g., in the center or on one end of the frame 1110).

In some embodiments, one or more locating projections 1117 can be fabricated using the same material as the frame 1110 itself. However, in other embodiments, one or more locating projections 1117 can be fabricated from a different polymer (e.g., a softer polymer) than the frame 1110 which can allow a compression fit to be made between the frame 1110 and the yoke 1150 if desired. For example, the frame 1110 could be made of polycarbonate, while one or more locating projections 1117 can be made of silicone.

Figure 33B:
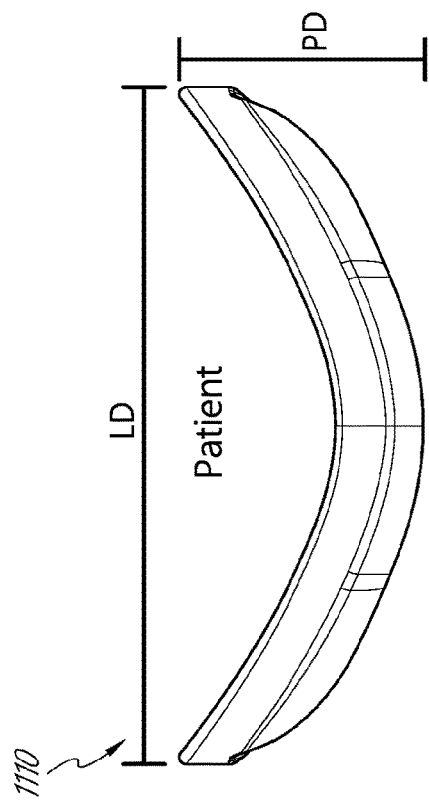
FIGS. 33A-33B show top views of the example frame 1110 of the nasal respiratory interface 1100 shown in FIG. 31.
Figure 33A:
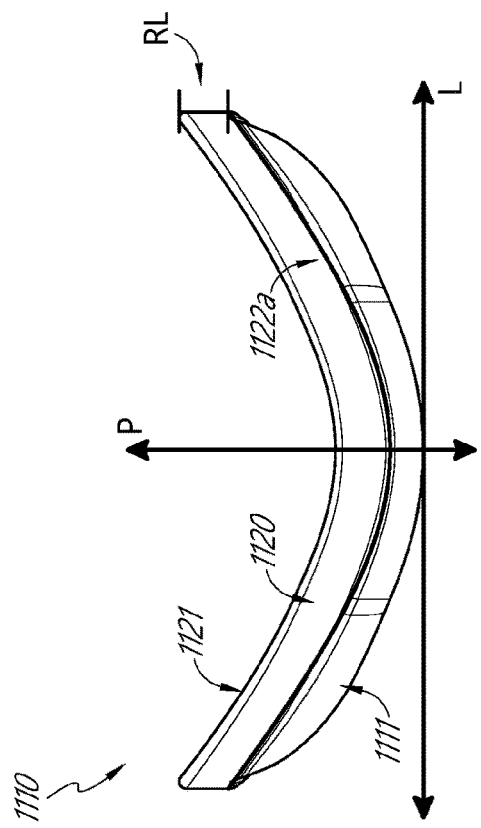

FIGS. 33A-33B show top views of the example frame 1110 of the nasal respiratory interface 1100 shown in FIG. 31. The frame 1110 can include a retaining lip 1121 to couple the frame 1110 to a seal (e.g., via a seal clip 1130 incorporated into the seal as shown in FIG. 31) for a nasal pillow. For example, a retaining lip 1121 can extend around the frame 1110 configured to couple the frame 1110 to a seal clip 1130. As described herein, protrusions can extend from the interior of the retaining lip 1121, which can form a fit with the clip 1130.

As shown in FIGS. 33A-33B, the frame 1110 can include an upper surface 1120. The upper surface 1120 can include the retaining lip 1121 extending a distance RL from the front surface 1111 in the proximal direction that continues around the periphery of the frame 1110. The distance RL is not particularly limited. The distance RL can vary or can be substantially the same extending around the frame 1110. In some advantageous embodiments, the distance RL can include lengths from about 2 mm to about 7 mm, or can be in a range between any of the foregoing values, such as from about 3 mm to about 6 mm (e.g., about 3.5 mm, about 3.6 mm, about 3.7 mm, about 3.8 mm, about 3.9 mm, or about 4.0 mm). In various embodiments, the distance RL can be designed according to the intended patient, the intended application, and/or the dimensions of the other components in the assembly 1010. For example, the distance RL can be modified based on the sealing surface of the seal clip 1130. In certain embodiments where the seal clip 1130 may not leak, a longer retaining lip 1121 may be more ideal.

The periphery of the retaining lip 1121 on the proximal side (e.g., patient side) can be rounded. In some embodiments, a rounded edge 1122a can act as the interface between the front surface 1111 and the retaining lip 1121. In various embodiments, the lateral dimension LD and the proximal dimension PD of the frame 1110 can be defined with respect to the defined lateral axis L and proximal axis P. The lateral dimension LD and the proximal dimension PD are not particularly limited and can be designed according to the intended patient, the intended application, and/or the dimensions of the other components in the assembly 1010. The lateral dimension LD and the proximal dimension PD can change as per size of the interface 1100. In various embodiments, the lateral dimension LD can be longer than the proximal dimension PD such that the seal can be a suitable shape and frame 1110 fits the user's face. In some advantageous examples, the lateral dimension LD of the frame 1110 can be from about 40 mm to about 75 mm, or can be in a range between any of the foregoing values, such as from about 40 mm to about 55 mm (e.g., about 45 mm, about 46 mm, about 47 mm, about 48 mm, about 49 mm, or about 50 mm). In some advantageous examples, the proximal dimension PD of the frame 1110 can be from about 10 mm to about 40 mm (or more), or can be in a range between any of the foregoing values, such as from about 10 mm to about 25 mm (e.g., about 17 mm, about 17.1 mm, about 17.2 mm, about 17.3 mm, about 17.4 mm, or about 17.5 mm). As shown in FIG. 33B, the upper surface 1120 can be symmetric about the proximal axis P, and concave with respect to the patient.

Figure 34B:
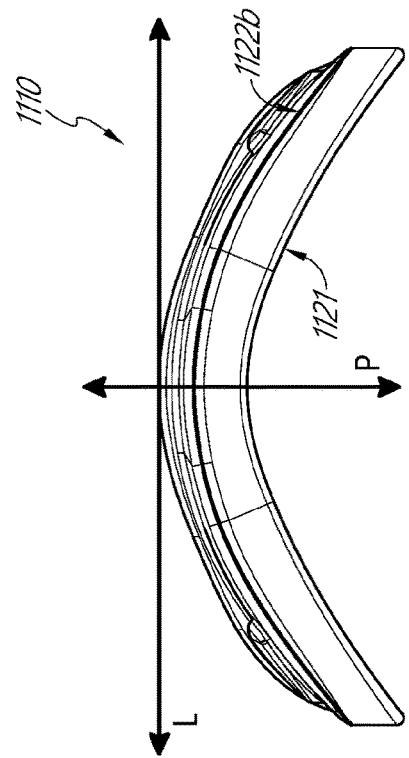
FIGS. 34A-34B show bottom views of the example frame 1110 of the nasal respiratory interface 1100 shown in FIG. 31.
Figure 34A:
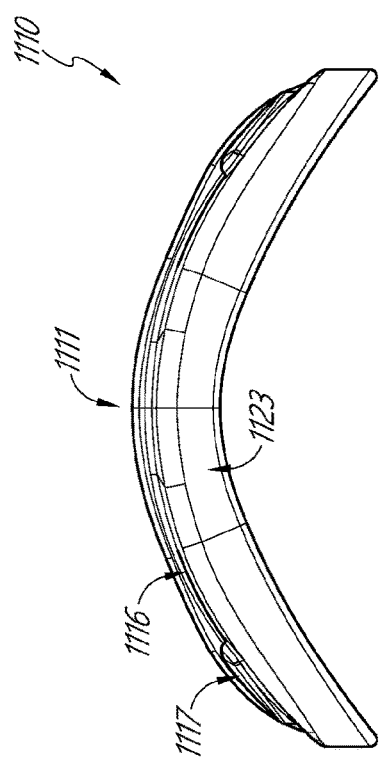

FIGS. 34A-34B show bottom views of the example frame 1110 of the nasal respiratory interface 1100 shown in FIG. 31. The frame 1110 can include a lower surface 1123. Similar to the upper surface 1120, the lower surface 1123 can also include the retaining lip 1121 extending a distance RL from the front surface 1111 in the proximal direction that continues around the periphery of the frame 1110. The distance RL can be similar to those described herein with respect to the retaining lip 1121 shown in FIGS. 33A-33B. In some embodiments, a rounded edge 1122*b* can act as the interface between the front surface 1111 and the retaining lip 1121. In various embodiments, the rounded edge 1122*a* shown in FIGS. 33A-33B and the rounded edge 1122*b* shown in FIGS. 34A-34B are separate from each other. In other embodiments, the rounded edge 1122*a*, 1122*b* can form a continuous edge around the periphery of the frame 1110.

FIGS. 34A-34B also show the recessed surface 1116 and the locating projection 1117 extending from the recessed surface 1116. As described herein, in certain embodiments, the recessed surface 1116 (e.g., via the locating projection 1117) can allow a yoke 1150 to be fitted to the frame 1110 (e.g., within the recessed region) in such a way as to create a substantially flush surface, reducing the overall footprint of the frame 1110.

Figure 35B:
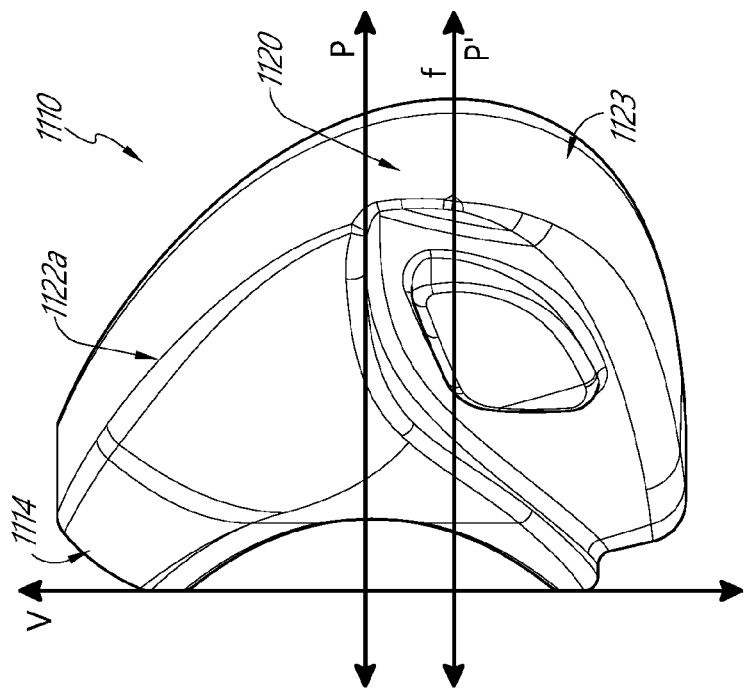
FIGS. 35A-35B show left side views of the example frame 1110 of the nasal respiratory interface 1100 shown in FIG. 31.
Figure 35A:
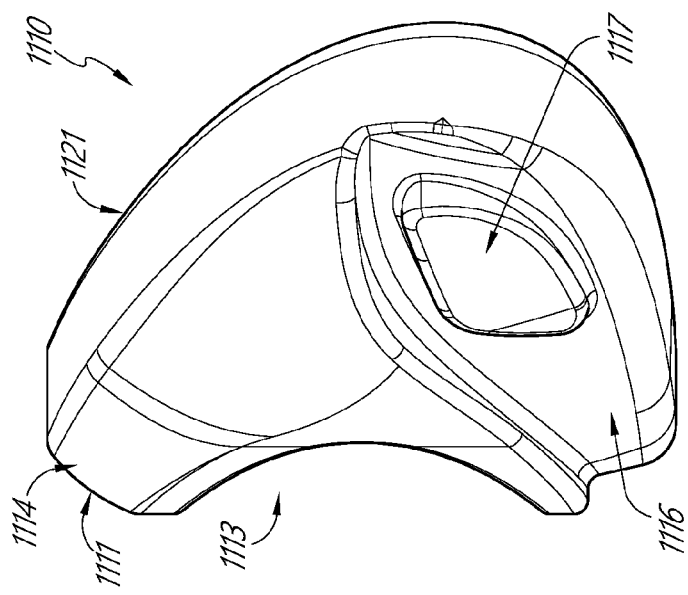

FIGS. 35A-35B show left side views (with respect to the patient) of the example frame 1110 of the nasal respiratory interface 1100 shown in FIG. 31. In the example frame 1110, a first proximal axis P passes centrally through the aperture 1113 of the frame 1110, and a second proximal axis P', vertically displaced from the first proximal axis P indicates the point of separation f between the upper surface 1120 and the lower surface 1123 of the frame 1110. The second proximal axis P' is aligned vertically with the most lateral point f of the frame 1110. The upper front surface 1114 of the frame 1110 is concave in the proximal direction, to the rounded edge 1122*a* that separates the upper front surface 1114 from the upper surface 1120.

FIGS. 36A-36B show rear views of the example frame 1110 of the nasal respiratory interface 1100 shown in FIG. 31. The example frame 1110 includes a rear surface 1112. As shown in FIGS. 36A-36B, the retaining lip 1121 of the frame 1110 can extend around the periphery of the rear surface 1112 of the frame 1110. The thickness t of the retaining lip 1121 is not particularly limited and can be designed according to the intended patient, the intended application, and/or the dimensions of the other components in the assembly 1010. In some advantageous embodiments, the retaining lip 1121 can have a thickness t from about 0.7 mm to about 3.5 mm, or can be in a range between any of the foregoing values, such as from about 0.8 mm to about 3 mm (e.g., about 1.0 mm, about 1.1 mm, about 1.2 mm, about 1.3 mm, about 1.4 mm, 1.5 mm, about 1.6 mm, about 1.7 mm, about 1.8 mm, about 1.9 mm, or about 2.0 mm).

The total vertical dimension VD of the frame 1110 is not particularly limited. In some advantageous embodiments, the total vertical dimension VD of the frame 1110 can be from about 15 mm to about 50 mm, or can be in a range between any of the foregoing values, such as from about 15 mm to about 30 mm (e.g., about 21.8 mm, about 21.9 mm, about 22 mm, about 22.1 mm, about 22.2 mm, about 22.3 mm, about 22.4 mm, or about 22.5 mm). The total vertical dimension VD can be designed according to the intended patient, the intended application, and/or the dimensions of the other components in the assembly 1010. For example, the total vertical dimension VD can be modified based on the seal opening and/or the wall thickness.

In various embodiments, the aperture 1113 has a major dimension MD (e.g., length along its major axis M) and a minor dimension mD (e.g., length along its minor axis). The major dimension MD and/or the minor dimension mD are not particularly limited. In some advantageous examples, the length along its major axis M can be from about 15 mm to about 30 mm, or can be in a range between any of the foregoing values, such as from about 19 mm to about 22 mm (e.g., about 20 mm, about 20.1 mm, about 20.2 mm, about 20.3 mm, about 20.4 mm, about 20.5 mm, about 20.6 mm, about 20.7 mm, about 20.8 mm, about 20.9 mm, or about 21 mm). In some advantageous examples, the length along its minor axis m can be about 10 mm to about 20 mm, or can be in a range between any of the foregoing values, such as from about 11 mm to about 13 mm (e.g., about 11.75 mm, about 12 mm, about 12.25 mm, or about 12.5 mm).

The major dimension MD and/or the minor dimension mD can be designed according to the intended patient, the intended application, and/or the dimensions of the other components in the assembly 1010. Previously, there has not been extensive investigation into the effects on performance of including a range to the major dimension MD and minor dimension mD of the aperture 1113. However, as disclosed herein, the measurements can be advantageously determined in some embodiments by the limits of the gas delivery conduit (e.g., tube), and the pressure drop to be achieved by the conduit. In certain embodiments, the pressure drop can increase with an increasing ratio between the major dimension MD and minor dimension mD. In other words, for various embodiments, as the aperture 1113 becomes more oval in shape, the pressure drop increases. Accordingly, a ratio between the major dimension MD and the minor dimension mD of the aperture from about 1.5 to about 2, or in a range between any of the foregoing values, such as from about 1.5 to about 1.9 (e.g., about 1.6, about 1.7, or about 1.8) can provide an advantageous compromise for a relatively low profile without a relatively large pressure drop.

Figure 38B:
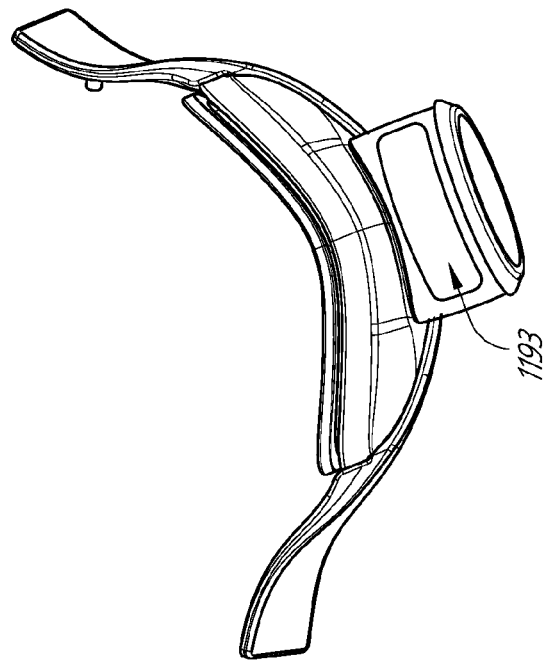
FIGS. 38A-38B show views of an example conduit connector 1190 of the nasal respiratory interface 1100 shown in FIG. 31.
Figure 38A:
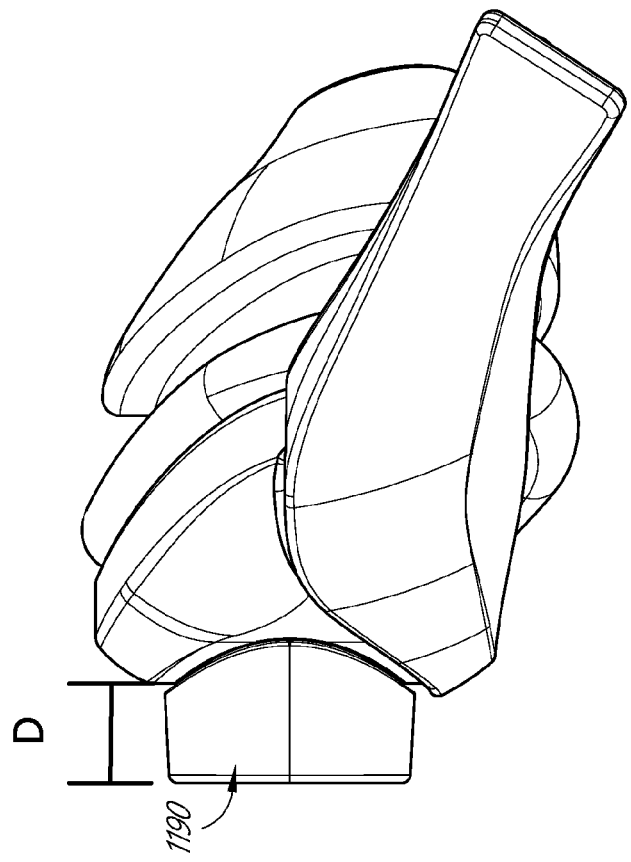
Figure 39:
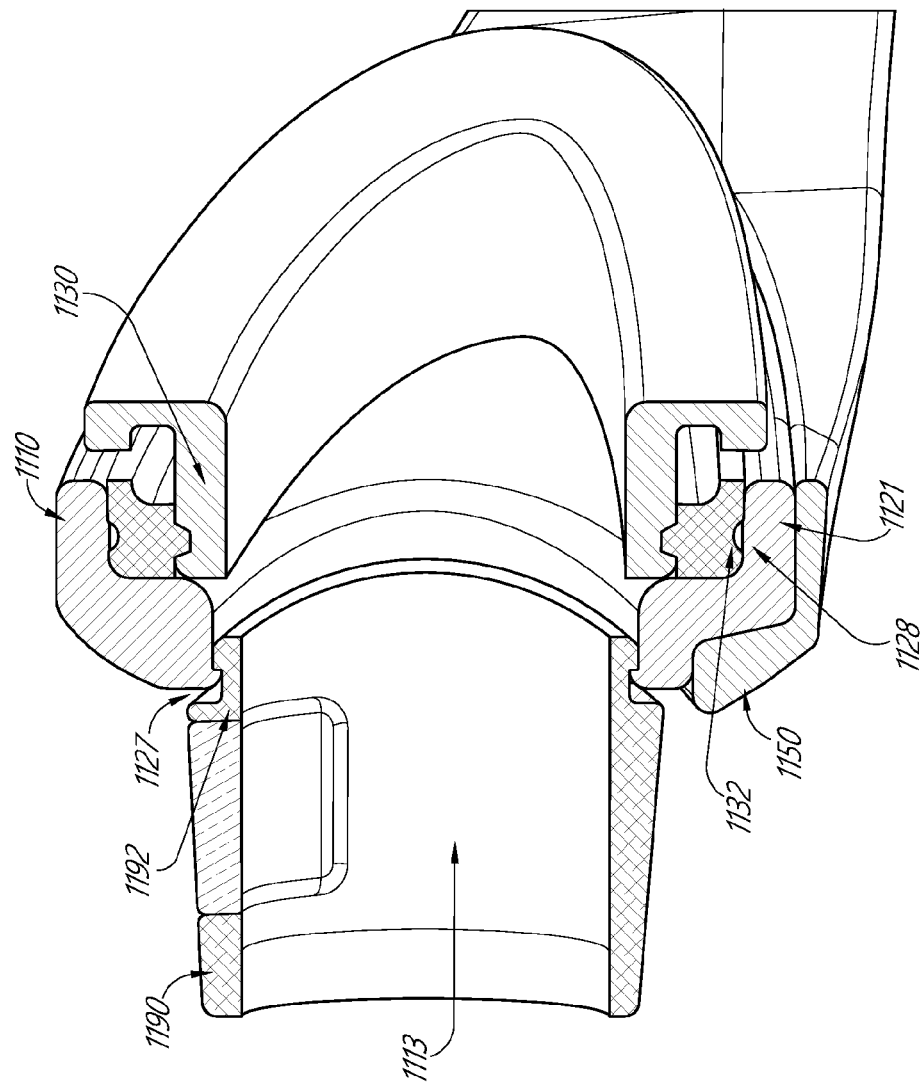
FIG. 39 shows a cross-sectional view of the nasal OSA therapy assembly including the conduit connector 1190, the yoke 1150, the frame 1110, and the seal clip 1130 as seen from the vertical/proximal plane.

FIG. 37 shows a front view of the aperture 1113 of the example frame 1110 of the nasal respiratory interface 1100 shown in FIG. 31. In certain embodiments, a conduit connector 1190 can be configured to allow gas from a gas delivery conduit through the aperture 1113 of the frame 1110 towards the nasal pillow 1140. FIGS. 38A-38B show views of an example conduit connector 1190 of the nasal respiratory interface 1100 shown in FIG. 31. FIG. 39 shows a cross-sectional view of the nasal OSA therapy assembly including the conduit connector 1190, the yoke 1150, the frame 1110, and the seal clip 1130 as seen from the vertical/proximal plane. This view can be useful in showing the interface between the conduit connector 1190 and the frame 1110 (e.g., an example connection mechanism between the conduit connector 1190 and the aperture 1113 of the frame 1110).

As shown in FIGS. 38A-38B, the conduit connector 1190 can extend a distance D in the distal direction from the aperture 1113. The distal distance D is not particularly limited and can be designed according to the intended patient, the intended application, and/or the dimensions of the other components in the assembly 1010. In some advantageous embodiments, the distal distance D can be from about 2 mm to 10 mm, or can be in a range between any of the foregoing values. For example, the distal distance D can be from about 4 mm to about 6 mm (e.g., about 4.9 mm, about 5.0 mm, about 5.1 mm, about 5.2 mm, about 5.3 mm, about 5.4 mm, or about 5.5 mm).

In certain embodiments, the conduit connector 1190 can comprise an oval shape. In some such embodiments, the oval shape can provide an oval shaped gas flow path to the aperture 1113 of the frame 1110, which can also comprise an oval shape. In other words, an oval shaped conduit connector 1190 can communicate with an oval shaped aperture 1113 of the frame 1110 such that the interface can have a reduced height dimension.

For example, an oval shape can allow a reduction in the overall height of the aperture 1113 of the frame 1110 and of the conduit connector 1190 while maintaining the same surface area as a corresponding circle. Accordingly for various embodiments, an oval shape can allow a reduction in the profile of the frame 1110 without compromising the volumetric flow of gas that may be passed through the aperture 1113.

An example connection mechanism to secure the conduit connector 1190 to the frame 1110 can utilize protrusions and corresponding recesses. As shown in FIG. 39, the conduit connector (e.g., an oval shaped gas delivery inlet) 1190 can be connected to the aperture 1113 of the frame 1110 through the use of exterior protrusions 1127. For example, the conduit connector 1190 can connect to the aperture 1113 of the frame 1110 utilizing protrusions 1127 built into the aperture 1113 and corresponding recesses 1192 designed into the conduit connector 1190. A recess 1192 can be present on the upper and lower sections of the conduit connector 1190, and protrusions 1127 can be present on the upper and lower sections of the aperture 1113 of the frame 1110. In various embodiments, these shapes can allow a fit, e.g., an interference or friction fit, to be made when the conduit connector 1190 is pressed into the aperture 1113 of the frame 1110. In other examples, the protrusions can be incorporated into the conduit connector 1190 and the recesses into the aperture 1113. The connection mechanism is not particularly limited. The connection mechanism can be any known in the art or yet to be developed. For example, the connection mechanism can include a compressible snap-fit or a twist lock. In addition, in some embodiments, the conduit connector 1190 may be coupled directly with the seal clip 1130 instead of being coupled to the frame 1110.

In some embodiments, the conduit connector 1190 can incorporate bias holes and/or a diffusor (e.g., a diffusor mat) 1193 into a bias flow system. Bias holes can be calibrated to maintain a desired air pressure, and a diffuser can help reduce noise of the flow exiting the bias holes. The diffusor can act to dissipate the energy of the flow out of the gases. As shown in FIG. 38B, an overmoulded diffusor mat 1193 can be incorporated into the system. In the shown example, the diffusor mat 1193 can be rectangular in nature, contoured with the curvature of the conduit connector 1190. In other variations, the diffusor 1193 can be oval shaped or there may be more than one diffusor 1193 spaced around the conduit connector 1190. In some embodiments, the conduit connector 1190 can be designed to be permanently connected to a gas delivery conduit on the distal end to facilitate the transfer of gas to the patient. In some such embodiments, the conduit connector 1190 can be moulded to the gas delivery conduit forming a continuous piece.

The view in FIG. 39 can also be useful in showing an example connection mechanism between the frame 1110 and the seal clip 1130. The example connection mechanism also utilizes protrusions and corresponding recesses to secure the frame 1110 to the nasal pillow seal. Similar to the example connection mechanism between the conduit connector 1190 and the aperture 1113 of the frame 1110, the interior side of the retaining lip 1121 of the frame 1110 can include protrusions 1128 at the upper and lower sections, with corresponding recesses 1132 at the upper and lower sections of the seal clip 1130. In various embodiments, this can allow the frame 1110 to be pressed into place over the seal clip 1130 with the configuration retained. In other examples, the protrusions can be incorporated into the seal clip 1130 and the recesses into the retaining lip 1121. The connection mechanism is not particularly limited. The connection mechanism can be any known in the art or yet to be developed. For example, the connection mechanism can include a compressible snap-fit or a twist lock.

Figure 40A:
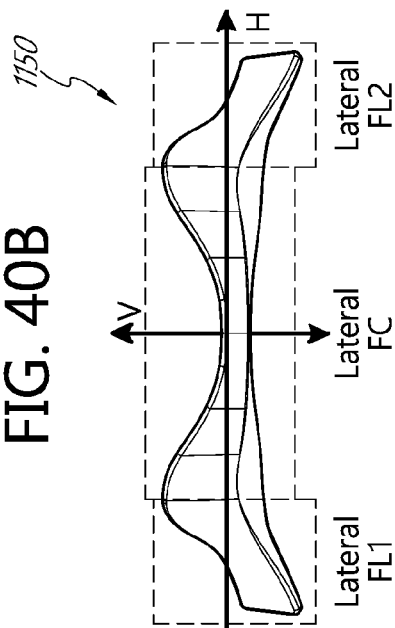
FIGS. 40A, 40B, and 40C show front views of an example yoke 1150 of the nasal respiratory interface 1100 shown in FIG. 31.
Figure 40B:
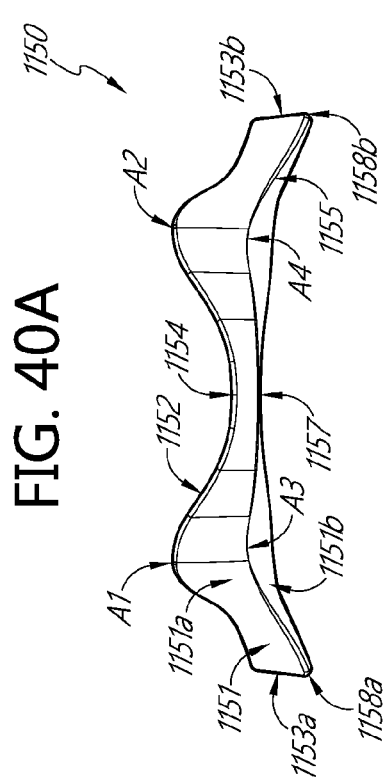
Figure 40C:
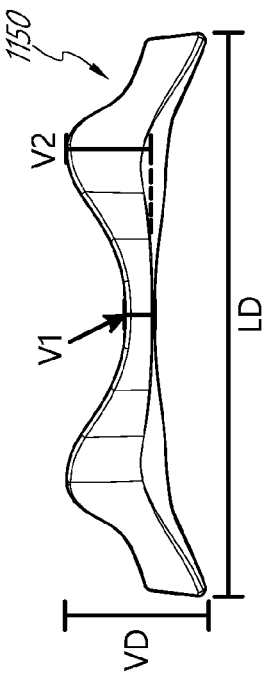

FIGS. 40A-40C show front views of an example yoke 1150 of the nasal respiratory interface 1100 shown in FIG. 31. In certain embodiments, the yoke 1150 can provide a compact, lightweight and unobtrusive connection between the frame 1110 and headgear. In some embodiments, the yoke 1150 can be configured to couple with a head strap to form a closed (e.g., uninterrupted) loop and/or to allow adjustability of the head strap. For example, the length of the head strap can be adjustable to permit adjustment to a patient's head size. A closed loop can allow the headgear to be separated from the interface 1100 without the need to change the tightness settings of the head strap. This can be advantageous in certain embodiments because the user would not need to readjust the strap and/or refit the strap with the desired tightness.

In various embodiments, the yoke 1150 and the headgear can be separated from the air path components' flow path (e.g., separate from the aperture 1113 of the frame 1110 and the conduit connector 1190), which can allow adjustability of the headgear without breaking the seal. In addition, in certain embodiments, as the yoke 1150 is not in the air path, it can be cleaned separately and/or in a different way from the other components. The yoke 1150 of certain embodiments can also provide support to the seal and help maintain the frame 1110 in position. For example, the yoke 1150 can help prevent the frame 1110 from pulling off the seal due to a pulling force from a gas delivery conduit, especially while the patient may be lying down. In various embodiments, the yoke 1150 can be made with the same material as the frame 1110. In other embodiments, the yoke 1150 can be made with a different material as the frame 1110.

As shown in FIGS. 40A-40C, the yoke 1150 can be symmetrical about a vertical axis V, and can include a front surface 1151 (or front wall) that includes a central portion FC and two portions FL1, FL2 laterally displaced from the central portion FC. The yoke 1150 can be asymmetrical relative to a horizontal axis H. The front surface 1151 of the yoke 1150 can include a front upper surface 1151a and a front lower surface 1151b. In various embodiments, the central portion FC can span from one laterally displaced apex A1 of the upper edge 1152 of the front upper surface 1151a to another laterally displaced apex A2 of the upper edge 1152 of the front upper surface 1151a. The lateral portions FL1, FL2 can span from the lateral edge 1153a, 1153b of the yoke 1150 to the corresponding apex A1, A2 of the upper edge 1152 of the front upper surface 1151a. The upper edge 1152 of the central portion FC can include a smooth gradient curve from one apex A1, A2 to the other, which includes a lower point 1154. The upper edge 1152 of the lateral portions FL1, FL2 can include a curve from the apex A1, A2 of the upper edge 1152 of the front upper surface 1151a to the lateral edge 1153a, 1153b of the yoke 1150.

In certain embodiments, the lower edge 1155 of the front upper surface 1151a can be adjacent to the front lower surface 1151b. The lower edge 1155 of the front upper surface 1151a can span from one central low point 1157 to a laterally displaced apex A3, A4. From this apex A3, A4, the lower edge 1155 of the front upper surface 1151a can span to a low point 1158a, 1158b on each lateral edge 1153a, 1153b. The lower edge 1155 of the front upper surface 1151a can include a smooth gradient curve from the central low point 1157 to the laterally displaced low points 1158a, 1158b. In various embodiments, the lateral edges 1153a, 1153b of the front upper surface 1151a can be angled with respect to the vertical axis V.

The dimensions of the yoke 1150 are not particularly limited and can be designed according to the intended patient, the intended application, and/or the dimensions of the other components in the assembly 1010. In various advantageous embodiments, the lateral dimension LD of the yoke 1150 can be about 40 mm to about 75 mm, or can be in a range between any of the foregoing values, such as 45 mm to about 50 mm (e.g., about 45 mm, 46 mm, 47 mm, about 48 mm, 49 mm, or about 50 mm). The vertical dimension VD of the yoke 1150 can be about 15 mm to about 25 mm, or can be in a range between any of the foregoing values, such as 19.5 mm±1 mm (e.g., about 18.5 mm, about 19 mm, about 19.5 mm, about 20 mm, or about 20.5 mm). In some advantageous embodiments, the vertical distance V1 from the upper edge 1152 of the front surface 1151 to the central low point 1157 can be about 3 mm to about 4.5 mm, or can be in a range between any of the foregoing values, such as 3.76 mm±0.26 mm (e.g., about 3.5 mm, about 3.6 mm, about 3.7 mm, about 3.8 mm, or about 4 mm). In some advantageous embodiments, the vertical distance V2 from the apex A1, A2 of the upper edge 1152 of the front surface 1151 to the to the central low point 1157 can be about 7 mm to about 16 mm, or can be in a range between any of the foregoing values, such as 12 mm±2 mm (e.g., about 10 mm, about 11 mm, about 12 mm, about 13 mm, or about 14 mm).

Figure 41:
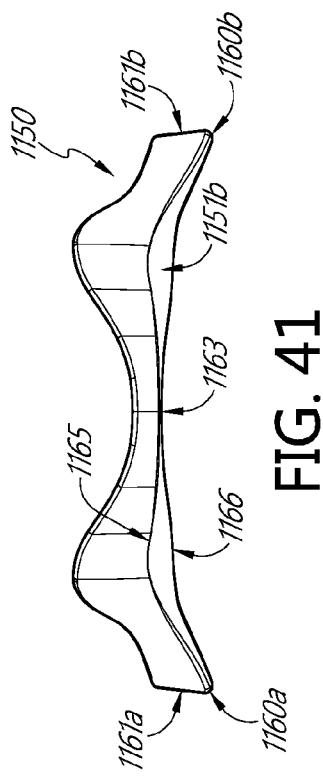
FIG. 41 shows a front view of the example yoke 1150 showing example features.

FIG. 41 shows a front view of the example yoke 1150 showing example features of the front lower surface 1151b. In certain embodiments, the front lower surface 1151b can span from two lower localities 1160a, 1160b, each at a lateral edge 1161a, 1161b of the yoke 1150, to a centrally located apex 1163. In various embodiments, the upper edge 1165 of the front lower surface 1151b can follow the contour of the lower edge 1155 of the front upper surface 1151a of the yoke 1150. In some examples, there can be a rounded interface separating the two 1155, 1165. The front profile of the lower edge 1166 of the lower surface 115b of the yoke 1150 can be mapped by a smooth gradient curve from each of the lateral low points 1160a, 1160b to the central apex 1163.

Figure 43B:
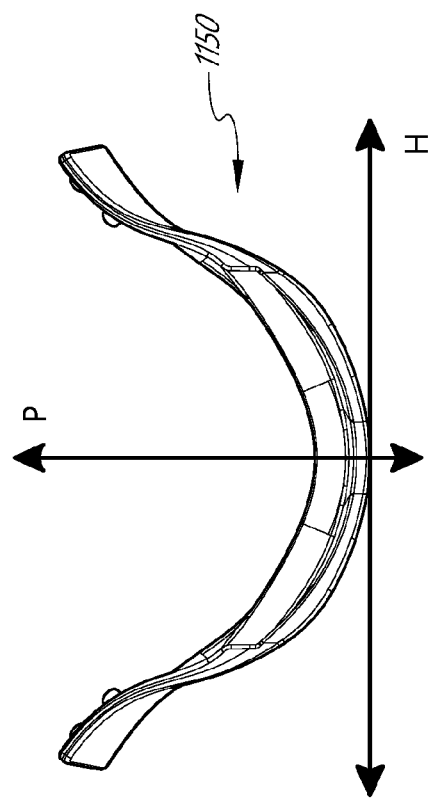
FIGS. 43A-43B show top views of the example yoke 1150 showing curvature.
Figure 43A:
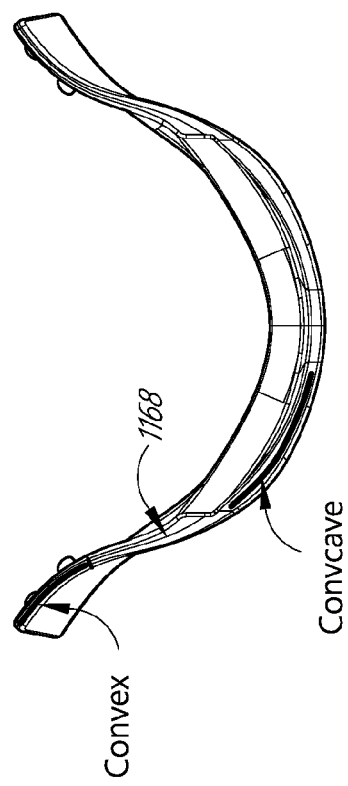

FIGS. 42A-42C show top views of the example yoke 1150 showing example features. FIGS. 43A-43B show top views of the example yoke 1150 showing curvature. As shown, the top profile of the yoke 1150 can include the front surface 1151, a forward wall 1170, a top surface (e.g., a top lateral surface) 1171, and a shelf 1172.

In some advantageous embodiments, the proximal distance PD of the yoke 1150 can be about 35 mm to about 45 mm, or can be in a range between any of the foregoing values, such as 39 mm±1 mm (e.g., about 38 mm, about 38.5 mm, about 39 mm, about 39.5 mm, or about 40 mm). In some advantageous embodiments, the distance FT from the forward wall 1170 to the top surface 1171 can be about 1 mm to about 3 mm, or can be in a range between any of the foregoing values, such as 2 mm±0.5 mm (e.g., about 1.5 mm, about 1.75 mm, about 2 mm, about 2.25 mm, or about 2.5 mm). In some advantageous embodiments, the distance FS from the forward wall 1170 to the end of the shelf 1172 can be about 2.5 mm to about 6 mm, or can be in a range between any of the foregoing values, such as 4.3 mm±1 mm (e.g., about 3.3 mm, about 4 mm, about 4.3 mm, about 5 mm, or about 5.3 mm). Other values for the proximal distance PD, the distance FT from the forward wall 1170 to the top surface 1171, and/or the distance FS from the forward wall 1170 to the end of the shelf 1172 are possible. These values can be designed according to the intended patient, the intended application, and/or the dimensions of the other components in the assembly 1010.

As the front surface 1151 extends laterally from the proximal axis P, the front surface 1151 can curve so that it is concave in the proximal direction (e.g., with respect to the patient) in some embodiments. As shown in FIGS. 43A-43B, at an inflection region 1168 laterally displaced from the proximal axis P, the curve can transition from a concave shape to a convex shape relative to the proximal direction (e.g., relative to the patient) in some embodiments. In some embodiments, this curvature can allow the yoke 1150 to rest on, or circumvent the cheeks of the patient. As show in FIGS. 42B and 43B, the yoke 1150 can curve away from a horizontal axis H.

The top surface 1171 of the lateral portions FL1, FL2 of the yoke 1150 can be longer in length than the corresponding bottom surface (e.g., bottom lateral surface) 1174 of the lateral portions FL1, FL2. The increased length of the top surface 1171 relative to the bottom surface 1174 can result in an effective rotation of the lateral portions FL1, FL2 of the yoke 1150 along their length, exposing a portion of the front surface 1151 to a top view. Another way of expressing this is that the lateral portions FL1, FL2 of the yoke 1150 can twist along their length in some embodiments. In some such embodiments, the lateral edges 1153a, 1153b of the yoke 1150 can be substantially seamlessly connected to headgear, e.g., to help prevent a head strap from twisting such that it can be positioned flush with the patient's head.

Figure 44B:
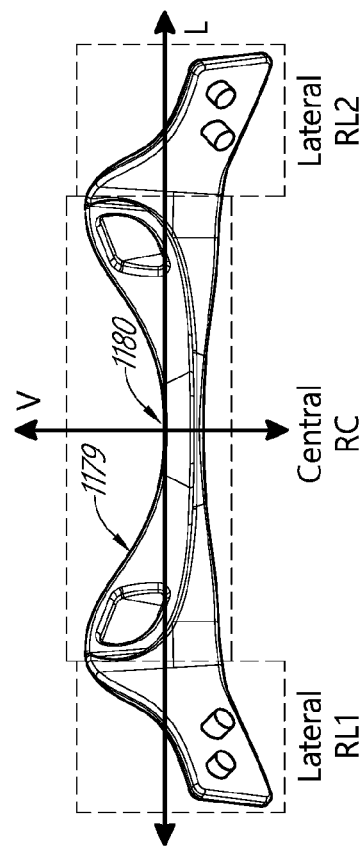
FIGS. 44A-44B show rear views of the example yoke 1150 showing example features.
Figure 44A:
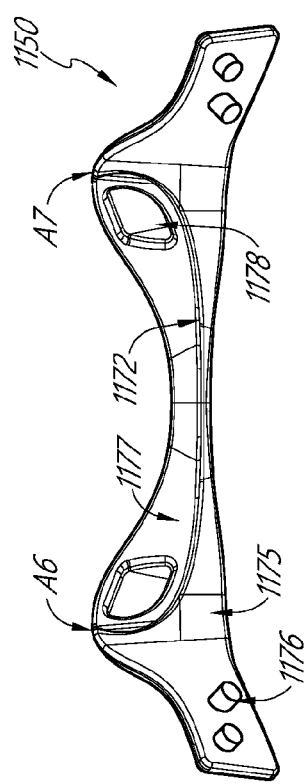

In various embodiments, the shelf 1172 can assist the yoke 1150 in supporting the frame 1110 and can be created as a result of a recess in the rear wall, as described herein with respect to FIGS. 44A-44B. FIGS. 44A-44B show rear views of the example yoke 1150 showing example features. The rear profile of the yoke 1150 includes a rear wall 1175 (e.g., a rear surface) with a number of projections or protrusions 1176, a recessed wall 1177, and a recessed locator 1178, and a shelf 1172. The rear profile of the yoke 1150 can also include the central portion RC and two lateral portions RL1, RL2. The central portion RC can span from one laterally displaced apex A6 of the upper edge 1179 of the rear wall 1175 to another laterally displaced apex A7 of the upper edge 1179 of the rear wall 1175. The upper edge 1179 of the central portion RC can include a smooth gradient curve from one apex A6, A7 to the other, which can include a lower point 1180.

In various embodiments, the central portion RC can include a region that is recessed from the rear wall 1175, forming a recessed wall 1177. A shelf 1172 can separate the rear wall 1175 and the recessed wall 1177. The shelf 1172 can span from a point near one of the apexes A6 of the upper edge 1179 of the rear wall 1175 to a point near the other apex A7 of the upper edge 1179 of the rear wall 1175. In this example embodiment, the recessed wall 1177 of the yoke 1150 can be configured to mate with the recessed surface 1116 of the frame 1110. The frame 1110 can sit on the shelf 1172 of the yoke 1150 such that the shelf 1172 can help support the frame 1110.

In addition, the recessed wall 1177 can include at least one recessed locator 1178 to couple with the locating projection 1117 of the frame 1110. In the example embodiment, the recessed wall 1177 includes two laterally displaced recessed locators 1178. These locators 1178 can be designed to fit with corresponding locating projections 1117 on the frame 1110 in order to enable a connection to be made between the frame 1110 and the yoke 1150. This, in certain such embodiments, can help prevent rotation between the two components.

Similar to the front surface 1151 as described herein, both the rear wall 1175 and recessed wall 1177 in some embodiments can curve so that they are concave in the proximal direction as they extend in the lateral direction. At an inflection region laterally displaced from the vertical axis V, the curve can transition from a concave shape to a convex shape relative to the proximal direction.

Figure 45B:
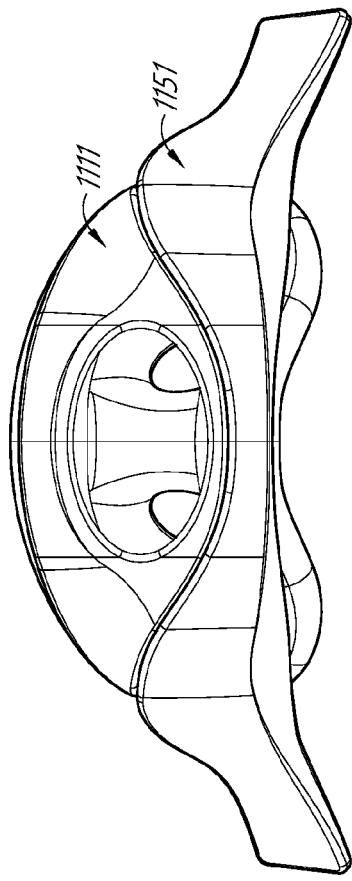
FIG. 45B shows a front view of the example yoke 1150 coupled to the example frame 1110.
Figure 45A:
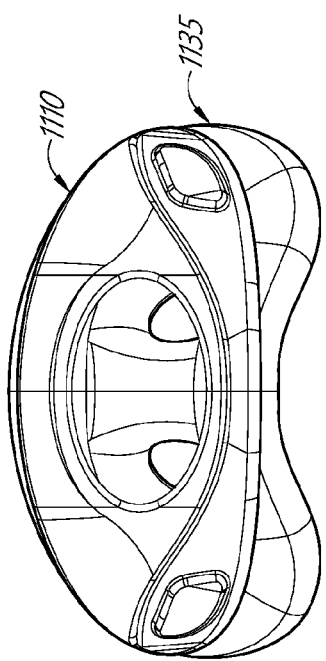
FIG. 45A shows a front view of the example frame 1110 coupled to a nasal seal in accordance with certain embodiments described herein
Figure 45C:
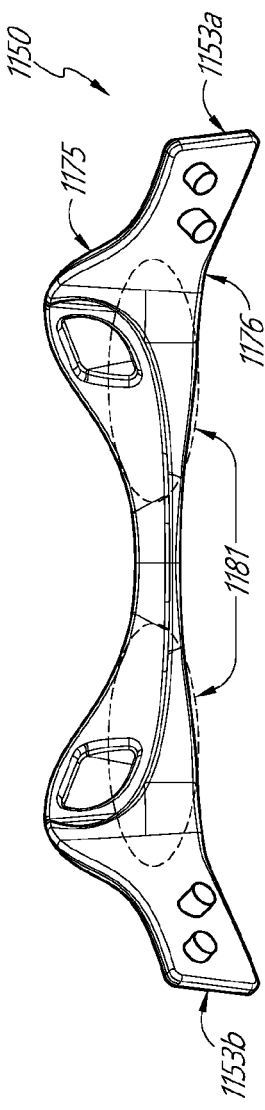
FIG. 45C shows a rear view of the example yoke 1150 of the nasal respiratory interface 1100 shown in FIG. 31.

FIG. 45A shows a front view of the example frame 1110 coupled to a nasal seal 1135 in accordance with certain embodiments described herein. FIG. 45B shows a front view of the example yoke 1150 coupled to the example frame 1110. FIG. 45C shows a rear view of the example yoke 1150 of the nasal respiratory interface 1100 shown in FIG. 31.

As shown in FIGS. 45A-45C, the rear wall 1175 of the yoke 1150 can include support regions 1181. In certain embodiments, the support regions 1181 can be shaped to extend below the lower edge of the frame 1110. The support regions 1181 can be configured to provide a contact point with the seal 1135. In various embodiments, the support regions 1181 can contact the seal and prevent the seal from overinflating and/or erupting. For example, the support regions 1181 can be rigid and act as stops to prevent the seal from overinflating, from losing shape, and/or from breaking away from the user's nares when in use. The region of the seal 1135 that contacts the frame 1110 is typically bean shaped as opposed to oval shaped. As the frame 1110 is oval shaped in various embodiments, additional structure can help support the bean shape of the region of the seal 1135 that contacts the frame 1110 and yoke 1150 combination. This structure can be provided in certain embodiments by the support regions 1181. Geometry of the seal other than bean shape can be contemplated. Accordingly, the yoke 1150 can be modified to accommodate any seal shape and size. In addition, in various embodiments, as shown in FIG. 45B, when the yoke 1150 and the frame 1110 are coupled, the front surface 1111 of the frame 1110 and the front surface 1151 of the yoke 1150 can form a substantially flush surface.

In various embodiments, the yoke 1150 can also include a connector 1176 to connect the yoke 1150 to the headgear system. In the example show in FIGS. 44A-44B and FIG. 45C, the connector 1176 includes protrusions extending from the rear surface 1175 near the lateral edges 1153*a*, 1153*b* of the yoke 1150 to couple with recesses in the headgear. In the alternative, the connector 1176 can include recesses in the yoke 1150 to couple with protrusions in the headgear. The type of connector 1176 is not particularly limited and can be any connector known in the art or yet to be developed. In other embodiments, the yoke 1150 can be moulded to the headgear to form continuous unit. In such embodiments, the total number of components in the assembly can be reduced.

Figure 46B:
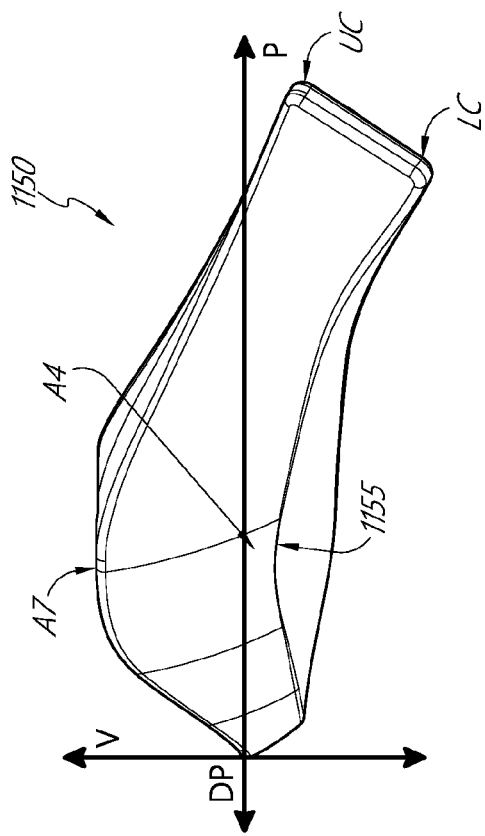
FIGS. 46A, 46B, and 46C show left side views of the example yoke 1150 showing example features.
Figure 46A:
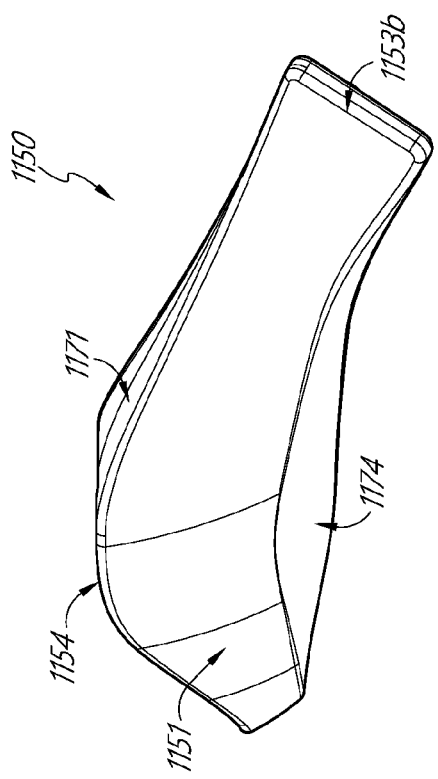
Figure 46C:
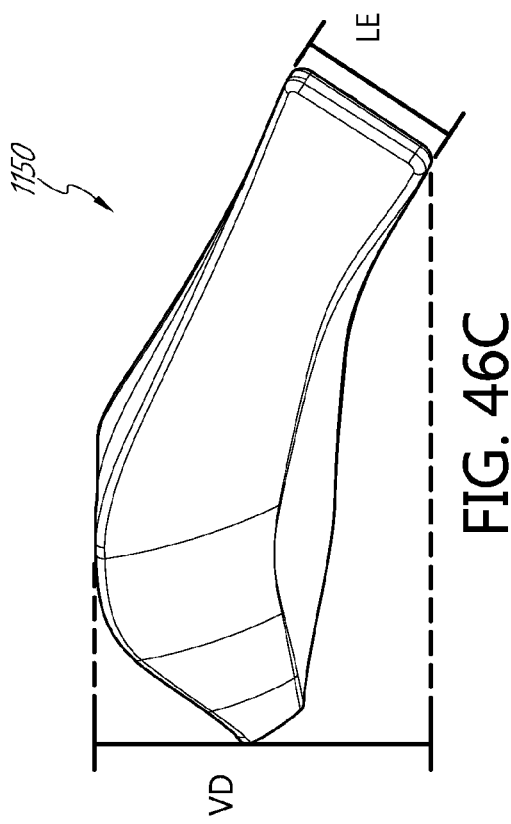

FIGS. 46A-46C show left side views (with respect to the patient) of the example yoke 1150 showing example features. The yoke 1150 includes a front surface 1151, a top surface 1171, and a bottom surface 1174 (or the lower surface 1151*b* shown in FIGS. 40 and 41). FIGS. 46A-46C show an angled arrangement of the bottom surface 1174 of the yoke 1150 such that the bottom surface 1174 can be angled toward the seal to act as support and/or limits for the seal. A vertical axis V can pass through the most distal point DP of the yoke 1150 in the vertical direction and a proximal axis P can pass through the distal point DP in the proximal direction. The front surface 1151, the top surface 1171, and the bottom surface 1174 can extend from this distal point DP in the proximal direction. The front surface 1151 can initially extend vertically lower from the proximal axis P as the proximal displacement increases.

In various embodiments, the upper edge 1154 of the front surface 1151 can span in the proximal direction from the origin DP vertically to an apex A7. The upper edge 1154 of the front surface 1151 can then extend vertically downward with increased proximal displacement from the origin DP to the lateral edge 1153*b* of the yoke 1150. The lower edge 1155 of the front surface 1151 can span in the proximal direction from the origin DP vertically to an apex A4. The lower edge 1155 of the front surface 1151 can then extend vertically downward with increased proximal displacement from the origin DP to the lateral edge 1153*b* of the yoke 1150.

In various embodiments, the bottom surface 1174 can be adjacent to the front surface 1151, and can extend in the proximal direction below the front surface 1151. The top surface 1171 can extend further in the proximal direction than the bottom surface 1174, resulting in an angled lateral edge 1153*b* with respect to both the vertical V and proximal P axes. Another way of expressing this is that the upper corner UC of the lateral edge 1153*b* can be proximally displaced from the lower corner LC of the lateral edge 1153*b* as shown in FIGS. 46A-46C.

As described herein, the vertical dimension VD of the yoke 1150 can be about 15 mm to about 25 mm, or can be in a range between any of the foregoing values, such as 19.5 mm±1 mm (e.g., about 18.5 mm, about 19 mm, about 19.5 mm, about 20 mm, or about 20.5 mm). In some advantageous embodiments, the length LE of the lateral edge 1153*a*, 1153*b* can be about 5 mm to about 15 mm, or can be in a range between any of the foregoing values, such as 9.6 mm±1.6 mm (e.g., about 8 mm, about 9 mm, about 10 mm, or about 11 mm). Other values for the vertical dimension VD of the yoke 1150 and/or the length LE of the lateral edge 1153*a*, 1153*b* of the yoke are possible. These values can be designed according to the intended patient, the intended application, and/or the dimensions of the other components in the assembly 1010. As described herein, in some embodiments, the yoke 1150 can be continuous with the headgear (e.g., no connector 1176). In some such embodiments, the length LE might not exist as there may be no lateral edge 1153*a*, 1153*b* of the yoke 1150.

Figure 47A:
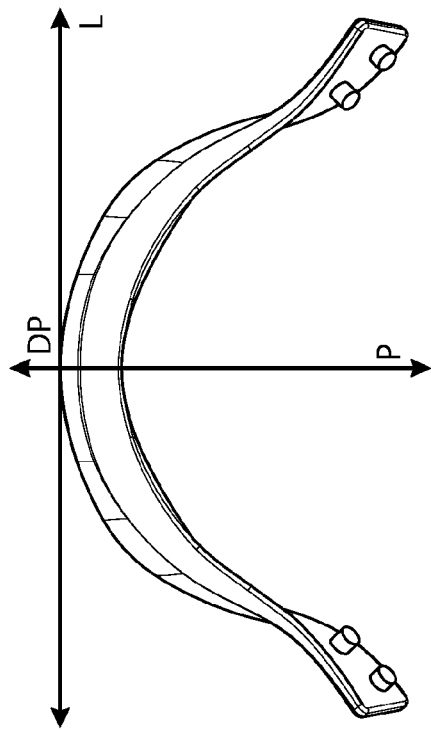
FIGS. 47A-47B show bottom views of the example yoke 1150 of the nasal respiratory interface 1100 shown in FIG. 31.
Figure 47B:
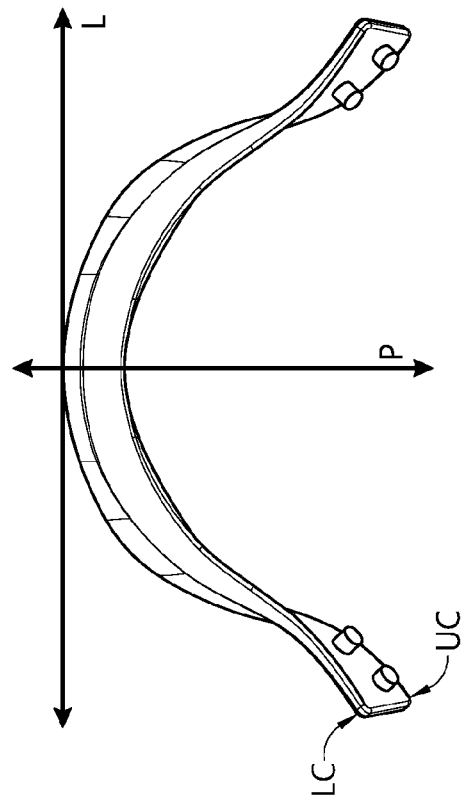

FIGS. 47A-47B show bottom views of the example yoke 1150 of the nasal respiratory interface 1100 shown in FIG. 31. As shown in the bottom view, the yoke 1150 can include a front surface 1151, a bottom surface 1174, and a rear surface (e.g., rear wall) 1175. A lateral axis L can pass through the most distal point DP of the yoke 1150 in the lateral direction, and a proximal axis P can pass through the distal point DP in the proximal direction. As the bottom surface 1174 extends laterally from the proximal axis P, the front surface 1151 can curve so that it is concave in the proximal direction in some embodiments.

Figure 48A:
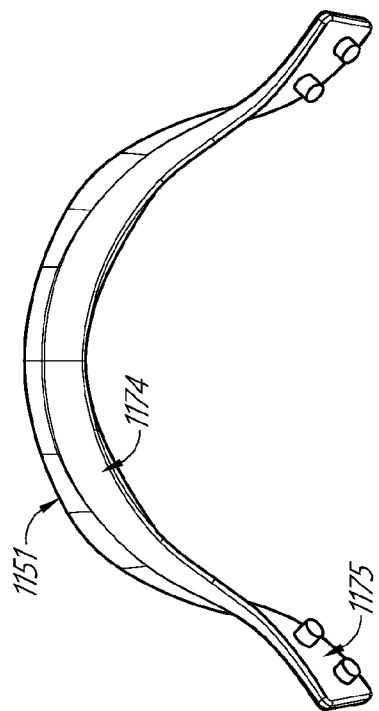
FIGS. 48A-48B show bottom views of the example yoke 1150 showing curvature.
Figure 48B:
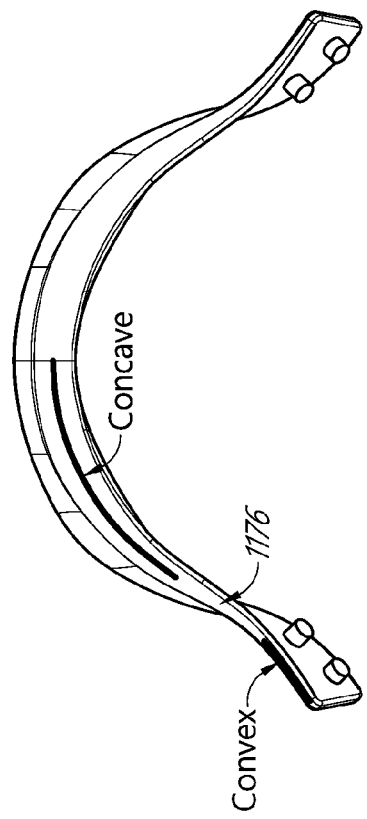

FIGS. 48A-48B show bottom views of the example yoke 1150 showing curvature. At an inflection region 1176 laterally displaced from the proximal axis P, the curve can transition from a concave shape to a convex shape relative to the proximal direction. The inflection region 1176 of the bottom surface 1174 can be shorter than the inflection region 1168 of the top surface 1171 (shown in FIGS. 43A-43B). Additionally, the inflection region 1176 of the bottom surface 1174 can be laterally displaced from the inflection region 1168 of the top surface 1171. As described herein, the result of this can include a twisting of the lateral portions of the yoke 1150 along their length. This effect can be shown by the lateral displacement between the lateral edge lower corner LC and the lateral edge upper corner UC in FIG. 48B.

Figure 49B:
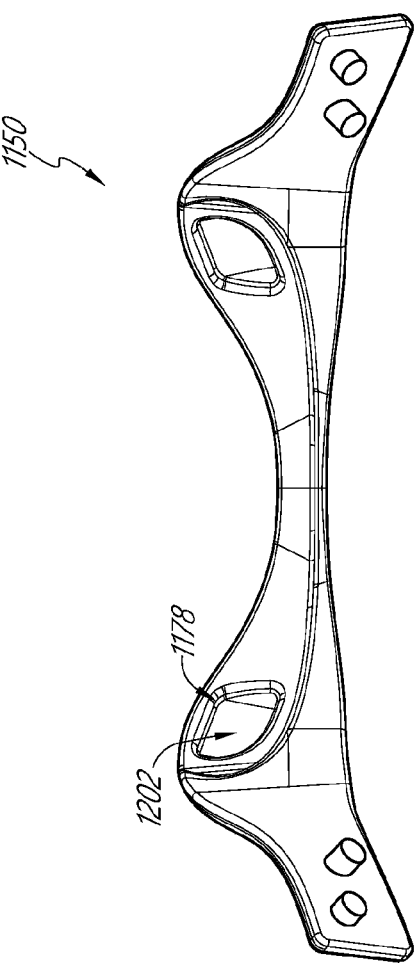
FIG. 49A shows a front view of the example frame 1110 and FIG. 49B shows a rear view of the example yoke 1150.
Figure 49A:
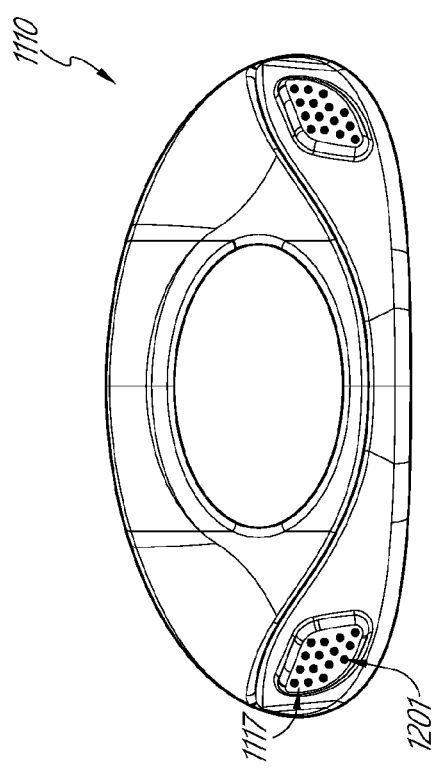

FIG. 49A shows a front view of the example frame 1110 and FIG. 49B shows a rear view of the example yoke 1150. As shown in FIGS. 49A-49B, certain embodiments can include a bias hole system 1201 incorporated into the frame 1110 and/or into the yoke 1150. For example, the locating projections 1117 of the frame 1110 can include bias flow holes 1201. The corresponding recessed locators 1178 of the yoke 1150 can also include bias flow holes 1201. As another example, the locating projections 1117 of the frame 1110 and/or the corresponding locators 1178 of the yoke 1150 can include a diffusor 1202 in addition to or instead of the bias holes to help reduce noise in some embodiments. Incorporating bias flow holes and/or a diffusor into the frame 1110 and/or into the yoke 1150 can enable the bias holes/diffusor to be included in a way that can minimize the profile of the frame 1110 and yoke 1150, as no additional space would be necessary in some such embodiments. Further, the bias flow holes 1201 do not necessarily need to be implemented within the locating projections 1117 of the frame 1110 or corresponding locators 1178 of the yoke 1150. They can be placed in any number of spots throughout the frame 1110, yoke 1150, and/or the conduit connector 1190.

A number of alternate modifications can be made. As an example, features described herein for the frame 1110 can be included on the yoke 1150, and features described herein for the yoke 1150 can be included on the frame 1110. For instance, the yoke 1150 can comprise a recessed surface 1116, and the frame 1110 can comprise a recessed wall 1177 and a shelf 1172. The recessed wall 1177 of the frame 1110 can be configured to mate with the recessed surface 1116 of the yoke 1150. In some instances, the yoke 1150 can sit on the shelf 1172 of the frame 1110. The front surface 1151 of the yoke 1150 can comprise the recessed surface 1116 of the yoke 1150, and the rear surface 1112 of the frame 1110 can comprise the recessed wall 1177 of the frame 1110. When coupled, the front surface 1111 of the frame 1110 and the front surface 1151 of the yoke 1150 can form a substantially flush surface. The recessed wall 1177 of the frame 1110 can be configured to mate with the recessed surface 1116 of the yoke 1150 via a connection comprising at least one locating projection 1117 and at least one recessed locator 1178. For example, at least one locating projection 1117 can comprise at least two locating projections 1117 and at least one recessed locator 1178 can comprise at least two recessed locators 1178. At least one locating projection 1117 or at least one recessed locator 1178 can comprise bias flow holes 1201 or a diffuser 1202.

Figure 50:
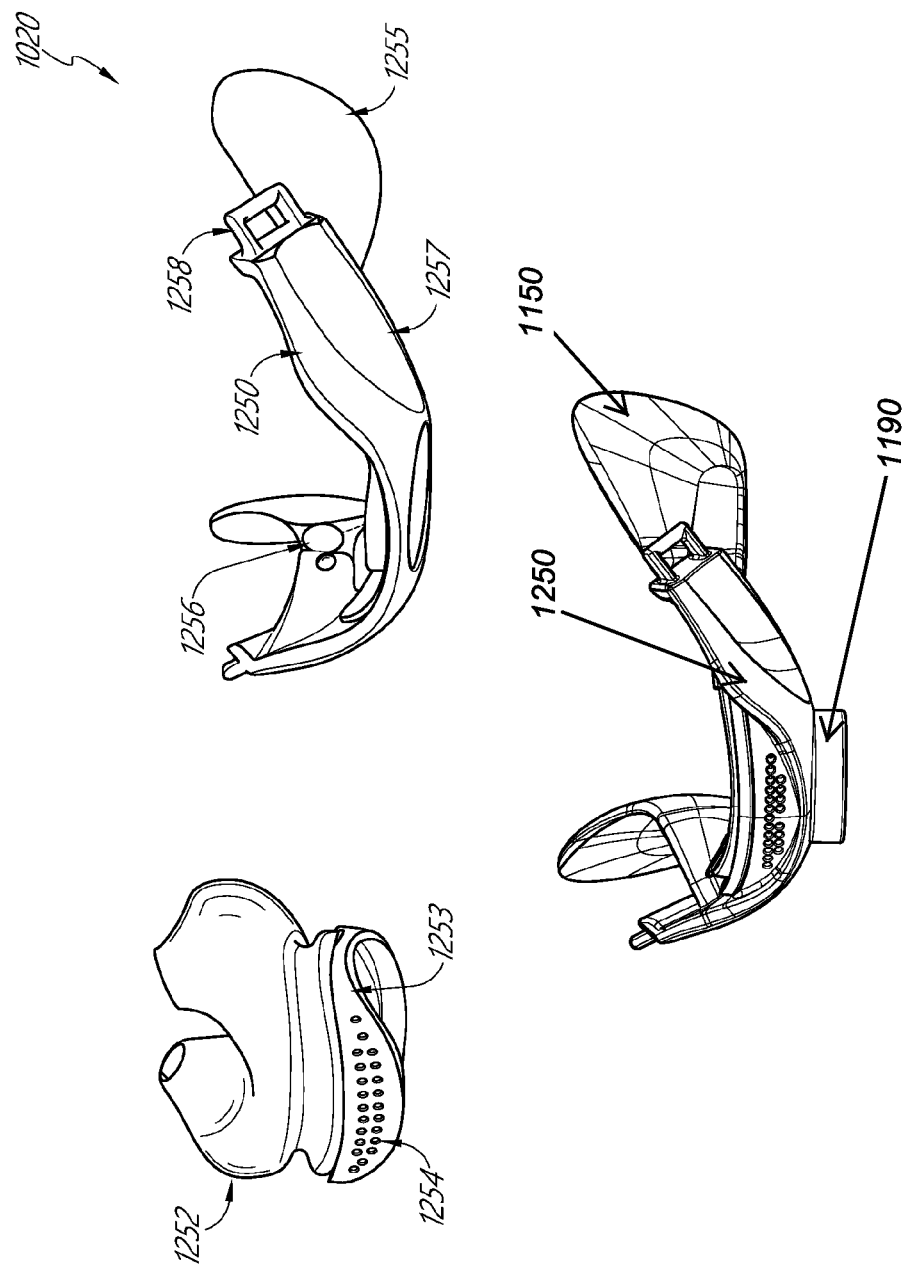
FIG. 50 shows an example nasal OSA therapy assembly 1020 in accordance with certain embodiments described herein.

As another example, FIG. 50 shows an example nasal OSA therapy assembly 1020 in accordance with certain embodiments described herein. The assembly 1020 can include a frame 1250 that can be coupled to a seal for a nasal pillow 1252 via a seal clip 1253. As shown FIG. 50, bias holes 1254 (or a diffuser mat) can be included in the seal clip 1253. In some embodiments utilizing a diffuser mat in the seal clip 1253, the diffuser mat can be replaced when the seal clip 1253 is replaced.

As also shown in FIG. 50, the frame 1250 can include or be coupled to one or more outriggers 1255. An outrigger 1255 can help limit movement of the frame 1250 caused by a pulling force of a gas delivery conduit. In some such embodiments, the connection 1256 between the frame 1250 and one or more outriggers 1255 can appear substantially seamless with the frame 1250. The frame 1250 can also include one or more concave touch points 1257 to help assist the patient holding it. In addition, the frame 1250 can include one or more clips 1258 on the lateral ends of the frame 1250 to allow coupling with headgear (not shown).

Figure 51A:
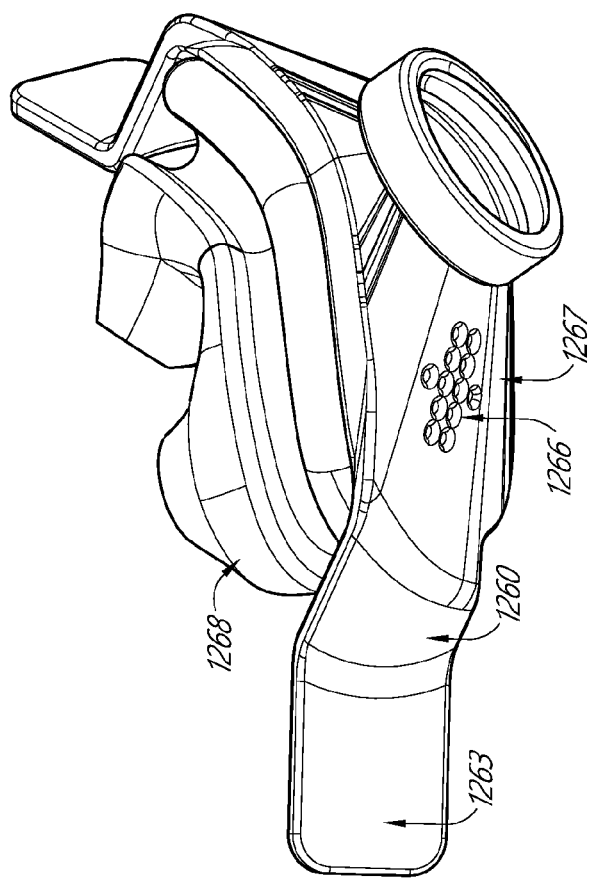
FIGS. 51A-51B show another example nasal OSA therapy assembly 1030 in accordance with certain embodiments described herein.
Figure 51B:
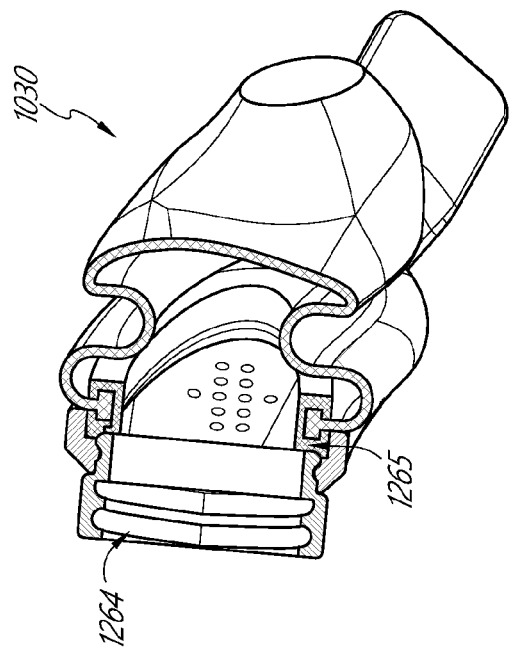

FIGS. 51A and 51B show another example nasal OSA therapy assembly 1030 in accordance with certain embodiments described herein. The example interface 1030 can include a frame 1260 that can be functional and relatively short with little, if no, excess space. In some such embodiments, the frame 1260 can be brought close (e.g., as close as possible) to the patient's face to improve performance. For example, the connection 1263 of the frame 1260 to headgear can be close to the nose. In some embodiments, the connection of the gas delivery conduit (e.g., tube) 1264 can include a permanent clip 1265 so that relatively long sealing surfaces are not required for swivelling. The bias system can be placed on either side of the gas delivery conduit 1264. For example, the frame 1260 can include bias holes (or a diffuser mat) 1266 on one or more sides of the frame 1260. Paddles 1267 can be present on the underside of the frame 1260 to help support the geometry (e.g., bean shape) of the seal of the nasal pillow 1268.

Figure 52A:
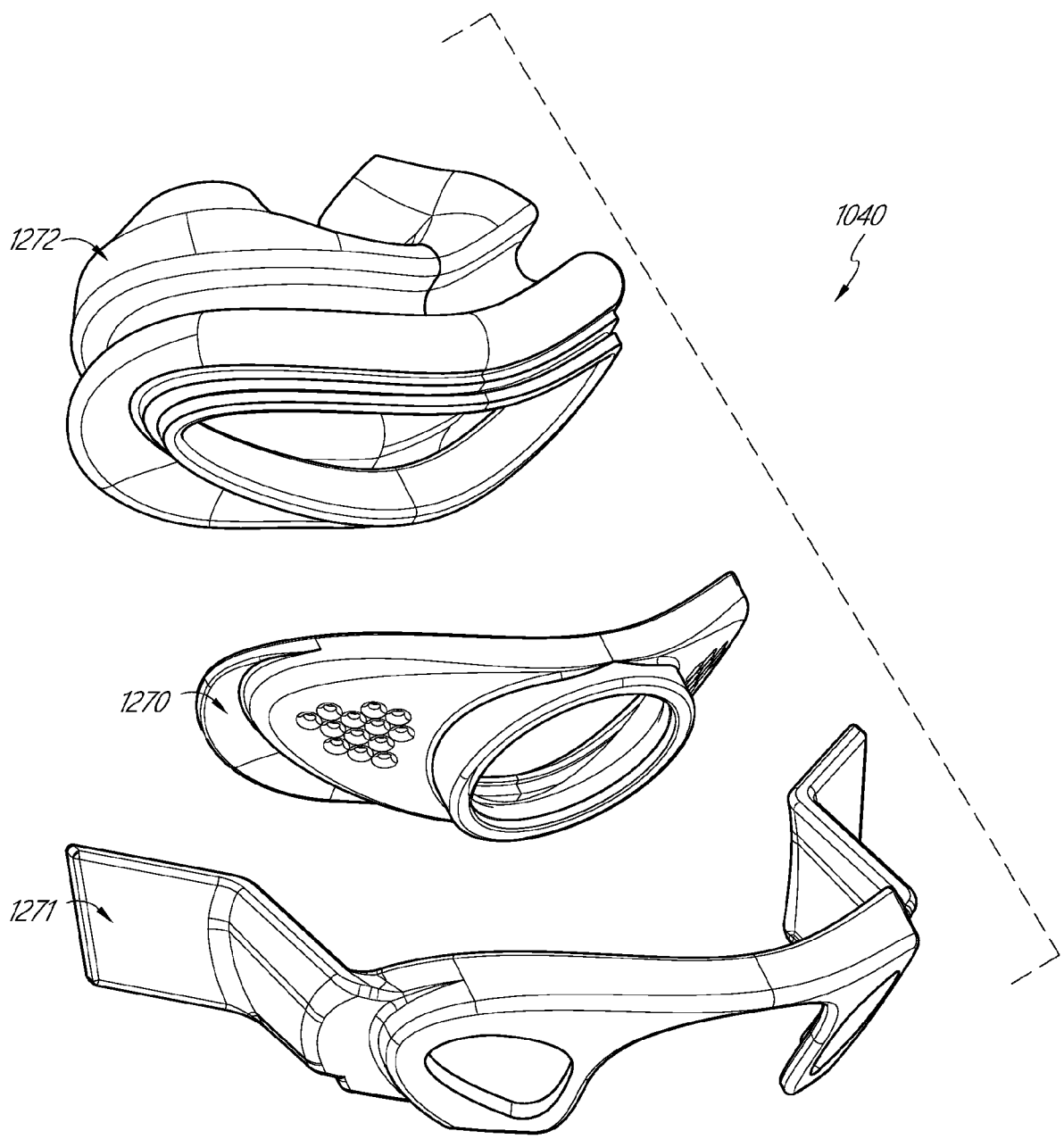
FIGS. 52A-52B show yet another example nasal OSA therapy assembly 1040 in accordance with certain embodiments described herein.
Figure 52B:
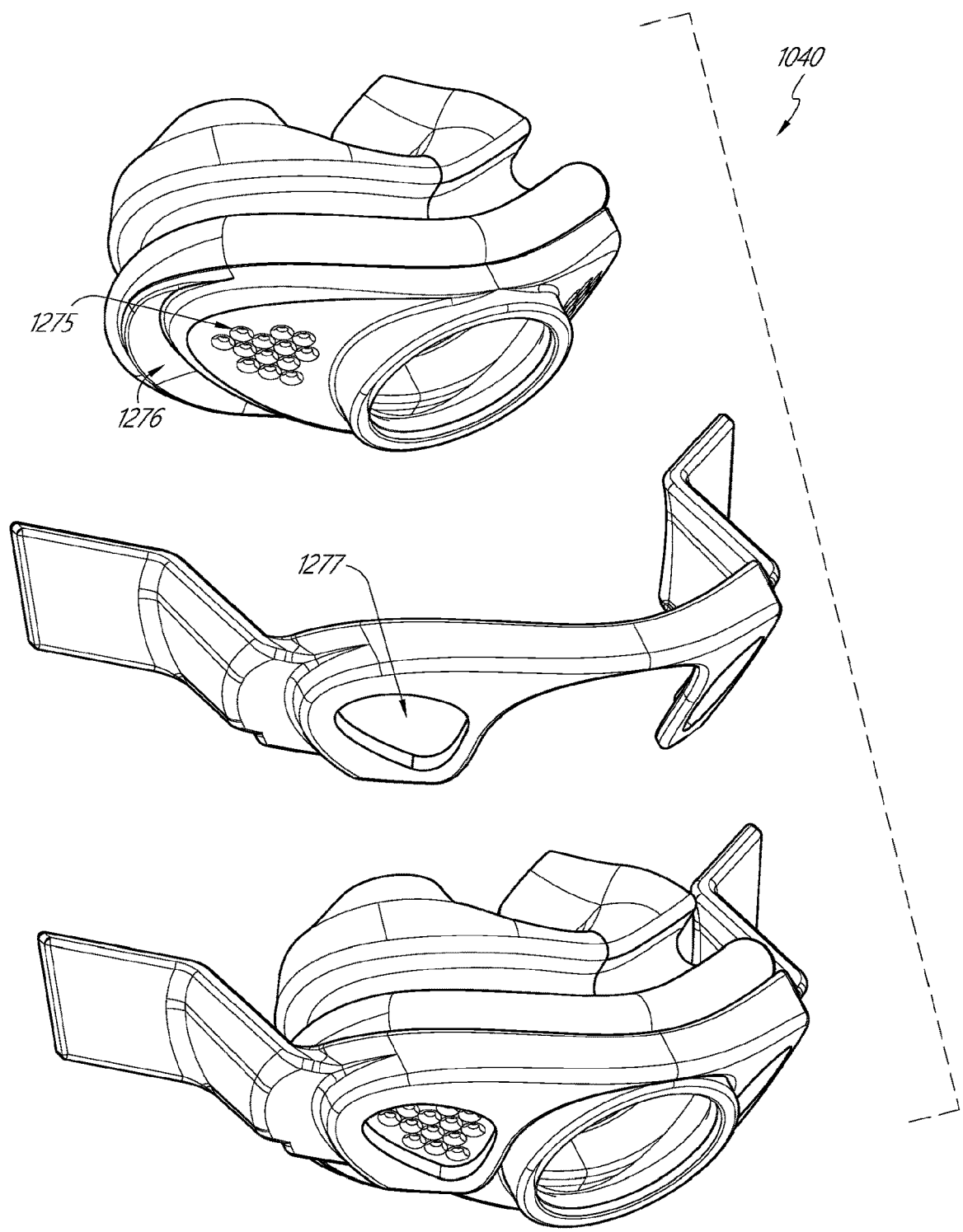

FIGS. 52A and 52B show yet another example nasal OSA therapy assembly 1040 in accordance with certain embodiments described herein. The interface 1040 can include a system including at least two elements: an air delivery path and headgear. In some such embodiments, the system can include a frame 1270 and a yoke 1271. The frame 1270 can connect to the seal of the nasal pillow 1272. The frame 1270 can include bias holes 1275. The frame 1270 can also include paddles 1276 to help support the geometry of the seal. The yoke 1271 can connect to the frame 1270, e.g., utilizing recessed paddles 1276 for connection support. The yoke 1271 can also provide an interface for the headgear, e.g., a substantially seamless connection to the headgear in some embodiments. The yoke can also include one or more overmoulded diffusor mats 1277 for the bias holes 1275.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Recitation of ranges herein is merely intended to serve as a shorthand method of referring individually to each separate sub-range or value falling within the range, unless otherwise indicated herein, and each separate sub-range or value is incorporated into the specification as if it were individually recited herein.

Reference to any prior art in this specification is not, and should not be taken as, an acknowledgement or any form of suggestion that that prior art forms part of the common general knowledge in the field of endeavor in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. An adjustable headgear, comprising:
   a first strap having a first endcap attached to the first strap, the first endcap having a first through hole;
   a second strap having a second endcap attached to the second strap, the second endcap having a second through hole, wherein the first strap passes through the second through hole and the second strap passes through the first through hole; and
   a sleeve extending between the first and second endcaps and surrounding the first and second straps.

2. The adjustable headgear of claim 1, wherein the sleeve is braided.

3. The adjustable headgear of claim 1, wherein the sleeve is elastic.

4. The adjustable headgear of claim 1, wherein the first and second endcaps are overmolded onto the sleeve.

5. The adjustable headgear of claim 1, further comprising a detent arrangement comprising a plurality of relative adjustment positions between the first strap and the second strap.

6. The adjustable headgear of claim 1, further comprising a first tab coupled to the first endcap and a second tab coupled to the second endcap.

7. The adjustable headgear of claim 6, wherein the first tab and the second tab are coupled to a center of the respective first endcap and second endcap.

8. The adjustable headgear of claim 1, wherein the first strap and the second strap are positioned one on top of the other when overlapped.

9. The adjustable headgear of claim 1, wherein the first strap and the second strap are positioned one beside the other when overlapped.

10. The adjustable headgear of claim 1, wherein the first strap and the second strap are located in one or both of a top strap and a rear strap of the headgear.

11. The adjustable headgear of claim 1, wherein the first strap and the second strap are in frictional contact with one another to provide a resistance to relative movement of the first strap and the second strap.

12. The adjustable headgear of claim 1, wherein the first strap and the second strap each comprise a plastic core and a textile covering.

13. The adjustable headgear of claim 12, wherein the textile covering covers an inner and an outer surface of each of the first strap and the second strap.

14. The adjustable headgear of claim 13, wherein the textile covering comprises a first layer and a second layer.

15. The adjustable headgear of claim 13, wherein the textile covering comprises a tube.

* * * * *